(12) United States Patent
Gerecht et al.

(10) Patent No.: US 10,987,375 B2
(45) Date of Patent: Apr. 27, 2021

(54) METHODS OF INDUCING VASCULAR MORPHOGENSIS

(71) Applicant: THE JOHNS HOPKINS UNIVERSITY, Baltimore, MD (US)

(72) Inventors: Sharon Gerecht, Severna Park, MD (US); Kyung Min Park, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 15/789,225

(22) Filed: Oct. 20, 2017

(65) Prior Publication Data
US 2018/0092941 A1 Apr. 5, 2018

Related U.S. Application Data

(63) Continuation of application No. 14/536,392, filed on Nov. 7, 2014.
(Continued)

(51) Int. Cl.
A61K 31/738 (2006.01)
C12P 19/08 (2006.01)
(Continued)

(52) U.S. Cl.
CPC .............. A61K 31/738 (2013.01); A61K 9/06 (2013.01); A61K 35/33 (2013.01);
(Continued)

(58) Field of Classification Search
None
See application file for complete search history.

(56) References Cited

U.S. PATENT DOCUMENTS

2006/0009550 A1* 1/2006 Messersmith .......... A61L 31/06
524/17
2007/0190122 A1 8/2007 Davis et al.
(Continued)

FOREIGN PATENT DOCUMENTS

JP 2012/050343 A 2/2012
WO 2012/060544 A1 5/2012

OTHER PUBLICATIONS

Lee et al., Synthesis and Gelation of DOPA-Modified Poly(ethylene glycol) Hydrogels. Biomacromolecules 2002, 3, 1038-1047 (Year: 2002).*
(Continued)

Primary Examiner — Arthur S Leonard
(74) Attorney, Agent, or Firm — Johns Hopkins Technology Ventures

(57) ABSTRACT

Novel hydrogels that can serve as 3D hypoxic microenvironments are disclosed. Oxygen controllable, hypoxia-inducible hydrogels (HI hydrogels) are composed of a phenolic agent and polymer backbone, which can form hydrogel networks via oxygen consumption in an enzyme-mediated crosslinking reaction. The HI hydrogels are degradable, cytocompatible, and have tunable mechanical properties. Oxygen levels and gradients within the HI hydrogels are controlled and precisely predicted. As a result, the HI hydrogels induce prolonged hypoxic conditions. The HI hydrogels guide vascular morphogenesis in vitro by activating hypoxia-inducible factors and promote neovascularization from tissue, as well as stimulate tissue in dynamic in vivo environments. The HI hydrogels are a new class of biomaterials that are useful in many applications, ranging from the engineering of de novo tissues and disease models to the treatment of vascular disorders.

6 Claims, 44 Drawing Sheets

Related U.S. Application Data

(60) Provisional application No. 62/054,849, filed on Sep. 24, 2014, provisional application No. 61/901,804, filed on Nov. 8, 2013.

(51) Int. Cl.
  A61K 9/00    (2006.01)
  A61L 27/38   (2006.01)
  A61L 27/52   (2006.01)
  A61K 9/06    (2006.01)
  A61K 35/33   (2015.01)
  A61K 38/17   (2006.01)
  C12P 21/00   (2006.01)

(52) U.S. Cl.
  CPC .......... *A61K 38/1709* (2013.01); *A61L 27/38* (2013.01); *A61L 27/52* (2013.01); *C12P 19/08* (2013.01); *C12P 21/00* (2013.01)

(56) References Cited

U.S. PATENT DOCUMENTS

| | | | |
|---|---|---|---|
| 2008/0241878 A1* | 10/2008 | Boumans | A23J 3/04 435/68.1 |
| 2010/0215715 A1* | 8/2010 | Han | A61K 35/12 424/423 |
| 2012/0070433 A1 | 3/2012 | Kurisawa et al. | |
| 2014/0050766 A1* | 2/2014 | Levenberg | A61L 27/225 424/400 |
| 2015/0250890 A1 | 9/2015 | Park et al. | |

OTHER PUBLICATIONS

Pedroso et al., Improved Survival, Vascular Differentiation and Wound Healing Potential of Stem Cells Co-Cultured with Endothelial Cells. PLoS One, 2011, vol. 6, issue 1, e16114, pp. 1-12. (Year: 2011).*
McKeown, SR. Defining normoxia, physoxia and hypoxia in tumours—implications for treatment response. Br J Radiol. Mar. 2014; 87(1035):1-12 (Year: 2014).*
Park et al., In situ cross-linkable gelatin-poly(ethylene glycol)-tyramine hydrogel via enzyme-mediated reaction for tissue regenerative medicine. J. Mater. Chem., 2011, 21, 13180-13187 (Year: 2011).*
Duckworth et al., Physicochemical and kinetic properties of mushroom tyrosinase. J Biol Chem. Apr. 10, 1970;245(7):1613-25. (Year: 1970).*
Jin et al., Tyrosinase-mediated in situ forming hydrogels from biodegradable chondroitin sulfate-tyramine conjugates. Polym Int 2013; 62: 353-361 (Year: 2013).*
Chen et al. In Vitro Protein-Polysaccharide Conjugation: Tyrosinase-Catalyzed Conjugation of Gelatin and Chitosan. Biopolymers, 2002, 64:292-302. (Year: 2002).*
Rocasalbas et al., Laccase-assisted formation of bioactive chitosan/gelatin hydrogel stabilized with plant polyphenols. Carbohydrate Polymers, 2013, 92:989-996 (Year: 2013).*
Duran et al.,Applications of laccases and tyrosinases (phenoloxidases) immobilized on different supports: a review. Enzyme and Microbial Tech, 2002, 31:907-931 (Year: 2002).*
Jin et al., Enzymatically Crosslinked Dextran-Tyramine Hydrogels as Injectable Scaffolds for Cartilage Tissue Engineering. Tissue Engineering: Part A vol. 16, No. 8, 2010, p. 2429-2440 (Year: 2010).*
Niklason et al., Functional Arteries Grown in Vitro. Science, 1999, 284:489-493 (Year: 1999).*
Abaci, H.E. et al., "Unforeseen decreases in dissolved oxygen levels affect tube formation kinetics in collagen gels" American journal of physiology: Cell physiology, 2011; 301:C431-440.
Abaci, H.E., et al., "Adaptation to oxygen deprivation in cultures of human pluripotent stem cells, endothelial progenitor cells, and umbilical vein endothelial cells" Am J Physiology Cell physiology, 2010; 298: C1527-1537.
Abaci, H.E., et al., "Design and development of microbioreactors for long-term cell culture in controlled oxygen microenvironments" Biomedical microdevices, 2012: 14:145-152.
Annabi, N. et al., "25th Anniversary Article: Rational Design and Applications of Hydrogels in Regenerative Medicine" Adv. Mater 2014, 26, 85.
Augustin, H.G. et al., "Control of vascular morphogenesis and homeostasis through the angiopoietin—Tie system" Nature reviews. Molecular cell biology 2009; 10:165-177.
Ben-Yosef, Y. et al., "Regulation of Endothelial Matrix Metalloproteinase-2 by Hypoxia/Reoxygenation" Circulation research, 2002; 90:784-791.
Covello, K.L. et al., "HIFs, Hypoxia, and Vascular Development" Current topics in developmental biology, 2004; 62:37-54.
Cuchiara, M.P. et al., "Integration of Self-Assembled Microvascular Networks with Microfabricated PEG-Based Hydrogels" Advanced functional materials, 2012; 22:4511-4518.
Cushing, M.C., et al., "Hydrogel Cell Cultures" Science, 2007; 316: 1133-1134.
De Jong et al., "Biodegradable hydrogels based on stereocomplex formation between lactic acid oligomers grafted to dextran" J. Controlled Release 2001, 72, 47.
DeForest, C.A. et al., "Sequential click reactions for synthesizing and patterning three-dimensional cell microenvironments" Nature materials, 2009; 8:659-664.
Du, J. et al., "Combination of HIF-1a gene transfection and HIF-1-activated bone marrow-derived angiogenic cel infusion improves burn wound healing in aged mice" Gene Ther. 2013, 20, 1070.
Ferrara, N., et al., "The biology of VEGF and its receptors" Nature medicine, 2003; 9:669-676.
Fischer, B. et al., "Oxygen tension in the oviduct and uterus of rhesus monkeys, hamsters and rabbits" J reproduction and fertility, 1993; 99:673-679.
Fong, G.H., "Regulation of angiogenesis by oxygen sensing mechanisms" Journal of molecular medicine, 2009; 87:549-560.
Gassmann, M. et al., "Oxygen supply and oxygen-dependent gene expression in differentiating embryonic stem cells" PNAS USA, 1996; 93:2867-2872.
Hanjaya-Putra, D. et al., "Spatial control of cell-mediated degradation to regulate vasculogenesis and angiogenesis in hyaluronan hydrogels" Biomaterials, 2012; 33:6123-6131.
Heddleston, J.M. et al., "Hypoxia inducible factors in cancer stem cells" British J Cancer, 2010; 102:789-795.
Hielscher, A., et al., "Hypoxia Affects the Structure of Breast Cancer Cell-Derived Matrix to Support Angiogenic Responses of Endothelial Cells" J Carcinog Mutagen., 2013; S13:005.
Hong, et al., "The Role of Hypoxia-Inducible Factor in Wound Healing" Adv. Wound Care 2014.
Huebsch, N. et al., "Inspiration and application in the evolution of biomaterials" Nature, 2009; 462: 426-432.
Jin, R. et al., "Enzyme-mediated fast in situ formation of hydrogels from dextran-tyramine conjugates" Biomaterials 2007, 28, 2791.
Jopling, C. et al., "Hypoxia Induces Myocardial Regeneration in Zebrafish" Circulation, 2012; 126:3017-3027.
Karin Eisinger-Mathason et al., "Hypoxia-Dependent Modification of Collagen Networks Promotes Sarcoma Metastasis" Cancer Discovery, 2013; DOI: 10.1158/2159-8290.
Keith, B. et al., "Hypoxia-Inducible Factors, Stem Cells, and Cancer" Cell, 2007; 129:465-472.
Khetan, S. et al., "Degradation-mediated cellular traction directs stem cell fate in covalently crosslinked three-dimensional hydrogels" Nature materials, 2013; 12:458-465.
Kilian, K.A. et al., "Geometric cues for directing the differentiation of mesenchymal stem cells" PNAS USA, 2010; 107:4872-4877.
Ko, U. P. Shinde, B. Yeon, B. Jeong, "Recent progress of in situ formed gels for biomedical applications" Prog. Polym. Sci. 2013, 38, 672.
Kusuma, S., et al., "The extracellular matrix is a novel attribute of endothelial progenitors and of hypoxic mature endothelial cells" FASEB Journal, 2012: 26:4925-4936.

(56) References Cited

OTHER PUBLICATIONS

LaVan, F. B. and Hunt, T. K., "Oxygen and wound healing" Clin. Plast. Surg. 1990, 17, 463.
Lee, Y.M. et al., Determination of Hypoxic Region by Hypoxia Marker in Developing Mouse Embryos In Vivo: A Possible Signal for Vessel Development Developmental dynamics, 2001; 220:175-186.
Lin, C.M. et al., "Ferulic acid augments angiogenesis via VEGF, PDGF and HIF-1α" J nutritional biochemistry, 2010; 21:627-633.
Luo, Y., et al., "A photolabile hydrogel for guided three-dimensional cell growth and migration" Nature materials, 2004; 3: 249-253.
Malda, J. et al., "25th Anniversary Article: Engineering Hydrogels for Biofabrication" Adv. Mater. 2013, 25, 5011.
Maltepe, E. and Simon, M. C., J. "Oxygen, genes, and development: An analysis of the role of hypoxic gene regulation during murine vascular development" Mol. Med. 1998, 76, 391.
Manalo, D.J. et al., "Transcriptional regulation of vascular endothelial cell responses to hypoxia by HIF-1" Blood, 2005; 105:659-669.
Marti, H.J. et al., "Hypoxia-Induced Vascular Endothelial Growth Factor Expression Precedes Neovascularization after Cerebral Ischemia" Am J Pathology, 2000; 156:965-976.
Martino, M.M., et al., "Engineering the Growth Factor Microenvironment with Fibronectin Domains to Promote Wound and Bone Tissue Healing" Science translational medicine, 2011; 3: 100ra189.
Mattinen, et al., "Laccase-catalyzed polymerization of tyrosine-containing peptides" FEBS J. 2005; 272: 3640.
Mazumdar, J. et al., "Hypoxia-inducible factors in stem cells and cancer" Cell. Mol. Med. 2009, 13, 4319.
Oh, S.H., et al., "Oxygen generating scaffolds for enhancing engineered tissue survival" Biomaterials, 2009; 30:757-762.
O'Toole, et al., "Hypoxia Increases Human Keratinocyte Motility on Connective Tissue" J. Clin. Invest. 1997, 100, 2881.
Ottino, P. et al., "Hypoxia activates matrix metalloproteinase expression and the VEGF system in monkey choroid-retinal endothelial cells: Involvement of cytosolic phospholipase A2 activity" Molecular vision, 2004; 10:341-350.
Pan, Y. et al., "Multiple Factors Affecting Cellular Redox Status and Energy Metabolism Modulate Hypoxia-Inducible Factor Prolyl Hydroxylase Activity In Vivo and In Vitro" Molecular and cellular biology, 2007; 27:912-925.
Park, K. M. et al., "In Situ SVVYGLR Peptide Conjugation into Injectable Gelatin-Poly(ethylene glycol)-Tyramine Hydrogel via Enzyme-Mediated Reaction for Enhancement of Endothelial Cell Activity and Neo-Vascularization" Bioconjugate Chem. 2012, 23, 2042.
Park, K.M., et al., "In Situ Forming Hydrogels Based on Tyramine Conjugated 4-Arm-PPO-PEO via Enzymatic Oxidative Reaction" Biomacromolecules, 2010; 11: 706-712.
Park, K.M., et al., "In situ cross-linkable gelatin-poly(ethylene glycol)-tyramine hydrogel via enzyme-mediated reaction for tissue regenerative medicine" J Mater Chem; 2011; 21:13180-13187.
Park, S. Gerecht, "Hypoxia-inducible hydrogels" Nat. Commun. 2014, 5, 4075.
Peng, et al., "In Situ Formation of Biodegradable Dextran-Based Hydrogel via Michael Addition" J. Appl. Polym. Sci. 2013, 127, 577.
Place, E.S. et al., "Complexity in biomaterials for tissue engineering" Nature materials, 2009; 8: 457-470.
Pugh, C.W. et al., "Regulation of angiogenesis by hypoxia: role of the HIF system" Nature medicine, 2003; 9:677-684.
Riva, S., "Laccases: blue enzymes for green chemistry" Trends in biotechnology, 2006; 24:219-226.
Rosana, C.M. et al., "Potential applications of laccase in the food industry" Trends in Food Science & Technology, 2002; 13:205-216.
Semenza, G. L., "Hypoxia-inducible factor 1: oxygen homeostasis and disease pathophysiology" Trends Mol. Med. 2001, 7, 345.
Semenza, G.L, "Life with Oxygen" Science. 2007; 318:62-64.

Simon, M.C. et al., "The role of oxygen availability in embryonic development and stem cell function" Nature reviews: Molecular cell biology, 2008; 9:285-296.
Stroka, et al., "A biophysical view of the interplay between mechanical forces and signaling pathways during transendothelial cell migration" FEBS J. 2001, 15, 2445.
Thiele, J. et al., "25th Anniversary Article: Designer Hydrogels for Cell Cultures: A Materials Selection Guide" Adv. Mater. 2014, 26, 125.
Tibbitt M.W. et al., "Hydrogels as Extracellular Matrix Mimics for 3D Cell Culture" Biotechnology and bioengineering, 2009; 103:655-663.
Wei, J. H. et al., "Dextran-Based Self-Healing Hydrogels Formed by Reversible Diels—Alder Reaction under Physiological Conditions" Macromol. Rapid Commun. 2013, 34, 1464.
Zhang, L. et al., "Zwitterionic hydrogels implanted in mice resist the foreign-body reaction" Nature biotechnology, 2013; 31:553-556.
Zhang, Y. et al., "In vitro and in vivo evaluation of oxygen effects on a glucose oxidase based implantable glucose sensor" Analytica Chimica Acta, 1993; 281:513-520.
Wang, L., et al., "Injectable biodegradable hydrogels with tunable mechanical properties for the stimulation of neurogenesic differentiation of human mesenchymal stem cells in 3D culture" Biomaterials 31 (2010) 1148-1157.
Huang, N., et al., "Mesenchymal stem cells for vascular regeneration" Regen Med. Nov. 2008 ; 3(6): 877-892. doi:10.2217/17460751.3.6.877.
Selinheimo, E., "Tyrosinase and laccase as novel crosslinking tools for food biopolymers" VTT Publications 693, Helsinki University, pp. 1-117.
Horst, O., et al., "Stem cell and biomaterials research in dental tissue engineering and regeneration" Dent Clin N Am 56 (2012) 495-520 doi:10.1016/j.cden.2012.05.009.
ISR and Written Opinion issued in International Application PCT/US2014/064686 dated Jan. 29, 2015.
Dogan, A., et al., "Controlled release of EGF and bFGF from dextran hydrogels in vitro and in vivo" J Biomed Mater Res B Appl Biomater. Jul. 2005;74(1):504-10.
Chun. T., et al., "MT1-MMP-dependent neovessel formation within the confines of the three-dimensional extracellular matrix" J Cell Biol. Nov. 22, 2004; 167(4): 757-767.
Davis, G., et al., "Endothelial Extracellular Matrix Biosynthesis, Remodeling, and Functions During Vascular Morphogenesis and Neovessel Stabilization" Circ Res. 2005;97:1093-1107.
Egler, A., "Matrix Elasticity Directs Stem Cell Lineage Specification" Cell 126, 677-689, Aug. 25, 2006.
Hanjaya-Putra, D., et al., "Controlled activation of morphogenesis to generate a functional human microvasculature in a synthetic matrix" Blood. 2011;118(3):804-815.
Lutolf, M., et al., "Synthetic biomaterials as instructive extracellular microenvironments for morphogenesis in tissue engineering" Nature Biotechnology vol. 23 No. 1 Jan. 2005.
Lutolf, M., et al., "Synthetic matrix metalloproteinase-sensitive hydrogels for the conduction of tissue regeneration: Engineering cell-invasion characteristics" PNAS, 2003, vol. 100, No. 9, pp. 5413-5418.
Stratman, A., et al., "Endothelial cell lumen and vascular guidance tunnel formation requires MT1-MMP-dependent proteolysis in 3-dimensional collagen matrices" Blood, Jul. 9, 2009, vol. 114, No. 2.
Sun, G., et al., "Dextran hydrogel scaffolds enhance angiogenic responses and promote complete skin regeneration during burn wound healing" PNAS, 2011, vol. 108, No. 52.
Sun, G., et al., "Functional neovascularization of biodegradable dextran hydrogels with multiple angiogenic growth factors" Biomaterials 32 (2011) 95e106.
Sun, G., et al., "Functional groups affect physical and biological properties of dextran-based hydrogels" J Biomedical Materials Research Part A, 2010; 93A: 1080-1090.

* cited by examiner

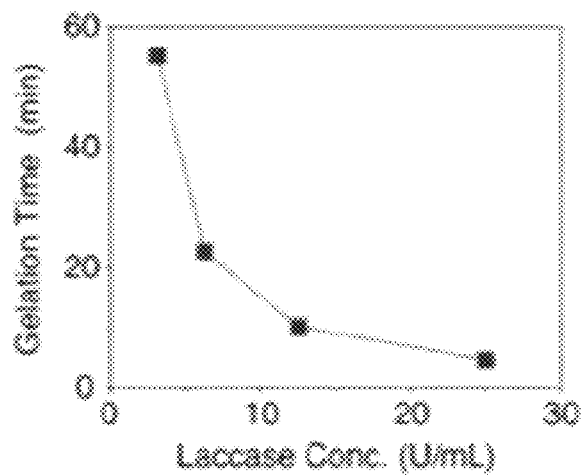 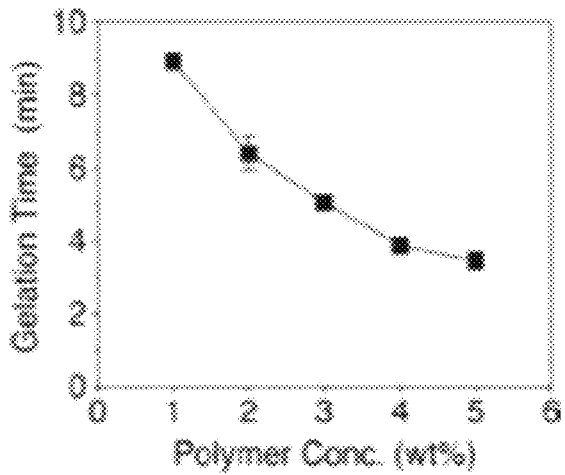
Fig. 6A                    Fig. 6B

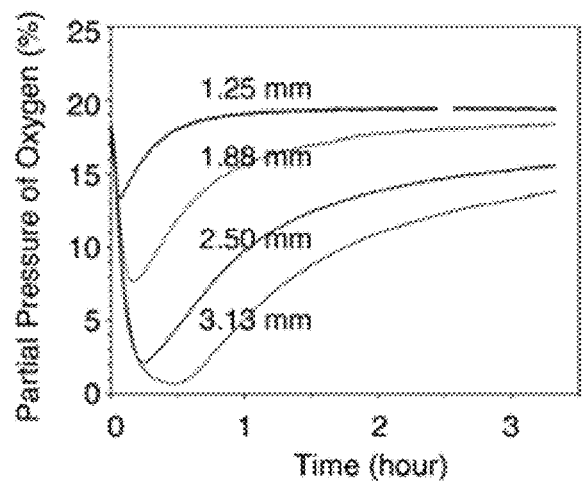
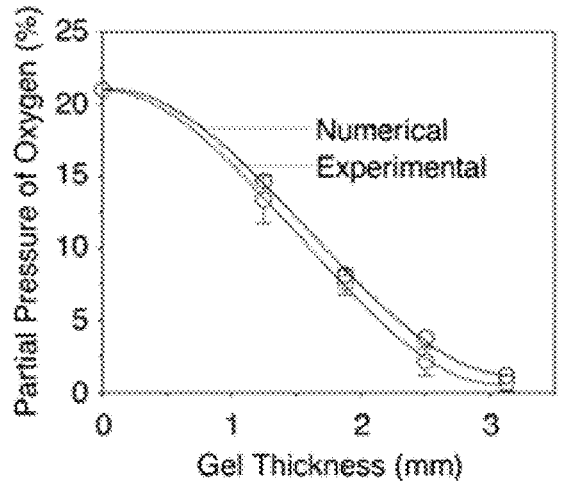
Fig. 10A    Fig. 10B
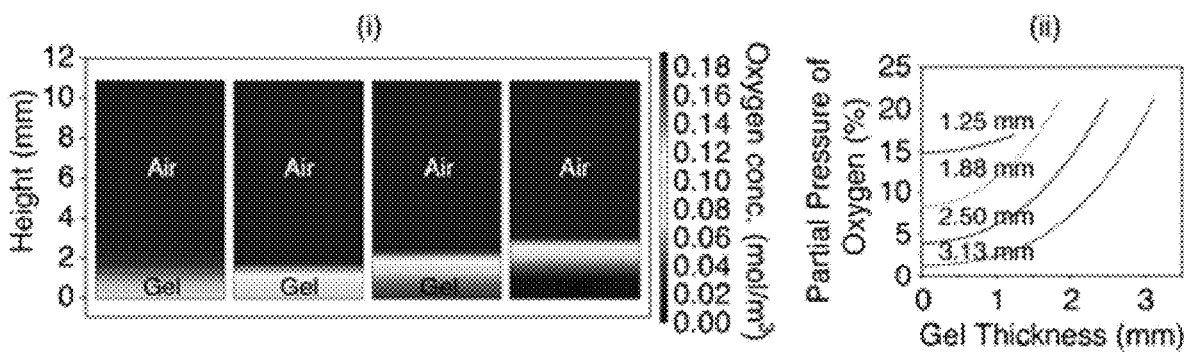
Fig. 10C

METHODS OF INDUCING VASCULAR MORPHOGENSIS

CROSS REFERENCE TO RELATED APPLICATIONS

This application is a Continuation of U.S. patent application Ser. No. 14/536,392, filed Nov. 7, 2014, which claims the benefit of U.S. Provisional Application Ser. No. 61/901,804 filed Nov. 8, 2013, and U.S. Provisional Application Ser. No. 62/054,849 filed Sep. 24, 2014, the entire contents of which are incorporated by reference herein.

This invention was made with government support under grant numbers R01HL107938 and U54CA143868 awarded by the National Institutes of Health, and grant number 1054415 awarded by the National Science Foundation. The government has certain rights in this invention.

FIELD OF INVENTION

This technology is directed to novel hydrogels that can serve as three-dimensional (3D) oxygen-controllable and hypoxia-inducible microenvironments.

BACKGROUND

An emerging paradigm in the mimicry of three-dimensional (3D) microenvironments involves using a variety of bioinspired materials to reconstruct critical aspects of the native extracellular niche (Huebsch et al., Nature, 2009; 462: 426-432; Place, E. S., et al., Nature materials, 2009; 8: 457-470. Synthetic hydrogels have attracted substantial attention as 3D microenvironments owing to their structural similarity to the natural extracellular matrix (ECM) and their tunable properties. (Cushing, M. C., et al., Science, 2007; 316: 1133-1134; Lutolf, M. P. et al., Nature biotechnology, 2005; 23: 47-55; Place, E. S. et al., Nat. Mater. 2009, 8, 457; Annabi, N. et al., Adv. Mater. 2014, 26, 85: Malda, J. et al., Adv. A ater. 2013, 25, 5011: Thiele, J. et al., Adv. Mater. 2014, 26, 125). Researchers have endeavored to develop synthetic hydrogels to recapitulate temporal and spatial complexity in the native ECM, which varies not only in composition, but also in physicochemical parameters, including cell adhesion ligands (Luo, Y., et al., Nature materials, 2004; 3: 249-253), growth factors/cytokines (Martino, M. M., et al., Science translational medicine, 2011; 3: 100ra189), mechanical properties (Engler, A. J., et al., Cell, 2006; 126: 677-689), proteolytic degradability (Lutolf, M. P., et al., PNAS USA, 2003; 100: 5413-5418), and topography (Kilian, K. A., et al., PNAS USA, 2010; 107: 4872-4877). Thus, these studies have established how such parameters individually or synergistically regulate cell behavior.

Oxygen (dioxygen, $O_2$) is vital for the existence of all multicellular organisms, acting as a signaling molecule for cells and regulating their metabolism, survival, cell-to-cell interactions, migration, and differentiation (Semenza, G. L., Science. 2007; 318:62-64; Covello, K. L. et al., Current topics in developmental biology, 2004; 62:37-54). In particular, $O_2$ deprivation (below 5% partial pressure of $O_2$, defined as hypoxia) is an important physiological signal, which presents in the native extracellular matrix (ECM) in various tissues (Simon, M. C. and Keith, B., Nat. Rev. Mol. Cell Biol. 2008, 9, 285; Simon, M. C. and Keith, B., Cell 2007, 129, 465). $O_2$ tension in the mammalian reproductive tract is in the range of 1.5-8% (Fischer, B. and Bavister, B. D., J. Reprod. Fertil. 1993, 99, 673). During embryonic development and adult tissue regeneration and remodeling, cellular differentiation is regulated by generation of hypoxic microenvironments (Semenza, G. L., Trends Mol. Med. 2001, 7, 345). Indeed, hypoxia occurs in pathological conditions, such as tissue ischemia and inflammation as well as in solid tumors (Maltepe, E. and Simon, M. C., J. Mol. Med. 1998, 76, 391). Furthermore, hypoxia is a crucial physiological signal in wound healing and regeneration (LaVan, F. B. and Hunt, T. K., Clin. Plast. Surg. 1990, 17, 463; Du, J. et al., Gene Ther. 2013, 20, 1070). The $O_2$ tension in the wound area decreases due to the disruption of the local microvasculature, which induces acute local hypoxia. Acute hypoxia plays a role as an important physiological signal during all phases of wound healing as it regulates cellular proliferation, migration, and differentiation through the induction of cytokines and diverse intracellular signaling pathways (W. X. Hong, et al., Adv. Wound Care 2014; E. A. O'Toole, et al., J. Clin. Invest. 1997, 100, 2881). To activate downstream signaling pathways and to facilitate accumulation of relevant transcription factors, hypoxic conditions must be maintained for several hours (>1 hour) (D. M. Stroka, et al., FEBS J. 2001, 15, 2445).

Cellular responses to $O_2$ deprivation (hypoxia) are primarily regulated by hypoxia-inducible factors (HIFs) that accumulate under hypoxic conditions and activate the expression of numerous genes that regulate myriad cellular activities (Keith, B. et al., Cell, 2007; 129:465-472). HIFs act as key regulators, promoting angiogenesis during embryonic development, tumor progression, and tissue regeneration (Simon, M. C. et al., Nature reviews: Molecular cell biology, 2008; 9:285-296; Heddleston, J. M. et al., British J Cancer, 2010; 102:789-795; Jopling, C. et al., Circulation, 2012; 126:3017-3027). HIFs regulate the expression of many angiogenic genes that promote vascular differentiation and morphogenesis, such as vascular endothelial growth factor (VEGF), vascular endothelial growth factor receptor 2 (VEGFR2) (Ferrara, N., et al., Nature medicine, 2003; 9:669-676; Lee, Y. M. et al., Developmental dynamics, 2001; 220:175-186; Gassmann, M. et al., PNAS USA, 1996; 93:2867-2872), angiopoietin 1 (ANG1) (Augustin, H. G. et al., Nature reviews. Molecular cell biology 2009; 10:165-177), as well as matrix metalloproteinases (MMPs) (Fong, G. H., Journal of molecular medicine, 2009; 87:549-560; Manalo, D. J. et al., Blood, 2005; 105:659-669; Ottino, P. et al., Molecular vision, 2004; 10:341-350; Pugh, C. W. et al., Nature medicine, 2003; 9:677-684; Ben-Yosef, Y. et al., Circulation research, 2002; 90:784-791). Hypoxia, low oxygen tension, plays a pivotal role during development, regeneration, and cancer. Although hypoxia is an important factor in vascular development, hypoxia has not been simulated in a 3D microenvironment. The present invention addresses the need for fundamental technology and materials that can serve as 3D hypoxic microenvironments.

SUMMARY OF THE INVENTION

As embodied and fully described, the present invention relates to compositions, systems and methods to mimic in vivo microenvironments. In an embodiment, the composition is a hydrogel that can regulate cellular activities or cellular differentiation in vitro through unique properties of the hydrogel, such as control of oxygen within the gel, in the absence of external bioactive molecules such as growth factors or cytokines. In a preferred embodiment, the hydrogel is an oxygen controllable and hypoxia-inducible hydrogel (HI hydrogel). In an embodiment, the HI hydrogel stimulates vascular differentiation and morphogenesis in vitro through the activation of hypoxia-inducible factors (HIFs) and upregulation of the related gene expression. In another embodiment, the HI hydrogels have an ability to promote blood vessel recruitment and infiltration via the materials/tissue interface in vivo without additional bioactive molecules. Moreover, this approach can be adapted for many other natural or synthetic polymers for a broad range of applications, including treatment of vascular disorders, generation of artificial tissue constructs using progenitor or stem cells in regenerative medicine, and development of engineered such de novo disease models as in vitro cancer models.

An embodiment of the invention is a composition comprising a phenolic agent and a polymer. In embodiments, the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. In embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In a further embodiment, the phenolic agent is conjugated with the polymer. In embodiments of the invention, the phenolic agent conjugated with the polymer is crosslinkable or polymerizable. In a preferred embodiment, the phenolic agent conjugated with the polymer backbone are cross-linked.

Another embodiment of the invention is a hydrogel comprising a phenolic agent and a polymer. In embodiments, the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. In embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In a further embodiment, the phenolic agent is conjugated with the polymer. In embodiments of the invention, the phenolic agent conjugated with the polymer is crosslinkable or polymerizable. In a preferred embodiment, the phenolic agent conjugated with the polymer backbone are cross-linked. In preferred embodiments, the hydrogel is oxygen-controllable and hypoxia-inducible.

In another embodiment of the invention, a hydrogel is prepared by crosslinking a phenolic agent conjugated polymer backbone. In preferred embodiments the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. In another preferred embodiment, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In embodiments, the cross-linking may be via enzymatic reaction. In an embodiment, the enzymatic reaction uses enzymes such as laccase or tyrosinase. Embodiments relate to a hydrogel formed that is oxygen-controllable and hypoxia-inducible (the hydrogel induces hypoxia).

Other embodiments of the invention relate to a method of preparing a hydrogel. In some embodiments, the hydrogel is prepared by crosslinking a phenolic agent polymer conjugate. In embodiments, the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. In some embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In embodiments, crosslinking may be achieved by any cross-linking method. In an embodiment, cross-linking comprises enzymatic reaction. Preferably, the enzymatic reaction uses an enzyme selected from laccase and tyrosinase. In embodiments, the hydrogel is oxygen-controllable and hypoxia-inducible. In a preferred embodiment, the hydrogel induces hypoxia.

Yet another embodiment relates to a method of preparing an oxygen-controllable and hypoxia inducible hydrogel comprising selecting a phenolic agent and a polymer; cross-linking the phenolic agent and the polymer, wherein the cross-linking comprises an enzymatic reaction using an enzyme selected from laccase and tyrosinase, and forming a hypoxia-inducible hydrogel. In embodiments, the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. In other embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In some embodiments, the hydrogel further comprises cells. In embodiments, the hydrogel is oxygen-controllable and hypoxia-inducible. In preferred embodiments, the hydrogel induces hypoxia.

In another embodiment, the invention relates to a method of forming a three-dimensional microenvironment comprising a hydrogel. In embodiments of the invention, the hydrogel is formed by crosslinking of a phenolic agent conjugated polymer. In preferred embodiments, the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. In other preferred embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In embodiments, crosslinking may be achieved by any cross-linking method. In an embodiment, cross-linking comprises enzymatic reaction. Preferably, the enzymatic reaction uses an enzyme such as laccase or tyrosinase. In some embodiments, the hydrogel further comprises cells. In an embodiment, the hydrogel is oxygen-controllable and hypoxia inducible. In a further embodiment, the hydrogel is a hypoxia-inducing hydrogel.

In other embodiments, the invention relates to a three-dimensional microenvironment comprising a hydrogel. In certain embodiments the hydrogel comprises a phenolic agent and a polymer. In embodiments, the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. In other embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In a further embodiment, the phenolic agent is conjugated with the polymer. In embodiments of the invention, the phenolic agent conjugated with the polymer is crosslinkable or polymerizable. In a preferred embodiment, the phenolic agent conjugated with the polymer backbone are cross-linked. In some embodiments, the hydrogel further comprises cells. In embodiments, the hydrogel is oxygen-controllable and hypoxia-inducible. In a further embodiment, the hydrogel is a hypoxia-inducing hydrogel.

In the embodiments of the invention, the phenolic agent is selected from ferulic acid (FA), tyramine, 4-Hydroxyphenylacetic acid, 3-(4-Hydroxyphenyl)propionic acid, Dopamine, Norepinephrine, epinephrine, and their derivatives. Preferably, the phenolic agent is ferulic acid (FA) or tyramine (TA). In the embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. In preferred embodiments, the polymer is gelatin or dextran. Crosslinking may be achieved by any cross-linking method, including ionic crosslinking, ultraviolet crosslinking, enzymatic crosslinking, and chemical crosslinking reaction. In the embodiments of the invention, crosslinking is achieved by enzyme-mediated reaction using enzymes, such as, for example, laccase or tyrosinase.

Embodiments of the invention relate to an oxygen controllable, hypoxia-inducible hydrogel that comprises cells or tissue. The cells may be selected from pluripotent stem cells, adult stem cells, fibroblasts, endothelial colony-forming cells, human umbilical vein endothelial cells (HUVECs) and cancer cells. The tissue may be tumor tissue. In some embodiments, the cells or tissue are encapsulated within the hydrogel. In preferred embodiments, the encapsulated cells or tissue stimulate vascular tube formation or induce cancer cell fate decisions, such as proliferation and spheroid formation. In preferred embodiments, the hydrogel is oxygen-controllable and hypoxia-inducible (induces hypoxia). Other preferred embodiments relate to hydrogels that induce hypoxic conditions in vivo. The oxygen controllable and hypoxia-inducible hydrogels may induce blood vessel recruitment into the hydrogel.

Other embodiments of the invention relate to an oxygen controllable, hypoxia-inducible hydrogel and methods that induce vascular morphogenesis. One such embodiment is a system for inducing vascular morphogenesis comprising a phenolic agent and a polymer, a crosslinking agent for generating hypoxia-inducing hydrogel, and cells or tissue for stimulating vascular tubulogenesis. In some embodiments, the phenol agent is ferulic acid (FA), tyramine, 4-Hydroxyphenylacetic acid, 3-(4-Hydroxyphenyl)propionic acid, Dopamine, Norepinephrine, or epinephrine, or their derivatives. In embodiments, the polymer is a natural or synthetic polymer selected from collagen, gelatin, chitosan, heparin, fibrinogen, hyaluronic acid, chondroitin sulfate, pullulan, xylan, dextran, and polyethylene glycol as well as their derivatives. The cells may be selected from pluripotent stem cells, adult stem cells, fibroblasts, endothelial colony-forming cells, human umbilical vein endothelial cells (HUVECs) and cancer cells, and the tissue may be tumor tissue.

BRIEF DESCRIPTION OF THE DRAWINGS

FIG. 1A Schematic representation of GtnFA HI hydrogel formation. HI hydrogels are formed via laccase-mediated dimerization of FA molecules with oxygen consumption. Laccase catalyzes the four-electron reduction of molecular oxygen to water molecules, resulting in oxidation of FA molecules to form diferulic acid (DiFA), crosslinking the polymer networks.

FIG. 3A 1H NMR spectra of GtnFA (red) and Gtn (blue) (300 MHz, D$_2$O, 25° C.): a, δ6.48 (d, 1H); b, δ7.45 (d, 1H); c, δ7.16 (d, 1H); d, δ6.99 (d, 1H); e, δ6.89 (d, 1H). FIG. 3B UV-Vis spectra of GtnFA synthesized with different FA feed amount (0.0-4.0 mmol) in aqueous solutions at 25° C.

FIGS. A4-4B: Crosslinking chemistry.

FIGS. 6A-6B: Gelation time control for GtnFA HI hydrogel. FIG. 6A Effect of laccase concentration on gelation time. FIG. 6B Effect of polymer concentration on gelation time. Results are shown as the average values±SD (n=3).

FIG. 7A Effect of collagenase concentration on proteolytic degradation of the hydrogels. FIG. 7B Effect of polymer concentration on degradability. Results are shown as the average values±SD (n=3).

FIG. 8A In vitro toxicity graphs of (i) GtnFA conjugate and (ii) laccase on fibroblasts, quantified by an XTT cell proliferation assay. The results are shown as the average values±standard deviation (n=5). FIG. 8B Fluorescence microscope images of fibroblast embedded in the hydrogels stained with calcein-AM (green, live)/ethidium homodimer (red, dead) live/dead assay 2 and 24 hours after encapsulation, demonstrating cytocompatibility of GtnFA HI hydrogels; 3 wt % hydrogels formed with 10 U/mL of laccase after 2 hours (live cells, 97.7±1.2%; dead cells, 2.27±1.2%) and 24 hours (live cells, 91.2±1.9%; dead cells, 8.8±1.2%), and 3 wt % hydrogels formed with 25 U/mL of laccase after 2 hours (live cells, 95.8±1.9%; dead cells, 4.2±1.9%) and 24 hours (live cells, 91.5±3.2%; dead cells, 8.5±3.2%). FIG. 8C Light microscope images of fibroblasts encapsulated in GtnFA HI hydrogel and cultured up to 10 days, showing cell spreading and elongation within the hydrogel matrices. Scale bars are 100 μm. The results are shown as the average values±SD (n=3).

FIG. 9A Effect of laccase concentration (6.3-25.0 U/mL). FIG. 9B Effect of degree of substitution (DS) of FA (13-45 μmol/g of polymer). FIG. 9C Effect of culture media (100-200 μL).

FIGS. 10A-10D: Controlling and predicting DO levels in GtnFA HI hydrogel matrix. FIG. 10A Measured DO levels in GtnFA HI hydrogels (3 wt %, DS 45, and 25 U/mL laccase) as a function of time demonstrate the effect of hydrogel thickness (1.25-3.13 mm) on GtnFA HI hydrogel DO levels. FIG. 10B Model prediction of $DO_{min}$ at the bottom of the GtnFA HI hydrogels. Model numerical prediction (blue symbols) compared to the measured values (red symbols) confirm the reliability of the given parameters; FIG. 10C Model predictions of DO levels and gradients after 30 min of hydrogel formation (i) in the two-layer model (air-hydrogel) and (ii) across HI hydrogels, depending on different thicknesses. FIG. 10D Model predictions of DO levels and gradients after 30 min of hydrogel formation (i) in the three-layer model (air-media-hydrogel) and (ii) across the HI hydrogels with the culture media.

FIG. 12A Schematic of vascular tube formation using GtnFA HI hydrogels. In response to self-generated hypoxic environment, HIF pathways are activated and enable ECFCs tubulogenesis to form complex and comprehensive vascular networks. FIG. 12B Vascular tube morphogenesis by ECFCs within the GtnFA HI hydrogels. (i) Light micrographic images of ECFCs encapsulated within GtnFA HI hydrogels during three days of culture. Quantitative analysis of vascular tube formation shows: (ii) mean tube coverage, (iii) tube length, and (iv) tube thickness. FIG. 12C Confocal microscopic images of ECFCs encapsulated within (i) nonhypoxic gel and (ii) hypoxic gel; (iii) confocal z-stacks and orthogonal sections show lumen formation (indicated by arrows) within the vascular networks (phalloidin in green; nuclei in blue). FIG. 12D Real time RT-PCR analysis of gene expression of ECFCs encapsulated within the different hydrogel types: (i) HIFs, (ii) angiogenic genes, and (iii) MMP genes. FIG. 12E Inhibition of vascular morphogenesis of ECFCs by siRNA suppression. (i) Fluorescence microscopic images after three days in culture show that siRNA suppression of HIF-1α and/or HIF-2α affect the vascular morphogenesis. Quantitative analysis of vascular tube formation shows: (ii) mean tube coverage and (iii) tube length. (iv) Real time RT-PCR analysis of MT1-MMP gene expression of ECFCs treated with HIF-1a and/or HIF-2α siRNA and encapsulated within the HI gel after 24 h of culture (iv). Significance levels were set at: *p<0.05, p<0.01, and *p<0.001. Values shown are mean SD. Scale bars are 50 m (FIG. 12B and FIG. 12C) and 100 m (FIG. 12E).

FIG. 13A DO levels of GtnFA HI hydrogels encapsulated with 2×106 cell/mL of ECFCs as a function of hydrogel thickness (hypoxichydrogel thickness, 2.5 mm; nonhypoxic hydrogel thickness, 1.25 mm). FIG. 13B Magnified plot of the DO level of hypoxic hydrogel (<3.00/% $O_2$).

FIG. 15A Zymographic analysis shows more activated MMP-1 and MMP-2 in media of ECFCs cultured within GtnFA hypoxic hydrogels than within nonhypoxic hydrogels. FIG. 15B Western blot analysis reveals higher levels of MT1-MMP extracted from ECFCs encapsulated within GtnFA hypoxic hydrogels than within nonhypoxic hydrogel.

FIG. 16A Vascular tube morphogenesis within GtnFA hydrogels, with or without media changes, over the three days of culture. FIG. 16B Quantitative analysis of vascular tube formation in the two conditions showing (i) mean tube coverage, (ii) tube length, and (iii) tube thickness. Values shown are means±SD. Significance levels were set at: *p<0.05, p<0.01, and *p<0.001. Scale bars are 50 μm.

FIG. 19A Schematic representation of blood vessel invasion into acute hypoxic environment generated by in situ hydrogel formation with oxygen consumption. FIG. 19B Model prediction of the oxygen levels 30 min after injection. FIG. 19C (i) H&E-stained sections of hydrogels one and three days after transplantation and (ii) quantification of the granulation layer thickness. FIG. 19D (i) a-SMA-stained section of hydrogels one and three days after transplantation and (ii) quantification of blood vessels surrounding and penetrating into the hydrogels. M, Muscle; H, hydrogels. The yellow dotted line represents the granulation layer between muscle and hydrogel. Arrows indicate blood vessel structures within the hydrogels. Significance levels were set at: *p<0.05, p<0.01, and *p<0.001. Values shown are mean SD. Scale bar is 100 m and 50 m (insets).

FIG. 24B Fluorescence microscopic images of KP cells stained with calcein (live cell, green) and ethidium bromide homodimer-1 (ethD-1; dead cell, red) after 7 days.

FIG. 25A Light microscope images of tumor outgrowth toward hydrogel matrices after 2 weeks. FIG. 25B H&E images of cross-sectioned hydrogels encapsulated with tumor tissues after 2 weeks. T, tumor tissue; G, hydrogel.

FIG. 27A DexE, FIG. 27B PEG-$(PNC)_2$, and FIG. 27C DexE-PT (300 MHz, $D_2O$, 25° C.): a, δ4.95 ppm (anomeric protons of dextran repeating units); b, δ2.70 ppm (methylene protons of BEAHB); c-d, δ7.35-8.25 ppm (aromatic protons of PNC molecules); e, δ3.4-3.8 ppm (methylene protons of PEG repeating units); f-g, δ6.8-7.2 ppm (aromatic protons of TA).

FIG. 29A Viscoelastic modulus (G2, filled symbols; G3, open symbols) of Dex-HI hydrogels with dynamic time sweep. The rheological analysis shows dynamic network formation of Dex-HI hydrogels with different polymer concentrations; (i) Dex-HI3, (ii) Dex-HI5, and (iii) Dex-HI10. FIG. 29B Dynamic time sweep at the equilibrium swelling state of hydrogels. The viscoelastic measurements exhibit the tunable mechanical properties of the Dex-HI hydrogels (Dex-HI3, 110 Pa; Dex-HI5, 450 Pa; Dex-HI10, 1840 Pa) by varying polymer concentrations. FIG. 29C Dynamic frequency sweep at the equilibrium swelling state of hydrogels, showing hydrogel network stability after gelation.

FIG. 30A In vitro cytotoxicity graphs of DexE-PT polymer; (i) proliferation and (ii) viability of HUVECs up to day 3, quantified by a WST-1 cell proliferation assay kit. The results are shown as the average values±SD (n=5). FIG. 30B Light microscope images of HUVECs cultured with or without DexE-PT polymer up to day 3, showing the similar cell morphology. Scale bars are 100 μm.

FIG. 31A DO levels at the bottom of Dex-HI hydrogels (3-10 w/v %, 3.13 mm thickness, and 25 U mL$^{-1}$ laccase) as a function of time. FIG. 31B Model prediction of DO levels at the bottom of hydrogels with different polymer concentrations; (i) Dex-HI3, (ii) Dex-HI5, and (iii) Dex-HI10. $O_2$ consumption rate of laccase-mediated crosslinking reactions follows Michaelis-Menten equation. FIGS. 31C-31E Model prediction and computer simulation of DO levels and gradient. We compared model numerical prediction (open symbols) and the experimental values (filled symbols) to confirm the reliability of the given $V_{max}$ and $K_m$ values; FIG. 31C(i) Dex-HI3, FIG. 31D(i) Dex-HI5, and FIG. 31E(i) Dex-HI10. Simulation of DO gradient within the hydrogels in the two-layer model (air-hydrogel) as a function of time; FIG. 31C(ii) Dex-HI3, FIG. 31D(ii) Dex-HI5, and FIG. 31E(ii) Dex-HI10.

FIG. 32A Model prediction of DO gradient at different time points in physiological in vivo conditions ($pO_2$, 40 mmHg): (i) after 10 minutes of injection (DO levels of the hydrogel core, 4.3×10$^{-2}$ mol m$^{-3}$; DO levels of the interface, 4.5×10$^{-2}$ mol m$^{-3}$), (ii) after 30 minutes of injection (DO levels of the hydrogel core, 1.6×10$^{-2}$ mol m$^{-3}$; DO levels of the interface, 3.6×10$^{-2}$ mol m$^{-3}$); (iii) after 8 hours of injection (DO levels of the hydrogel core, 1.6×10$^{-2}$ mol m$^{-3}$; DO levels of the interface, 3.6×10$^{-2}$ mol m$^{-3}$). FIG. 32B Model prediction of DO gradients within the Dex-HI hydrogels after 1 hour of injection in physiological in vivo conditions ($pO_2$, 40 mmHg) depending on their shape: (i) ellipse, (ii) rectangle, and (iii) polygonal shapes. FIG. 32C DO gradients of the ellipse-shaped Dex-HI hydrogels after 1 hour of injection in different $pO_2$ environments: (i) 40 mmHg (DO levels of the hydrogel core, 1.6×10$^{-2}$ mol m$^{-3}$; DO levels of the interface, 3.4×10$^{-2}$ mol m$^{-3}$), (ii) 20 mmHg (DO levels of the hydrogel core, 7.8×10$^{-3}$ mol m$^{-3}$; DO levels of the interface, 1.8×10$^{-2}$ mol m$^{-3}$), and (iii) 10 mmHg (DO levels of the hydrogel core, 3.7×10$^{-3}$ mol m$^{-3}$; DO levels of the interface, 9.0×10$^{-3}$ mol m$^{-3}$).

DETAILED DESCRIPTION OF THE INVENTION

Figure 1A:
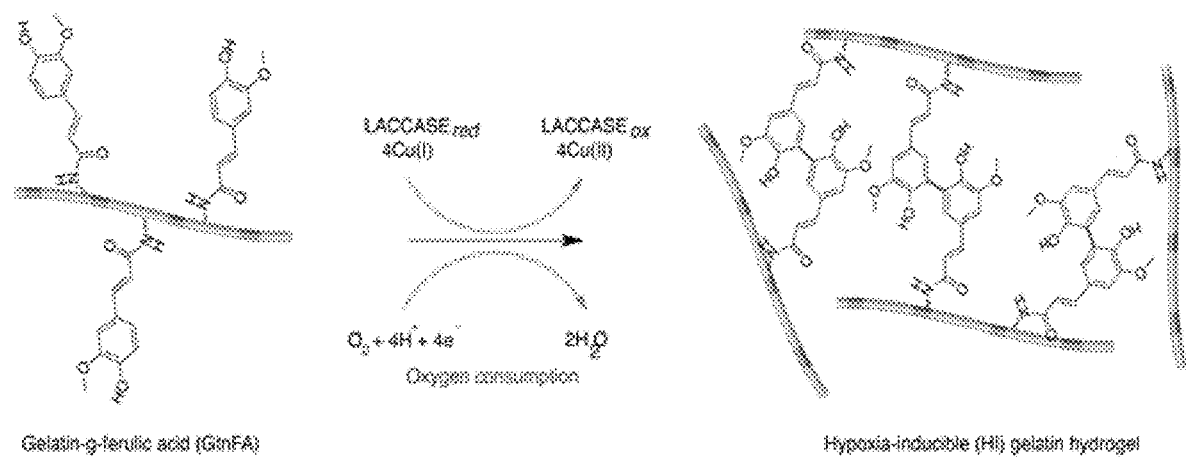
FIGS. 1A-IC: Gelatin-g-ferulic acid (GtnFA) Hypoxia-inducible (HI) hydrogel synthesis, network formation kinetics, and cytocompatibility.

A new class of oxygen controllable, hypoxia-inducible hydrogels (HI hydrogel) materials that can serve as three dimensional (3D) hypoxic microenvironments is disclosed. Dissolved oxygen (DO) levels and gradients in the HI hydrogel can be controlled and precisely predicted, with prolonged hypoxic conditions induced. The HI hydrogel matrix can, for example, stimulate tubulogenesis of endothelial colony-forming cells (ECFCs) and cancer cell activities by activating HIFs, and promotes rapid neovascularization from the host. In addition, this is the first hydrogel material with precisely prolonged and controlled intramural DO levels and gradients, which is a new class of biomaterials for a wide range of in vitro and in vivo applications.

Hypoxia, or low oxygen, plays a pivotal role during cellular and tissue development and regeneration. Although hypoxia is an important factor in vascular development, hypoxia has not been simulated previously in a 3D microenvironment. In an embodiment of the invention, a hypoxia-inducible (HI) hydrogel is disclosed. HI hydrogels are hydrogels formed with concomitant oxygen consumption.

Conjugating a phenolic agent to a polymer backbone can be used to produce a HI hydrogel by consuming oxygen ($O_2$) in enzyme-mediated reactions. Though many fields have explored such reactions, e.g., food chemistry and biosensors (Rosana, C. M. et al., *Trends in Food Science & Technology*, 2002; 13:205-216), derived from phytochemistry, they have not been used to fabricate oxygen controllable biomaterials.

Throughout the disclosure, the terms phenolic agents, phenolic molecules, and phenol molecules are used interchangeably. As used herein, the term "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate.

HI hydrogels of the invention can be generated with various phenolic agents (phenol molecules), such as ferulic acid (FA), tyramine (TA), 4-Hydroxyphenylacetic acid, 3-(4-Hydroxyphenyl)propionic acid, Dopamine, Norepinephrine, epinephrine, and their derivatives. Such phenolic agents include the structures in Table 1.

TABLE 1

Phenolic Agents

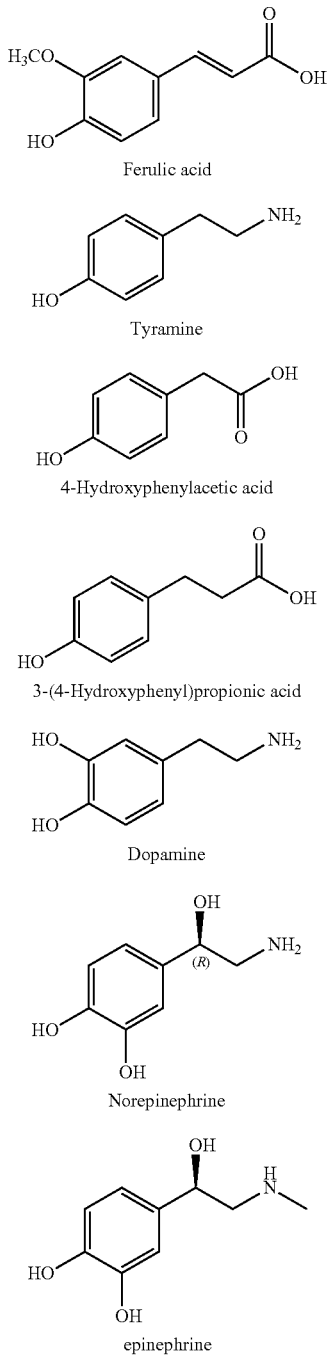

Ferulic acid

Tyramine

4-Hydroxyphenylacetic acid 3-(4-Hydroxyphenyl)propionic acid

Dopamine

Norepinephrine epinephrine

The novel HI hydrogels can be generated from natural or synthetic polymers as the polymer backbone. Examples of natural or synthetic polymers include collagen, gelatin, chitosan, heparin, fibrinogen, hyaluronic acid, chondroitin sulfate, pullulan, xylan, dextran, and polyethylene glycol as well as their derivatives. Gelatin (Gtn) is one preferred polymer backbone due to its cell-response properties, including cell adhesion and proteolytic degradability, which are critical in vascular morphogenesis (Hanjaya-Putra, D. et al., *Blood,* 2011; 118:804-815; Davis, G. E. et al., *Circulation research,* 2005; 97:1093-1107). Gtn provides relatively simple functionalization with for example, FA, for the formation of intramural hypoxia for both in vitro and in vivo vascular inductions. Dextran is a further preferred polymer backbone, used in conjunction with a hydrophilic linker such as polyethylene glycol (PEG) due to modifiability, bioactivity and hydrophilicity, as well as the similarity of the properties to those of various soft tissues. The high content of hydroxyl functional groups in the Dex molecule allows the Dex to be converted or modified easily with other molecules. A chain of Dex polymer includes three hydroxyl groups per repeat unit, which can allow for a high degree of substitution (DS) of target molecules (Jin, R. et al., *Biomaterials* 2007, 28, 2791). In addition, Dex has excellent water solubility that enables easy control of the precursor solutions. Some polymers may incorporate adhesion sites, such as Arg-Gly-Asp, and additional degradability features, such as MMP-sensitive peptides, depending on the application (Cuchiara, M. P. et al., *Advanced functional materials,* 2012; 22:4511-4518; Khetan, S. et al., *Nature materials,* 2013; 12:458-465; DeForest, C. A. et al., *Nature materials,* 2009; 8:659-664).

Figure 2:
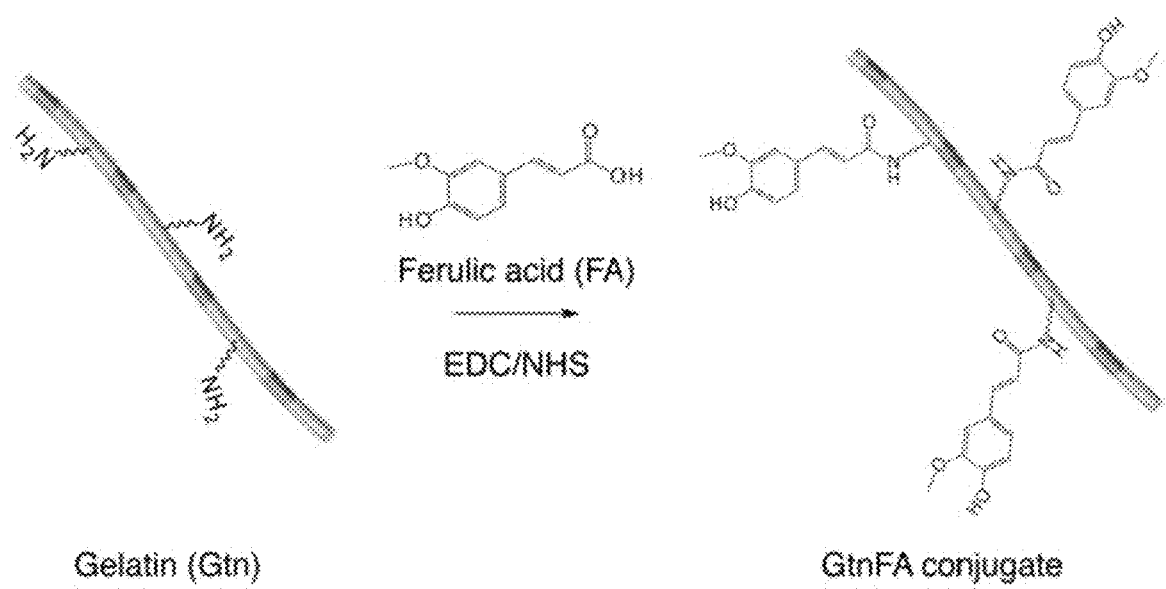
FIG. 2: Synthetic route of gelatin-g-ferulic acid (GtnFA) conjugates. GtnFA conjugate was synthesized by carbodiimide-mediated conjugating reaction. The carboxyl groups of the FA molecules were activated using EDC/NHS and then conjugated to primary amine groups in the gelatin backbone.
Figure 26:
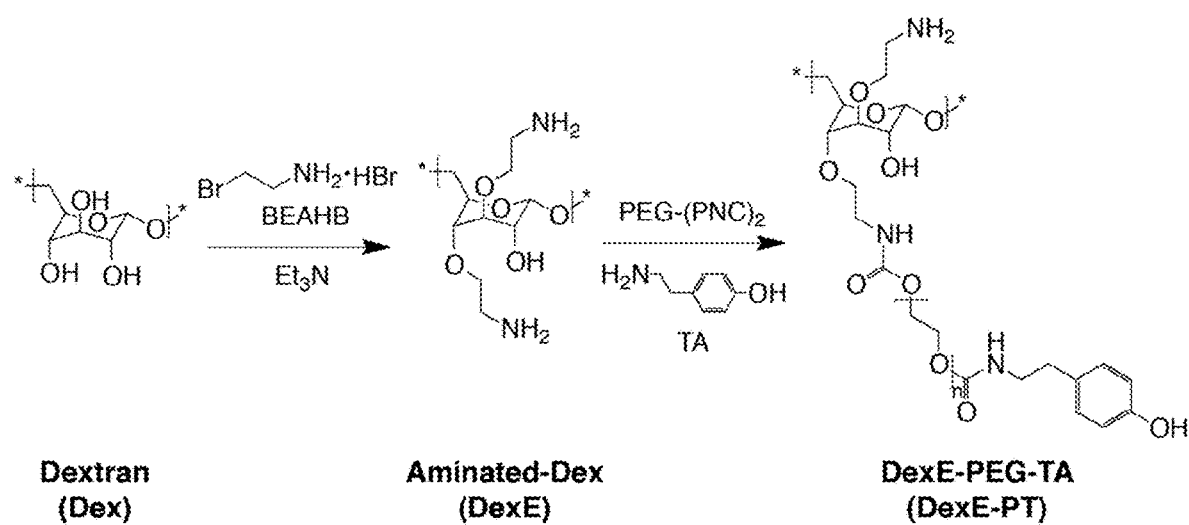
FIG. 26: Synthesis of aminated Dextran-polyethylene glycol-tyramine. Aminated Dextran (DexE)-polyethylene glycol (PEG)-tyramine (DexE-PT) was synthesized by conjugating tyramine (TA) to DexE polymer backbone using PEG as a linker. The amine reactive PEG (PEG-$(PNC)_2$) conjugates each primary amine group of the DexE and TA molecules.

In an embodiment of the invention, functionalized polymers are synthesized by coupling a phenolic agent to a polymer. In a preferred embodiment, carboxyl groups of FA are coupled to amine groups of Gtn to form GtnFA conjugates via a carbodiimide-mediated reaction (FIG. 2). In another embodiment, DexE-PT conjugates were generated by conjugating primary amine groups of TA and aminated-Dex (DexE) using amine reactive PEG molecules (PEG-$(PNC)_2$) to give DexE-PEG-TA (DexE-PT) (FIG. 26). TA molecules were conjugated to Dex using PEG as a linker to enhance crosslinking reactivity. Following the Gtn-HI hydrogel synthesis procedure, Dex-HI hydrogels were generated by conjugating ferulic acid (FA) to the Dex polymer backbone (DexFA) without the PEG linker. Those hydrogels, however, did not exhibit a phase transition from sol to gel during the laccase-mediated chemical reaction, even though Dex-FA exhibited a higher DS of FA (120.2±0.7 μmol/g of polymer, DS120) compared to Gtn-FA molecules (44.70±0.5 μmol/g of polymer, DS45). The molecular structure of the Dex polymer may have affected the phase transition, as Dex has a relatively low molecular weight (~70 kDa) compared to Gtn molecular weight (~100 kDa) and decreased molecular mobility due to its more complex, branched molecular structure. The decreased molecular mobility of the Dex polymer may affect the crosslinking reaction and gel formation. Thus, PEG was used as a hydrophilic linker between the Dex polymer backbone and the TA molecules to improve crosslinking reactivity (Park, K. M. et al., *J. Mater. Chem.* 2011, 21, 13180).

Figure 27A:
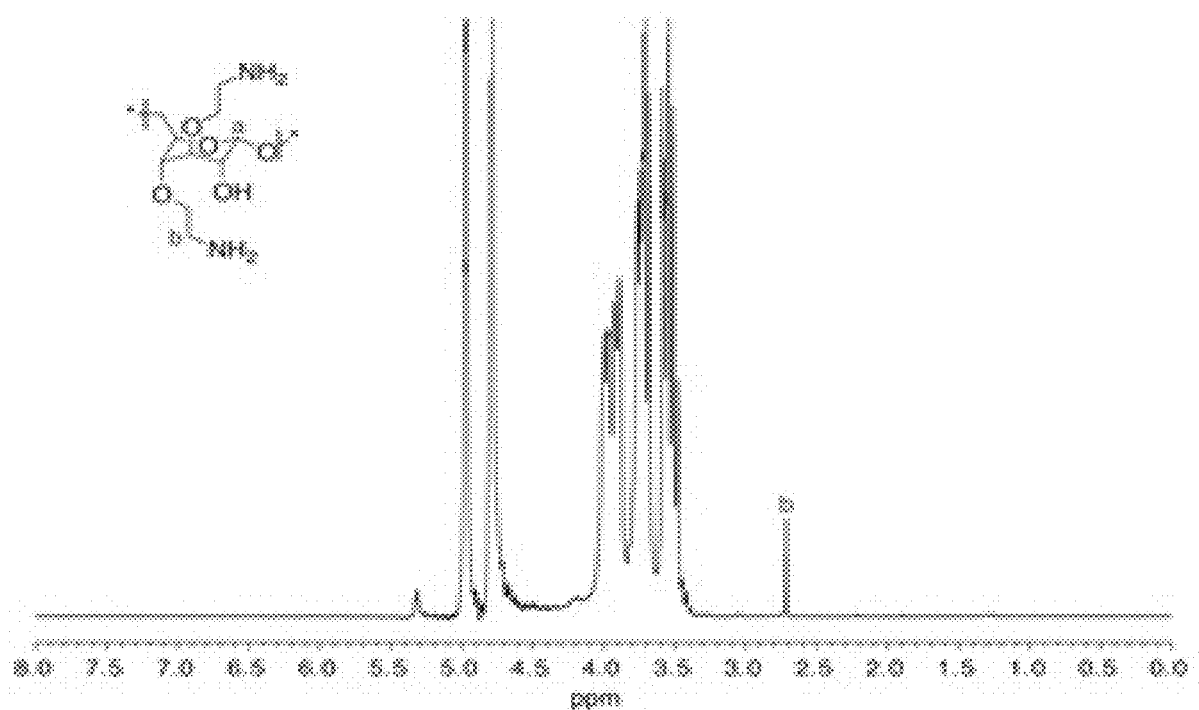
FIGS. 27A-27C: $^1$H NMR of synthesized polymers.
Figure 27B:
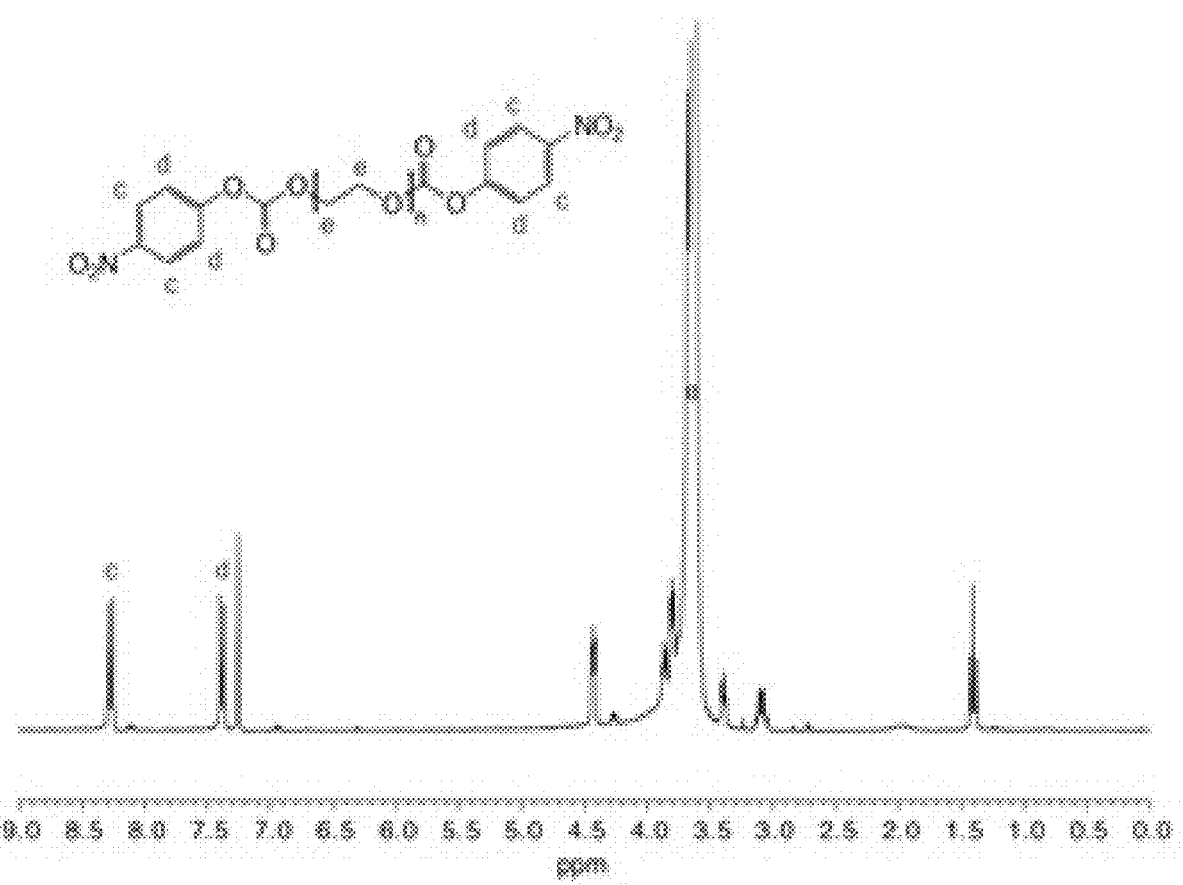
Figure 27C:
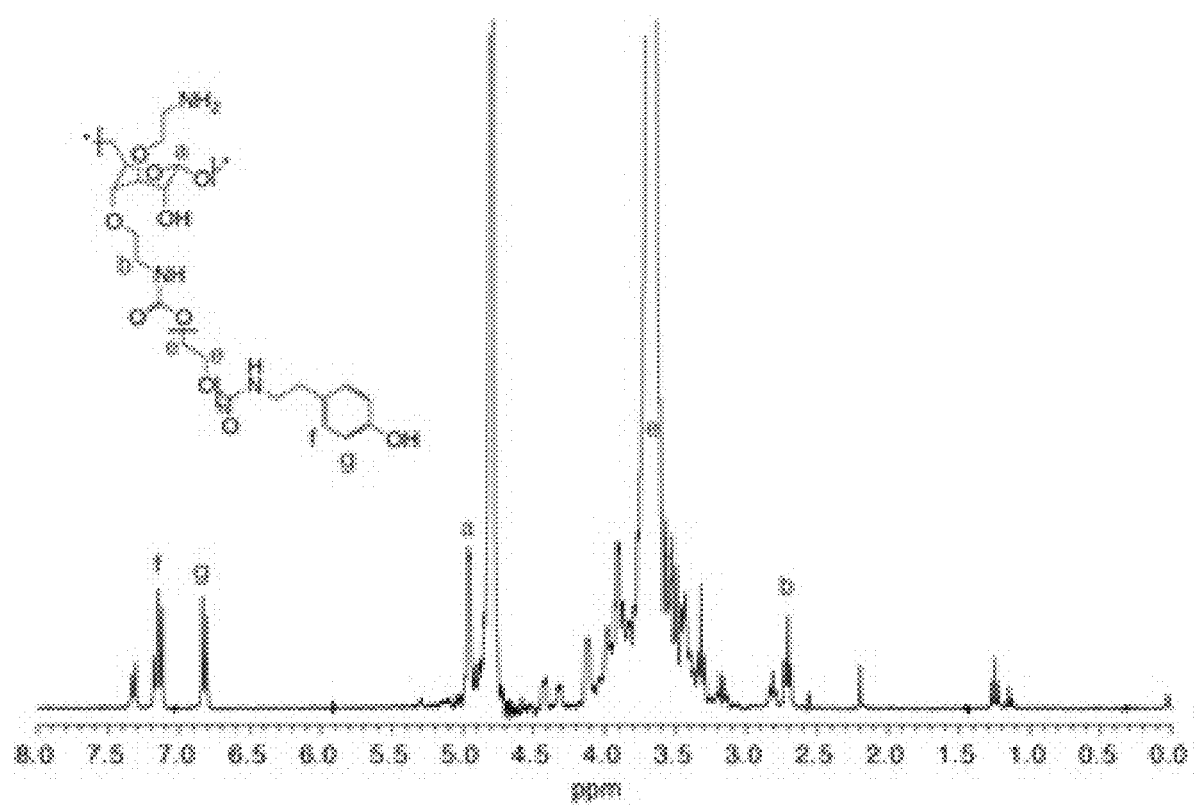

The chemical structure of the functionalized polymer may be characterized using $^1$H NMR. The $^1$H NMR spectra of the functionalized polymers indicates specific peaks of anomeric carbon and alkyl protons of Gtn, and the aromatic protons of FA (FIG. 3A), as well as the specific peaks of aromatic protons of TA (300 MHz, $D_2O$, δ6.8-7.2 ppm), the methylene protons of PEG repeating units (300 MHz, $D_2O$, δ3.4-3.8 ppm), and the anomeric protons of dextran repeating units (300 MHz, $D_2O$, δ4.95 ppm) (FIGS. 27A-27C). UV/VIS spectroscopy was used to determine the degree of substitution (DS) of the phenol molecule. The DS in the GtnFA HI hydrogel may be in the range from about 13 to about 45 μmol FA/g of polymer (FIG. 3B), and in the DexE-PT hydrogel about 170 μmol TA/g of polymer. Thus, the DS in the GtnFA HI hydrogel is from about 13 to about 45. The DS of the DexE-PT HI hydrogel is about 100 to about 350, preferably about 100 to about 200, more preferably about 170. Use of a lower feed amount of phenolic molecules (0.8 mmol of TA) for Dex-HI compared to that for Gtn-HI hydrogels (4.0 mmol of FA), resulted in higher phenolic content of Dex-HI (170.8±4.6 μmol/g of polymer) than that of Gtn-HI (44.70±0.5 μmol/g of polymer). This may be due to the high content of functional groups in the Dex-HI.

Figure 4A:
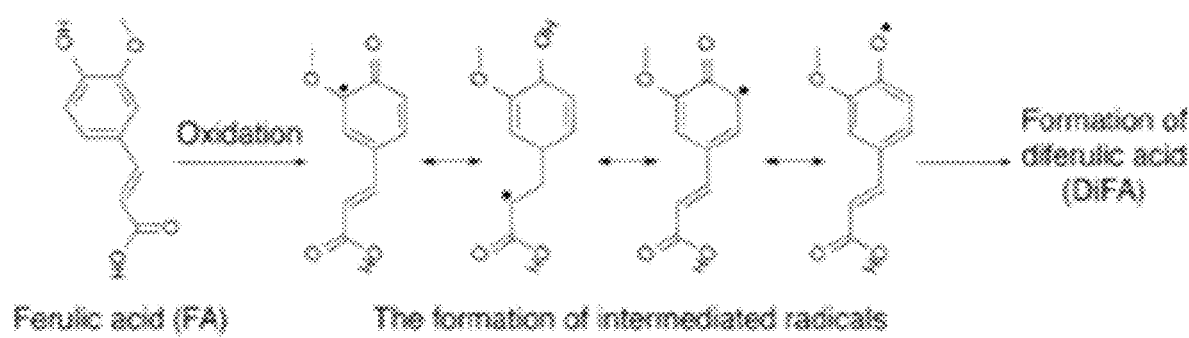
FIG. 4A Laccase-mediated oxidation of FA and the formation of intermediate free radicals to induce diferulic acid (DiFA) formation.
Figure 4B:
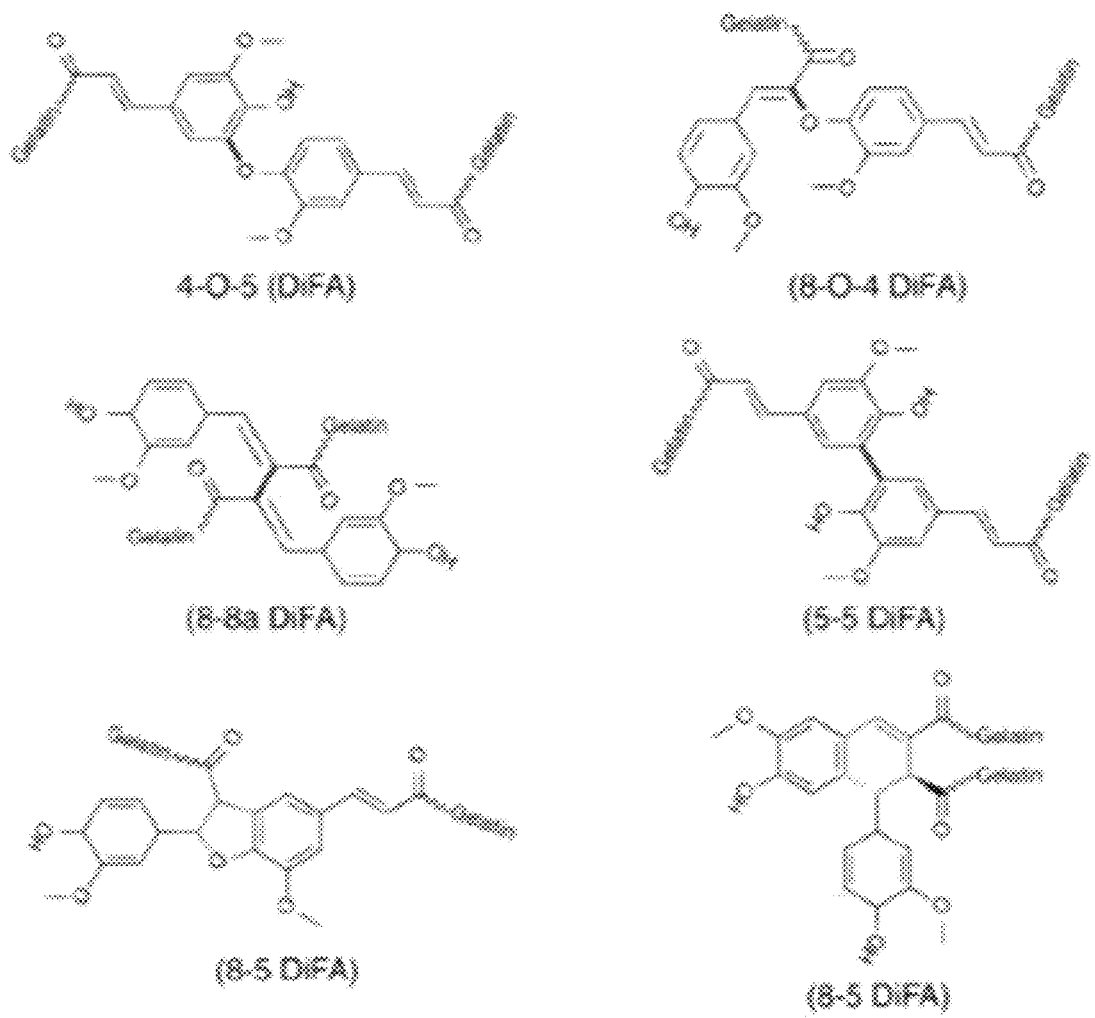
FIG. 4B Different chemical structures of DiFA may be used to crosslink GtnFA polymer chains. Newly formed chemical structures are indicated.
Figure 28:
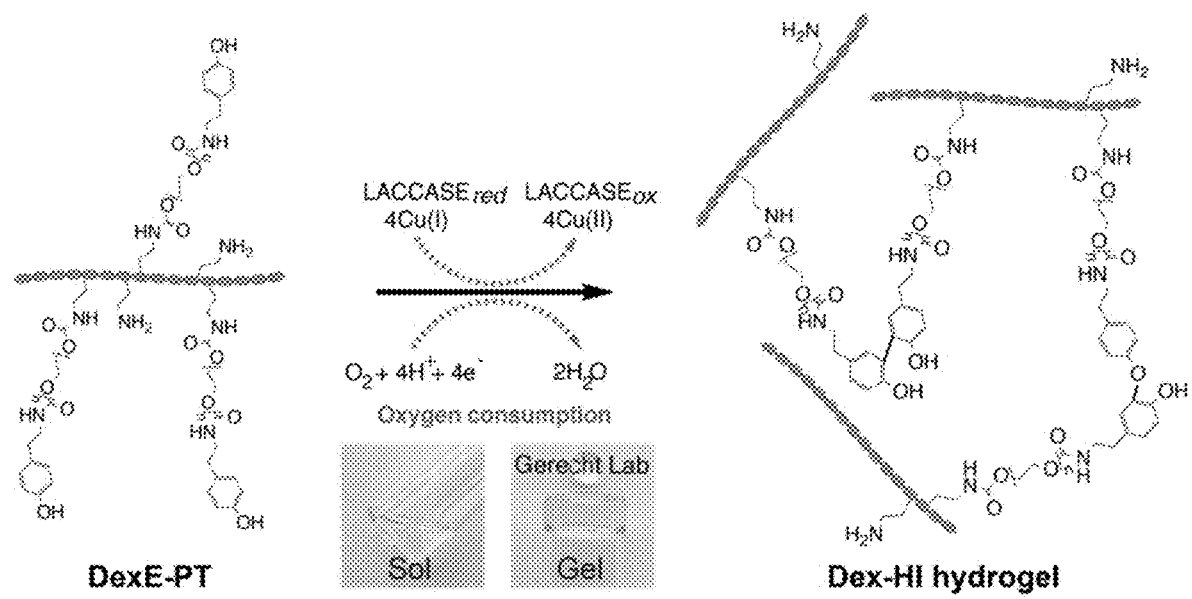
FIG. 28: Dextran-based hypoxia-inducible hydrogels. Schematic representation of Dex-HI hydrogel formation. Dex-HI hydrogels are prepared through an in situ $O_2$ consuming laccase-mediated reaction (inset micrographs of sol-gel transition of the transparent Dex-HI hydrogels). In this reaction, laccase catalyzes the reduction of $O_2$ into water ($H_2O$) molecules, resulting in conjugation of TA molecules through either carbon-carbon bonds at the ortho positions or carbon-oxygen bonds between the ortho carbon and the phenoxy oxygen (illustrated in box).

HI hydrogel of the invention can be prepared by crosslinking. Crosslinking may be achieved by any cross-linking method, including ionic crosslinking, ultraviolet crosslinking, enzymatic crosslinking, and chemical crosslinking reaction. In an embodiment of the invention, crosslinking is achieved by enzyme-mediated reaction that uses enzymes, such as, for example, laccase or tyrosinase. For example, HI hydrogel can be generated by crosslinking FA molecules via a laccase-mediated chemical reaction (FIG. 1A) to form diferulic acid (DiFA) (FIG. 4), which yields polymer networks (Riva, S., *Trends in biotechnology*, 2006; 24:219-226). Also, hydrogels are synthesized by crosslinking TA molecules in laccase-mediated reaction that yields polymer networks (FIG. 28).

Figure 1B:
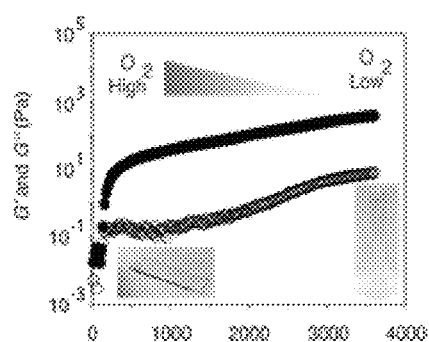
FIG. 1B Elastic modulus (G', filled symbols) and viscous modulus (G", opened symbols) of GtnFA HI hydrogels as functions of time. Rheological analysis shows dynamic network formation and gelation kinetics for 3 wt % of GtnFA HI hydrogel with 25 U/mL of laccase (inset micrographs show sol-gel transition of the hydrogels).
Figure 5:
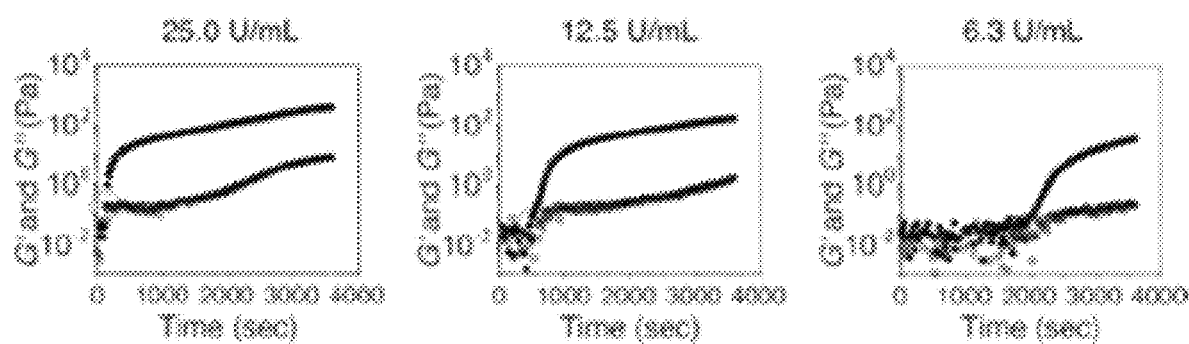
FIG. 5: Control of viscoelastic properties. Elastic modulus (G', filled symbols) and viscous modulus (G., open symbols) of GtnFA HI hydrogels as a function of time; effect of laccase concentration (0-25 U/mL). Measurements were performed with constant strain of 10%/and frequency of 0.1 Hz using 25 mm plate. Red circles represent the cross point of G' and G, indicating the gelation time.
Figure 29A:
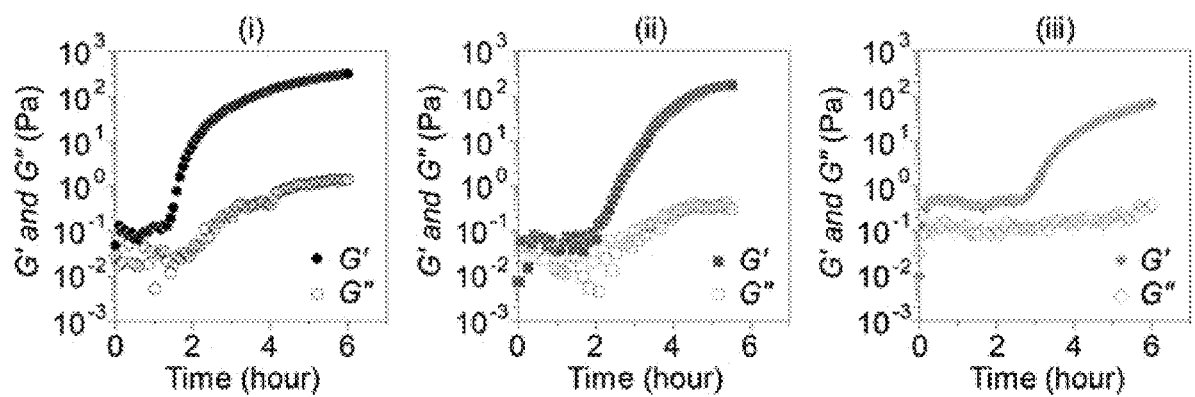
FIGS. 29A-29C: Hydrogel network formation kinetics and viscoelastic properties of Dex-HI hydrogels.

Rheological analysis, including dynamic time sweep and frequency sweep, evidences hydrogel formation and viscoelastic modulus. The crosslink point of elastic (G') and viscous (G") modulus, which provides an estimate of the gelation time, occurs within about 2 to about 30 minutes for GtnFA hydrogel (FIG. 1B and FIG. 5). This suggests that enzyme concentration for cross-linking affects the network formation kinetics. These data agree with the gelation kinetics observed by phase transition (FIG. 6A), indicating that higher concentrations of enzyme and polymer induce faster hydrogel formation. This may result from the rate of radical generation, which can induce DiFA formation, increasing with higher laccase and polymer concentrations. Moreover, viscoelastic measurements show tunable mechanical properties of the HI hydrogels (35 to 370 Pa). In DexE-PT HI hydrogel, as polymer concentrations increased from 3 w/v % to 10 w/v %, hydrogel formation proceeded with a slower phase transition rate (FIG. 29A). G' values of Dex-HI3 (i.e., DexE-PT HI hydrogel with 3 w/v % polymer) hydrogel increased dramatically after 1.3 hours, whereas G' of Dex-HI10 hydrogels increased after 2.7 hours; the higher polymer concentrations induce slower hydrogel formation. Differences in $O_2$ diffusivity of precursor solutions contribute to the transition rate, since increasing polymer concentration induces lower $O_2$ diffusion in the solutions (data not shown), resulting in a slower laccase-mediated crosslinking reaction. Dex-HI hydrogels can be generated using lower molecular weight Dex (<70 kDa) and higher molecular weight PEG (>4 kDa) molecules, which could decrease polymer viscosity and promote the crosslinking reactivity.

Figure 29B:
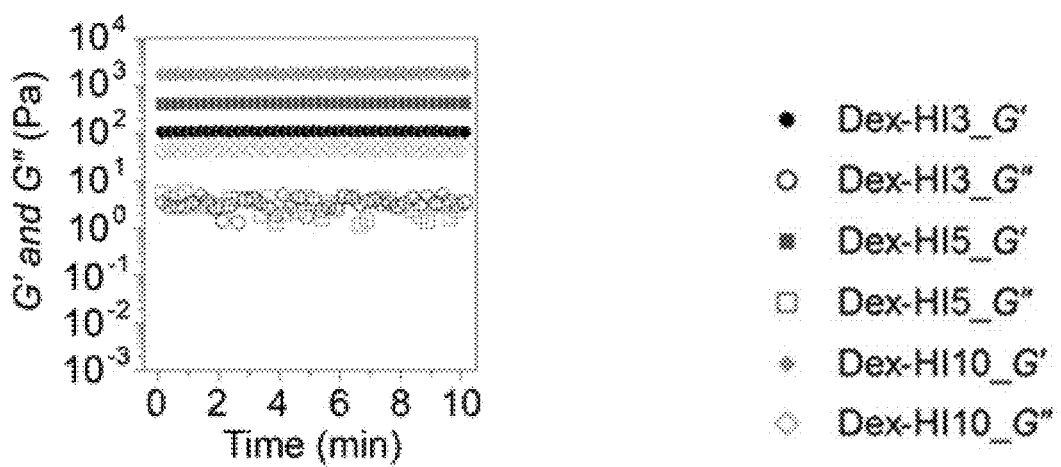

Dynamic time sweep at the equilibrium swelling state was used to determine the effect of polymer concentration on the final mechanical strength of Dex-HI hydrogels. Viscoelastic measurements exhibited tunable mechanical properties of the Dex-HI hydrogels (Dex-HI3, 110 Pa; Dex-HI5, 450 Pa; Dex-HI10, 1840 Pa) by varying polymer concentrations (FIG. 29B). Viscoelastic properties measured by dynamic frequency sweep (0.01-10 Hz) confirm the stability of the hydrogel network formation. Increasing frequency did not affect the elastic modulus (FIG. 29C), demonstrating that the hydrogel network structures of Dex-HI hydrogels are stable after hydrogel formation. The physicochemical properties of Dex-HI hydrogels are summarized in Table 3. The tunable properties and stable network formations allow the hydrogel to maintain a 3D shape, which provides structural frameworks as extracellular microenvironments to support cell function.

Figure 7A:
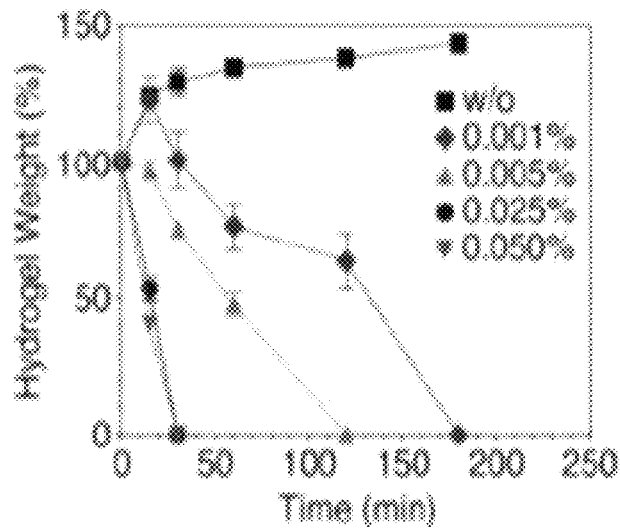
FIGS. 7A-7B: Proteolytic degradation of GtnFA HI hydrogels.
Figure 7B:
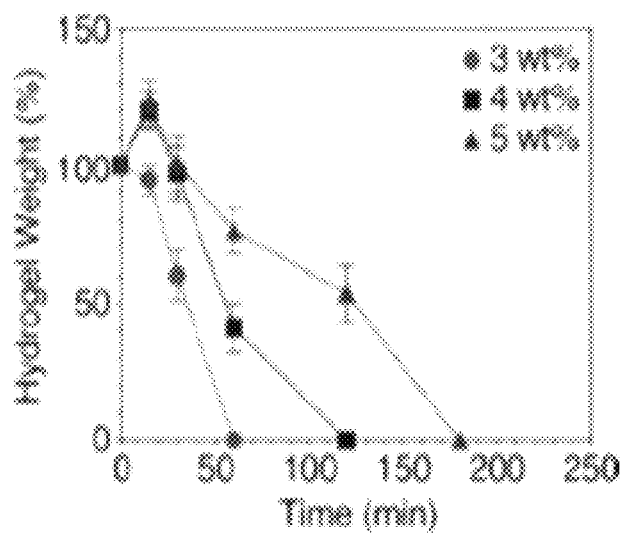

Proteolytic degradability, another parameter considered important in designing cellular microenvironments, allows cell migration and niche remodeling (Lutolf, M. P. et al., *Nature biotechnology*, 2005; 23:47-55; Lutolf, M. P. et al., *PNAS USA*, 2003; 100:5413-5418). In protease-sensitive degradation of HI hydrogels, GtnFA hydrogels incubated with collagenase degraded completely within about three hours, the rate varying with the concentrations of collagenase, for example about 0.001% to about 0.05%, and polymer for example about 3% to about 5% solution (FIG. 7). Proteolytic degradability of the Gtn-based HI hydrogel of the invention is retained following functionalization with FA molecules to GtnFA.

Figure 1C:
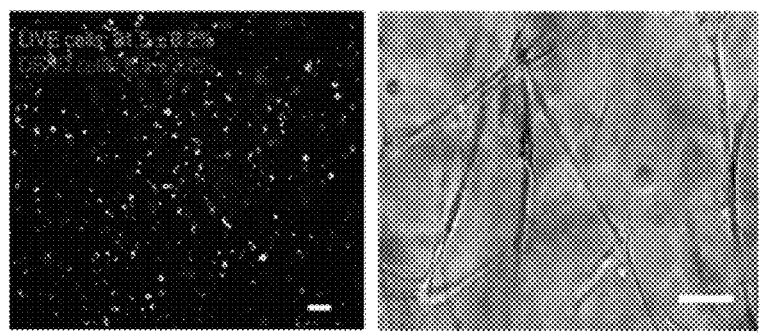
FIG. 1C Cytocompatibility of GtnFA HI hydrogels demonstrated by fibroblasts encapsulated within the HI hydrogel and analyzed for: left viability after 24 h (green, live cells; red, dead cells; scale bar is 100 m) and right cell spreading and elongation after 10 days in culture. Scale bar is 50 m.
Figure 8A:
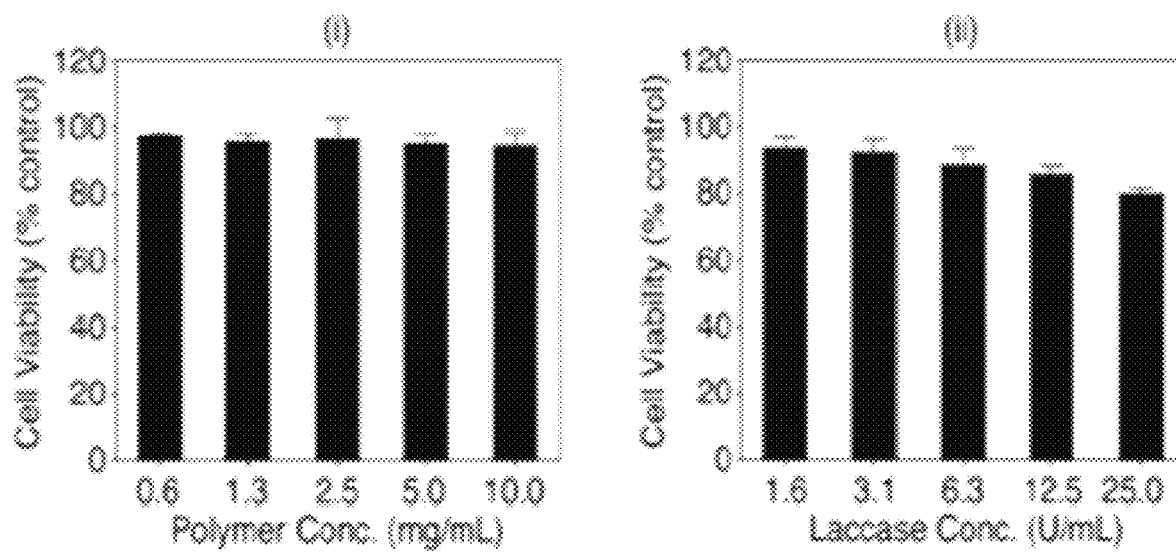
FIGS. 8A-8C: Cytocompatibility of GtnFA HI hydrogel.
Figure 8B:
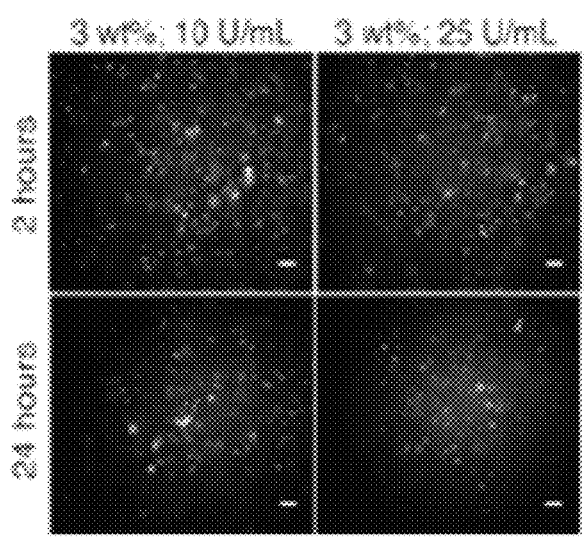
Figure 8C:
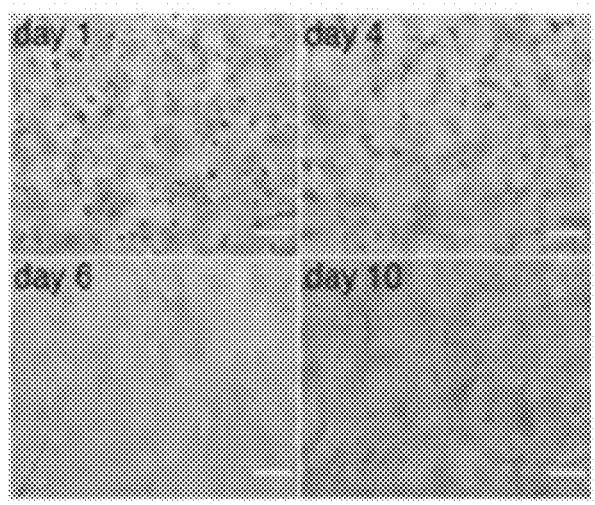
Figure 30A:
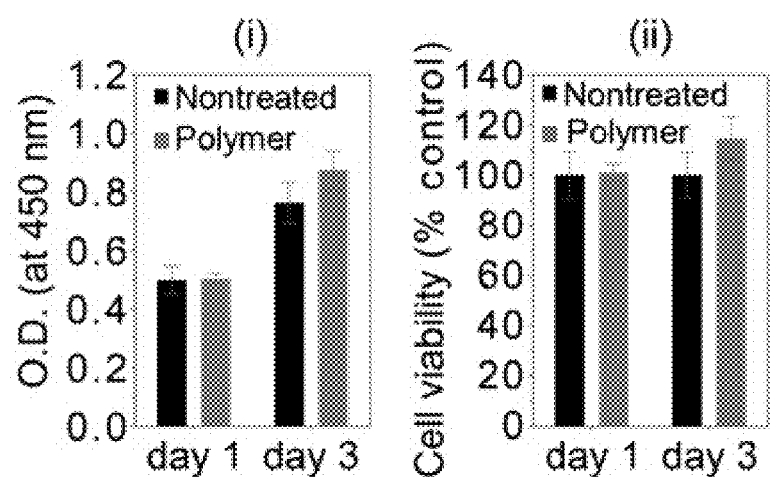
FIGS. 30A-30B: Cytocompatibility of Dex-HI hydrogels.
Figure 30B:
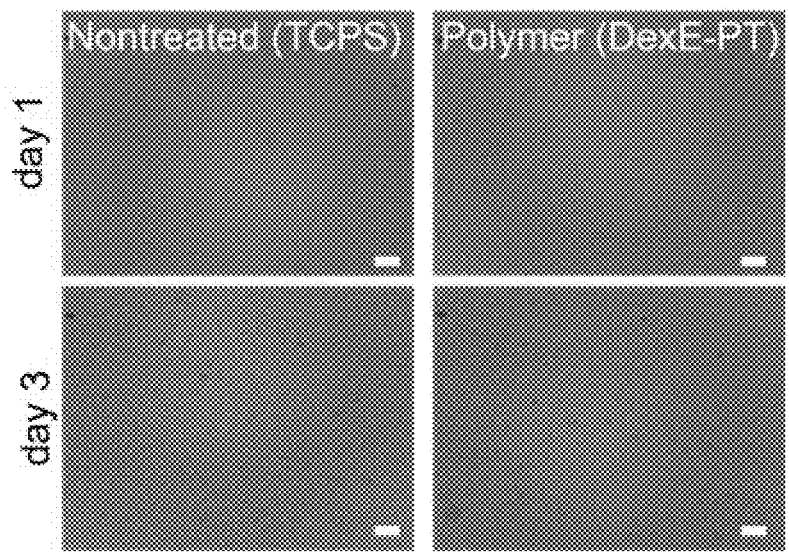

Although precursor and free enzyme molecules can induce toxicity in a hydrogel matrix, the hydrogels of the invention exhibit biocytocompatability. No significant cytotoxicity occurs in the GtnFA polymer (80 to 98% of control) (FIG. 8A). Fibroblasts encapsulated within the GtnFA HI hydrogels result in a viable fibroblast population, as well as cell spreading and elongation within HI hydrogel matrices (FIGS. 1C and 8B-8C). In addition, DexE-PT exhibited no significant cytotoxicity with encapsulation of human umbilical vein endothelial cells (day 1, 100±9.1% of control; day 3, 114.7±8.6% of control) and the cells proliferated well up to day 3 (FIGS. 30A-B). HI hydrogels of the invention have tunable parameters essential for their use as a 3D cellular microenvironment (Place, E. S. et al., *Nature materials*, 2009; 8: 457-470; Lutolf, M. P. et al., *Nature biotechnology*, 2005; 23:47-55; Tibbitt M. W. et al. *Biotechnology and bioengineering*, 2009; 103:655-663). The cytocompatible of the HI hydrogels confirms their potential for in vivo applications.

Figure 9A:
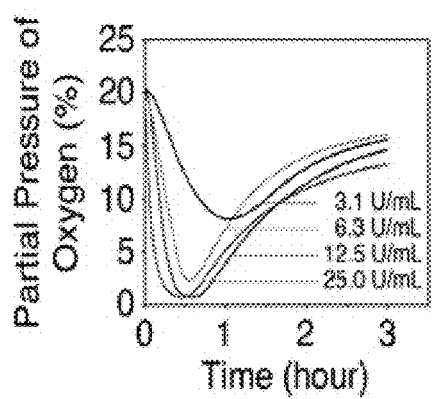
FIGS. 9A-9C: Controllable DO levels. DO levels of GtnFA HI hydrogels as a function of time.
Figure 9B:
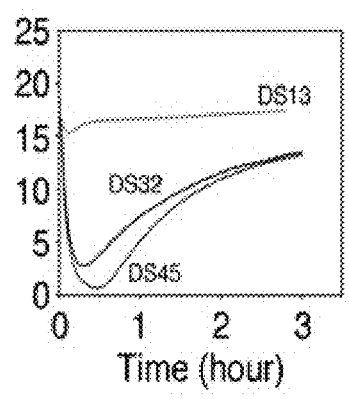

The hydrogels of the invention induce polymer network formation by $O_2$ consumption during hydrogel formation. Oxygen levels within the matrix were determined by monitoring DO levels at the bottom of hydrogels using a noninvasive sensor patch (Abaci, H. E. et al., *American journal of physiology: Cell physiology*, 2011; 301:C431-440). Several factors affect DO levels and oxygen consumption rates, including hydrogel thickness, enzyme concentration, polymer concentration, DS values of polymers, and culture media. Increasing enzyme concentrations decreased the DO levels and the time to reach the minimum DO level ($DO_{min}$), demonstrating that high enzyme concentrations induce rapid $O_2$ consumption reaction and low $O_2$ levels (FIG. 9A). These data agree with the results of hydrogel formation studies, indicating that enzyme concentration significantly affects both hydrogel network formation kinetics and oxygen consumption rates. Similarly, the higher DS value of FA molecules resulted in the lowest DO levels (FIG. 9B). Decreasing the FA content increased the $DO_{min}$. Thus, increasing FA content (higher DS) induces rapid $O_2$ consumption and low DO. The FA molecule acts as a crosslinker, consuming $O_2$ molecules during hydrogel network formation.

Hydrogel thickness also influences DO levels. Gel thickness can be varied in a volume-dependent manner. FIG. 2A shows that controllable DO levels depend on the HI hydrogel thickness (3 wt %, DS 45, and 25 U/mL laccase). $DO_{min}$ decreased as thickness increased, demonstrating that intramural DO levels vary with matrix thickness. Notably, DO levels are observed within thick hydrogels (>2.5 mm) reaching hypoxic levels (<5%), which indicates their suitability for providing artificial hypoxic microenvironments.

Figure 9C:
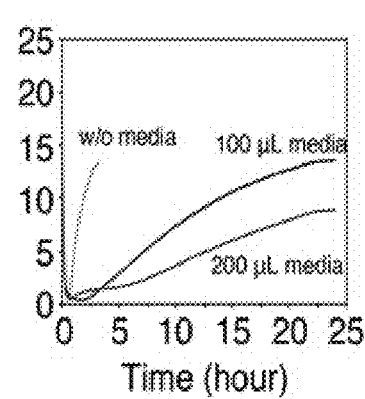

Culture media is another factor that can affect DO levels. DO levels in HI matrices placed in culture media exhibited lower DO levels, and slower $O_2$ diffusion than hydrogel in air (FIG. 9C). $O_2$ diffusion is slower in larger volumes of media, which can be due to the media serving as a diffusion barrier between air and hydrogel matrices.

Figure 31A:
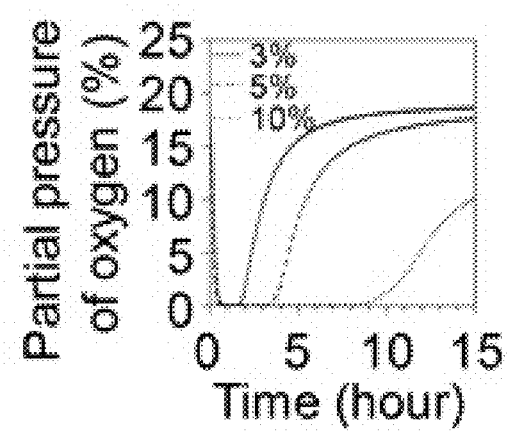
FIGS. 31A-31E: $O_2$ measurements and model predictions of DO levels in Dex-HI hydrogels.
Figure 31B:
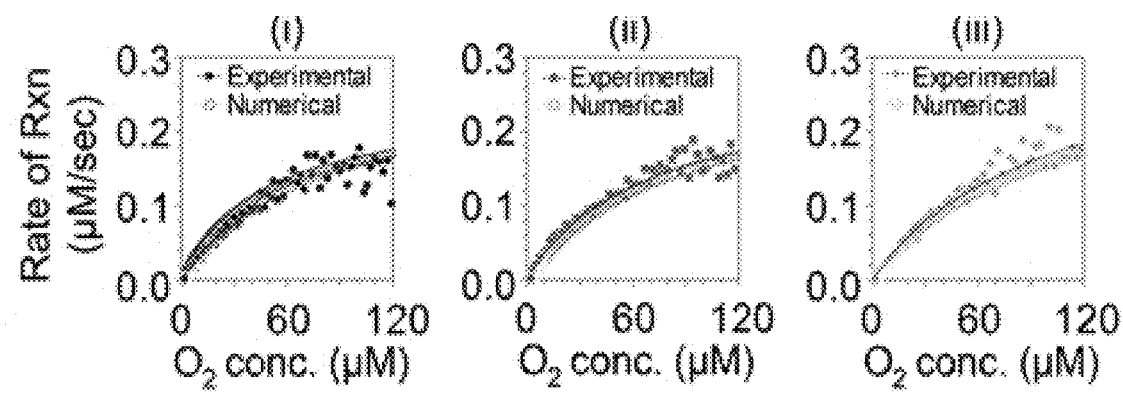
Figure 31C:
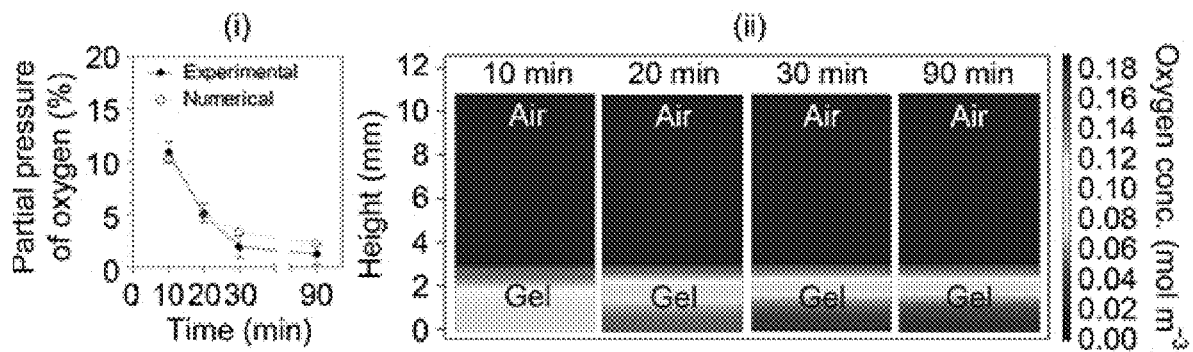
Figure 31D:
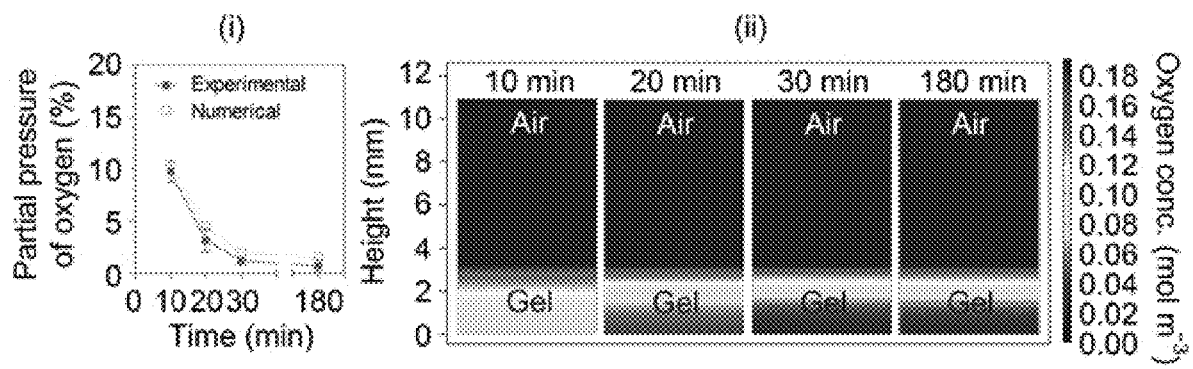
Figure 31E:
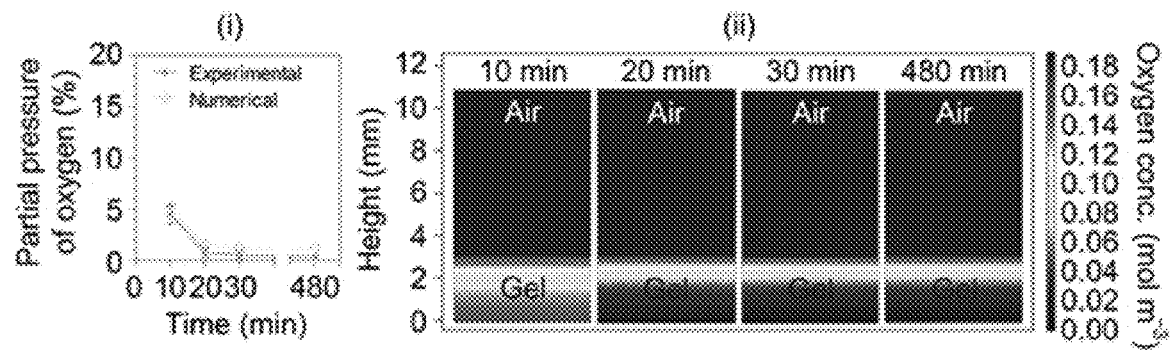

DO levels decreased dramatically during the initial 30 minutes, and maintained low $O_2$ tension (<0.5%, defined as the steady state) up to 1.5 hours for Dex-HI3, 3 hours for Dex-HI5, and 8 hours for Dex-HI10, demonstrating an ongoing chemical reaction. After steady state was reached, the DO levels increased gradually, demonstrating that the chemical reaction was complete. The higher polymer concentrations induced rapid $O_2$ consumption and maintained prolonged hypoxic conditions. For example, as polymer concentrations were increased from 3 w/v % (Dex-HI3) to 10 w/v % (Dex-HI10), the hydrogels showed faster $O_2$ consumption rate during the initial 30 minutes and longer hypoxic conditions (up to 12 hours) (FIG. 31A). This is consistent with TA content increasing from 5.1 mM to 17.0 mM (consuming $O_2$ molecules), which induces a much faster chemical reaction. Dex-HI hydrogels generated longer hypoxic conditions (up to 12 hours) compared to Gtn-HI hydrogels (up to 1 hour). The prolonged hypoxic conditions of Dex-HI hydrogels provide an advantage to promote accumulation and stabilization of HIFs, which regulate myriad gene expression affecting cellular activities (Simon, M. C. and Keith, B., *Cell* 2007, 129, 465; Semenza, G. L., *Trends Mol. Med.* 2001, 7, 345; Heddleston, J. M. et al., *Br. J. Cancer* 2010, 102, 789; Mazumdar, J. et al., *Cell. Mol. Med.* 2009, 13, 4319). The prolonged hypoxic conditions in the Dex-HI can be achieved based on the chemical reaction parameters and thus the HI hydrogel can be tuned.

A mathematical model developed previously (Abaci, H. E. et al., *American journal of physiology: Cell physiology*, 2011; 301:C431-440) provides accurate prediction of DO levels and gradients within HI hydrogels. $O_2$ consumption kinetics during hydrogel formation follows Michaelis-Menten kinetics, as shown in equation (1).

$$R = \frac{V_{max} C_{O2}}{K_m + C_{O2}} \quad (1)$$

Figure 11:
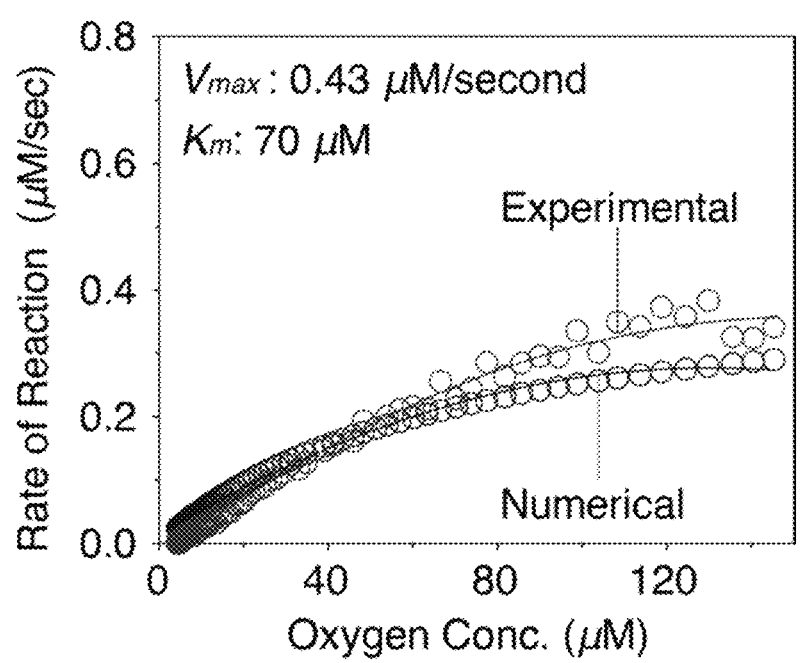
FIG. 11. Oxygen consumption rate in GtnFA hydrogel. Oxygen consumption rate of laccase-mediated crosslinking reactions following Michaelis-Menten kinetics. Plots were calibrated according to the residual sum of squares (RSS) method to find the best fit between theoretical and experimental values. $V_{max}$ and $K_m$ values of the hydrogels were 0.43 μM/sec and 70 μM, respectively.

For accurate estimates of DO gradients in HI hydrogels, the $V_{max}$ and $K_m$ parameters were determined. DO levels at the bottom of the HI hydrogels (3 wt %, DS45, and 25 U/mL enzyme for GtnFA; 3, 5, and 10 w/v %, DS 170, and 25 U/mL enzyme for DexE-PT) were measured until they reach steady state. The oxygen consumption rate of the enzyme-mediated reaction (experimental data) and the theoretical Michaelis-Menten equation (numerical model) using the initial $V_{max}$ and $K_m$ values were plotted. The graphs were then calibrated while varying the $V_{max}$ and $K_m$ parameters to obtain the best fit to the experimental values according to the residual sum of squares (RSS method for GtnFA, FIG. 11; GraphPad Prism 4.02 for DexE-PT, FIG. 31). $V_{max}$ and $K_m$ values of Dex-HI hydrogels were 0.26 µM/sec and 64.82 µM for Dex-HI3, 0.26 µM/sec and 73.93 µM for Dex-HI5, and 0.33 µM/sec and 98.86 µM for Dex-HI10, respectively. The $V_{max}$ values of Dex-HI hydrogels were lower than that of Gtn-HI hydrogels (0.43 µM/sec) even though Dex-HI hydrogels contain higher concentrations of phenolic molecules (5.1-17.0 mM) compared to Gtn-HI hydrogels (1.35 mM). This may be due to the $O_2$ consumption rate of the laccase-mediated reaction using FA faster than that of the enzymatic reaction using TA molecules (M. L. Mattinen, et al., *FEBS J.* 2005; 272: 3640). Overall, although Gtn-HI hydrogels showed faster $V_{max}$ values, Dex-HI hydrogels exhibit lower $O_2$ levels and prolonged hypoxic environments due to the high content of phenolic molecules that can consume $O_2$ during hydrogel formation.

The experimental DO values at the different hydrogel thicknesses to numerical DO values determined by the mathematical modeling confirm the reliability of the given parameters. As can be seen in FIG. 10B and FIGS. 31C-31E, the experimental values are similar to the numerical model simulated by using the obtained $V_{max}$ and $K_m$ values. These results showed that the 02 consumption rate (i.e., hydrogel formation kinetics) follows the theoretical Michaelis-Menten equation.

Figure 10D:
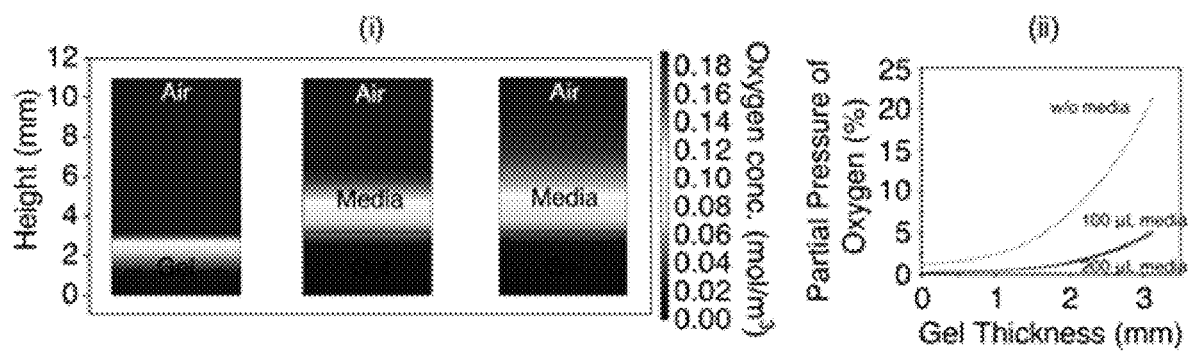

Using the Michaelis-Menten parameters determined for the given conditions, the DO gradients throughout the gel depth in two-layer (air-hydrogel) and three-layer (air-media-hydrogel) models can be estimated. In a two-layer model, the DO levels at the bottom of hydrogels decreased as gel thickness increased, due to insufficient oxygen diffusion (FIG. 10C(i)), and a broad range of $O_2$ tensions occurred within the gel matrices (FIG. 10C(ii)). For instance, the $O_2$ gradient of the thin hydrogel (about 1.25 mm) ranged from about 15% to about 17%, while a thicker hydrogel (about 3.13 mm) exhibited an about 1.8 to 21% range, demonstrating that hydrogel thickness strongly affected $O_2$ levels and gradients. Computer simulation for media effects on $O_2$ gradients using the three-layer model shows that hydrogels placed in media exhibited lower intramural DO levels. FIG. 10D(i-ii). In fact, at thicknesses between about 2.5 mm and about 3.13 mm, DO levels were hypoxic (>5%) through the hydrogel depth. For DexE-PT hydrogel, increasing polymer concentration induced lower $O_2$ levels (Dex-HI3, 1.2±1.1%; Dex-HI5, 1.2±0.4%; Dex-HI10, 0.5±0.4%) and a broad range of $O_2$ gradient after 30 minutes (Dex-HI3, 1.2%-20.3%; Dex-HI5, 1.2%-20.0%; Dex-HI10, 0.5%-20.3%). Dex-HI hydrogels exhibited lower $O_2$ levels and a wider range of $O_2$ gradient compared to Gtn-HI hydrogels ($O_2$ levels at the bottom of Gtn-HI hydrogel; 1.8%; $O_2$ gradient, 1.8-21%.

Figure 32A:
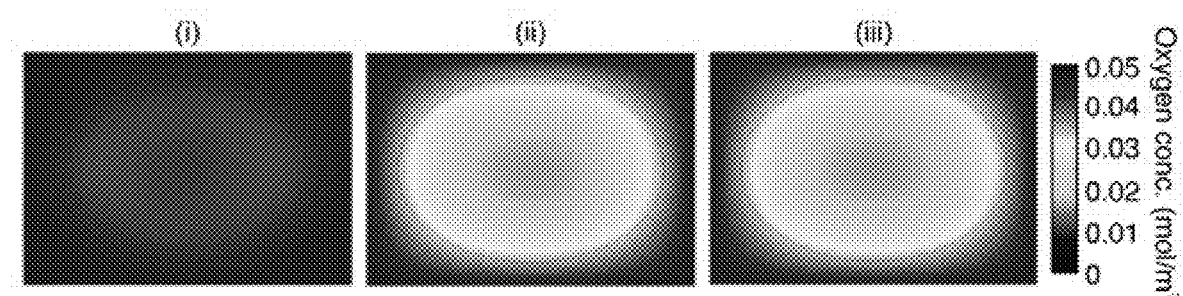
FIGS. 32A-32C: Model prediction of the DO levels of Dex-HI hydrogel in in vivo environments.
Figure 32B:
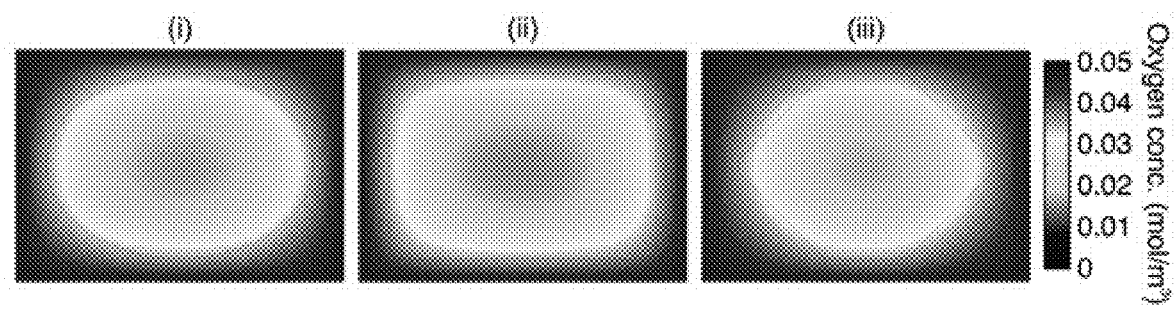
Figure 32C:
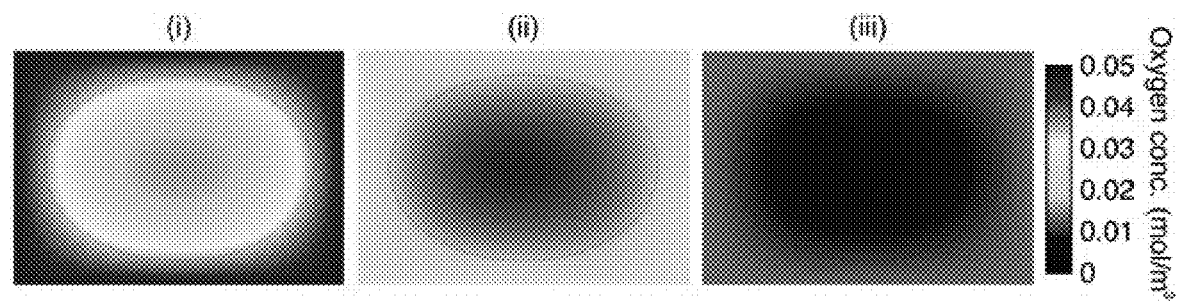

Using the given parameters, DO levels and gradients were estimated after theoretical in vivo injection of Dex-HI10 hydrogels. DO levels were simulated at different time points up to 8 hours (the end of the steady state of Dex-HI10). For this model prediction, a partial pressure of $O_2$ ($pO_2$) in subcutaneous tissue of 40 mmHg was assumed, following previous reports (B. Fischer, *J. Reprod. Fertil.* 1993; 99: 673; Y. N. Zhang, *Anal. Chim. Acta* 1993; 281: 513). As shown in FIG. 32A, the DO gradient from the core to the interface between the Dex-HI hydrogel and the tissue decreased during the initial 30 minutes: 10 minutes after injection, DO level of the hydrogel core is $4.3 \times 10^{-2}$ mol m$^{-3}$ and the DO level of the interface is $4.5 \times 10^{-2}$ mol m$^{-3}$; 30 minutes after injection, DO levels of the hydrogel core is $1.6 \times 10^{-2}$ mol m$^{-3}$ and the DO level of the interface is $3.6 \times 10^{-2}$ mol m$^{-3}$). Moreover, low $O_2$ levels were maintained for up to 8 hours where DO level of the hydrogel core is $1.6 \times 10^{-2}$ mol m$^{-3}$; a DO level of the interface is $3.6 \times 10^{-2}$ mol m$^{-3}$. After 8 hours, the DO levels may increase gradually, possibly through increased $O_2$ diffusion as the chemical reaction is completed as mentioned above. DO levels with different hydrogel geometries (e.g., ellipse, rectangle, and polygonal shape) were simulated, as needed to consider that the hydrogels form irregular shapes following injection into dynamic in vivo environments. After 30 minutes, the DO gradient within the hydrogels was independent of the hydrogel geometry (FIG. 32B). Simulation of the $O_2$ gradients upon theoretical injection into tissue with pathological $O_2$ levels (<40 mmHg) that are already ischemic and hence, hypoxic, showed that DO levels at the edge of the hydrogels were lower than the surrounding in vivo environment (FIG. 32B). In an embodiment of the invention, Dex-HI hydrogel formation induces an acute hypoxic environment (up to 12 hours) that can stimulate surrounding tissues in dynamic in vivo environments.

Oxygen measurements and computer simulations illustrate that HI hydrogels consume $O_2$ during their formation, yielding an $O_2$ gradient within the matrix. Various factors can control the consumption rate. The ability to reach hypoxic level under the different conditions, particularly prolonged periods, demonstrates the suitability for the HI hydrogels of the invention in providing artificial hypoxic microenvironments.

Figure 12A:
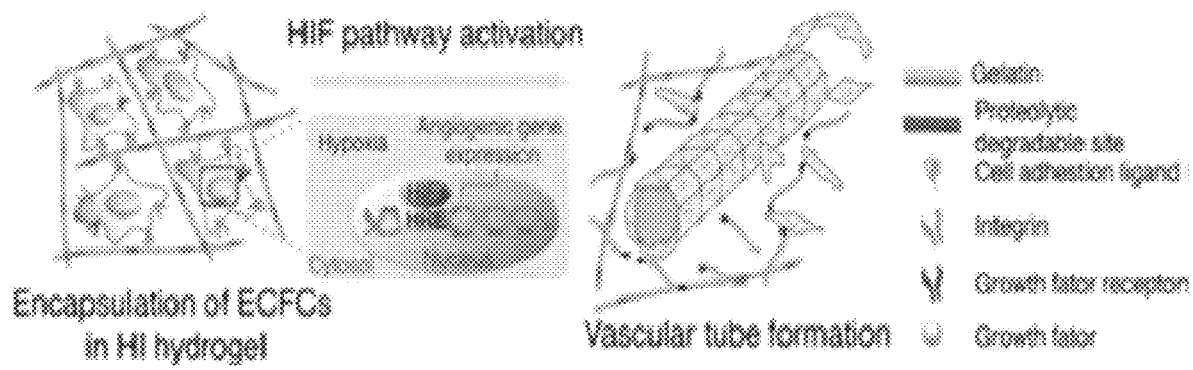
FIGS. 12A-12E: The HI hydrogel as a dynamic microenvironment for vascular morphogenesis.

HI hydrogels stimulate vascular morphogenesis through HIF pathway activation (FIG. 12A), which demonstrates the importance of the 3D hypoxic niche in cellular response. Cells, for example fibroblasts, ECFCs and tumor cells, and tissue, for example tumor tissue, can be encapsulated within HI hydrogel matrices of different thickness, e.g. hypoxic gel, 2.50 mm, 1.25 mm. DO levels of hydrogels with cells depend on gel thickness. DO levels of the hypoxic gels decrease for the first 30 minutes and retain prolonged low $O_2$ levels (under 0.5% $O_2$) (FIGS. 13 and 31A), demonstrating that the HI hydrogels allow the exposure of cells and tissue to hypoxia and that the cells or tissue also affect $O_2$ levels within the matrix. In fact, the DO levels of hypoxic gels without cells reached $DO_{min}$ within 30 minutes, followed by a gradual increase after the inflection point (FIG. 9C). DO levels within the hypoxic gels encapsulating cells remained hypoxic after $DO_{min}$ for up to 24 hours (FIG. 13), likely due to oxygen consumption by the cells. In contrast, nonhypoxic gels exhibited higher $O_2$ levels (>8%) than hypoxic gels but with a similar pattern, due to the encapsulated cells.

Figure 12B:
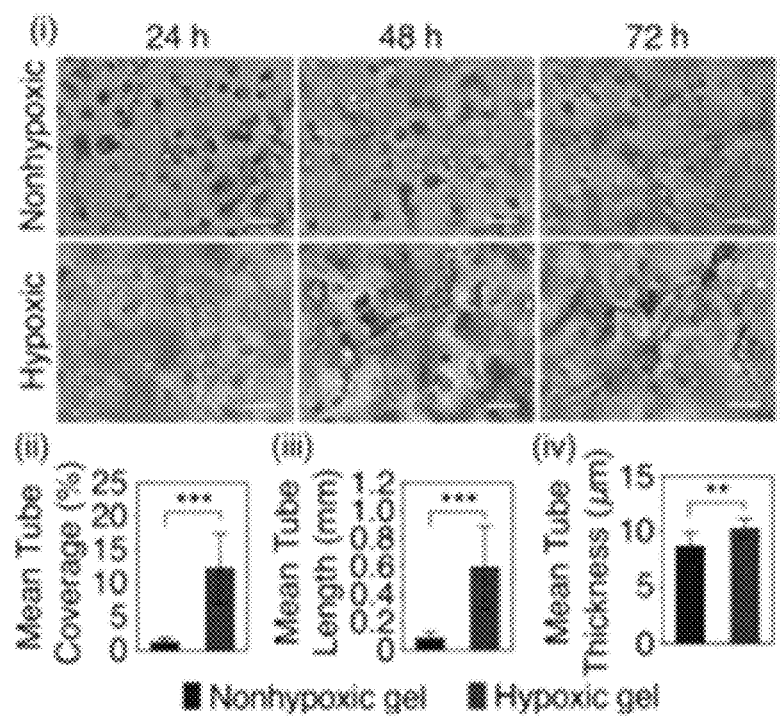
Figure 12C:
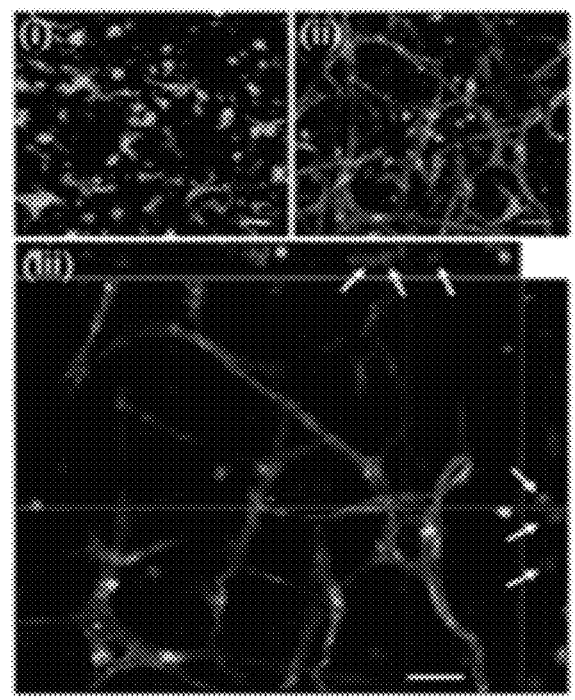

ECFCs encapsulated within the HI hydrogels demonstrate the influence of a 3D hypoxic microenvironment on the vascular morphogenesis. ECFCs have different cell morphologies in hypoxic versus nonhypoxic gels. Unlike the limited ECFC sprout and tube formation of ECFCs within the nonhypoxic hydrogels. ECFCs within hypoxic gels undergo tubulogenesis, forming complex network structures after three days in culture (FIG. 12B(i)). ECFCs also have significant increases in tube coverage, in tube length, and in tube thickness (FIG. 12B(ii-iv)), demonstrating that the HI hydrogels stimulate vascular morphogenesis. More evolved vascular structures are generated in hypoxic gels than in nonhypoxic gels, as shown in FIG. 12C(i-ii). Lumens in the vascular structures form in hypoxic hydrogels, indicating mature vascular tube formation (FIG. 12C(iii) and FIG. 14).

Figure 12D:
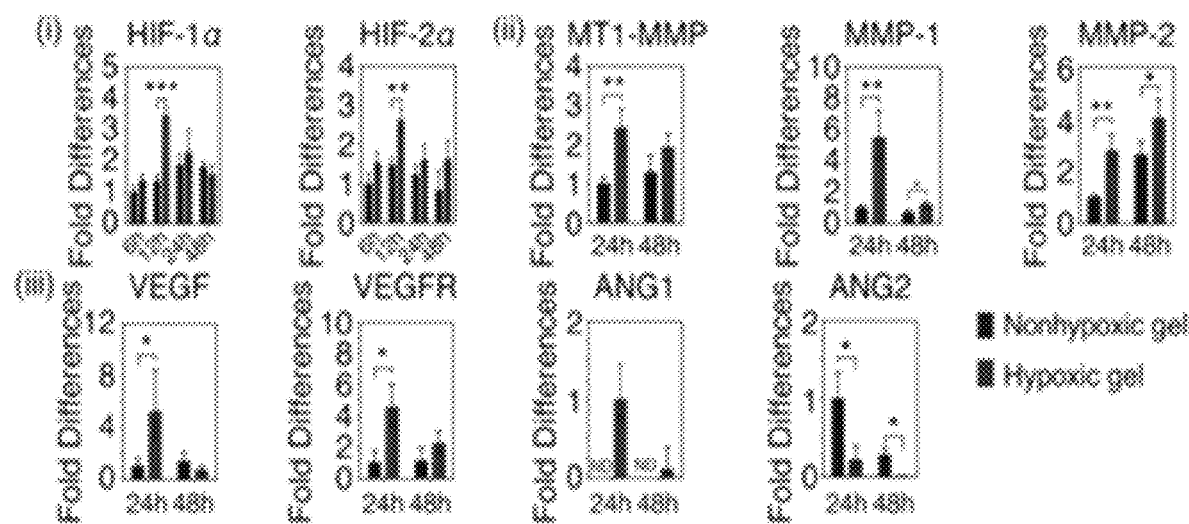

ECFCs cultured in hypoxic gels expressed significantly higher levels of two isoforms of HIFα (HIF-1α and HIF-2α) than ECFCs within nonhypoxic hydrogels (FIG. 12D(i)). HIF-1α gene expression gradually became upregulated in ECFCs in nonhypoxic gel for up to 24 hours during the culture period, probably due to the presence of FA molecules. A recent study demonstrated that free FA molecules could induce upregulation of HIF-1α expression in endothelial cells (ECs) in a concentration-dependent manner (Lin, C. M. et al., *J nutritional biochemistry*, 2010; 21:627-633).

Figure 15A:
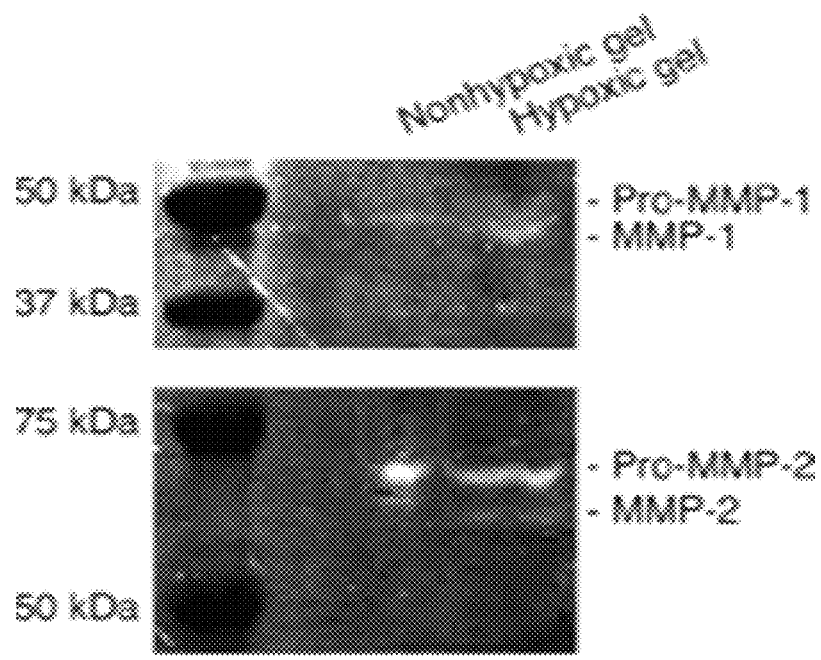
FIGS. 15A-15B: MMP expression in ECFCs within hypoxic gel vs. nonhypoxic gel.
Figure 15B:
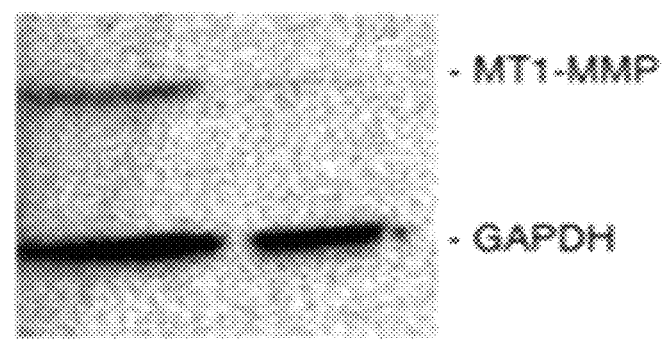

Expression of three MMP genes in ECFCs membrane type 1 (MT1)-MMP, MMP-1, and MMP-2 play a critical role in vascular morphogenesis (Hanjaya-Putra, D. et al., *Blood* 2011; 118:804-815; Chun, T. H. et al., *J of Cell Biology*, 2004; 167:757-767; Stratman, A. N. et al., *Blood* 2009; 114:237-247). All MMP gene expressions in ECFCs from the hypoxic gel were upregulated compared to ECFCs encapsulated in nonhypoxic gel (FIG. 3D(ii)). Also, higher levels of MT I-MMP and activated forms of MMP-1 and MMP-2 are found in hypoxic hydrogels (FIG. 15).

Analysis of gene expression of proangiogenic factors within the hypoxic microenvironment shows upregulation of VEGF and VEGFR2 in ECFCs encapsulated in hypoxic gel compared to nonhypoxic gel (FIG. 12D(iii)). ANG1, which contributes to blood vessel maturation and stabilization, was upregulated, while ANG2, an antagonist of ANG1, was downregulated in hypoxic hydrogels compared to nonhypoxic hydrogels. (FIG. 12D(iii)). Collectively, these results demonstrate that hypoxic hydrogels stimulate upregulation of proangiogenic and MMP genes affecting vascular morphogenesis.

Figure 13A:
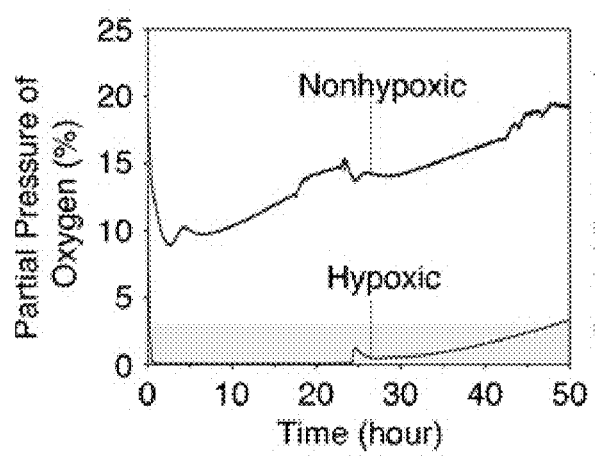
FIGS. 13A-13B: DO levels of GtnFA HI hydrogels encapsulated with ECFCs.
Figure 13B:
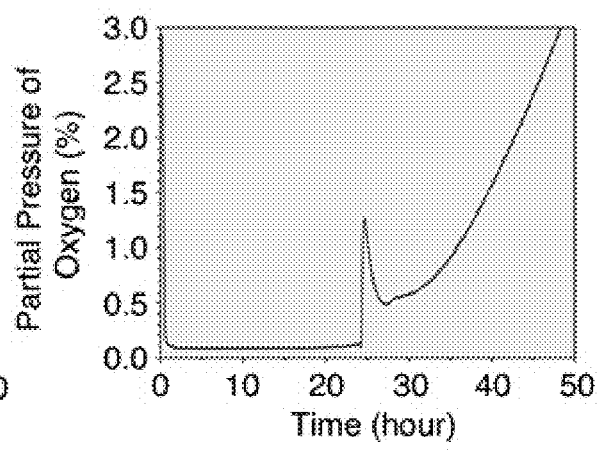
Figure 16A:
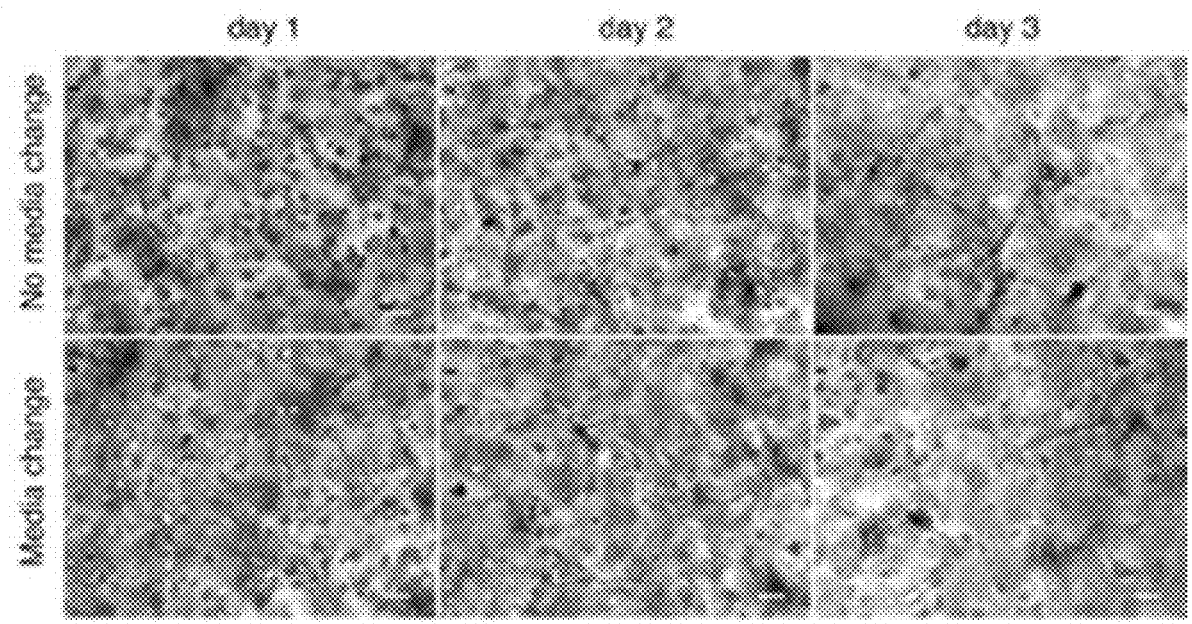
FIGS. 16A-16B: Effect of reoxygenation on vascular morphogenesis.
Figure 16B:
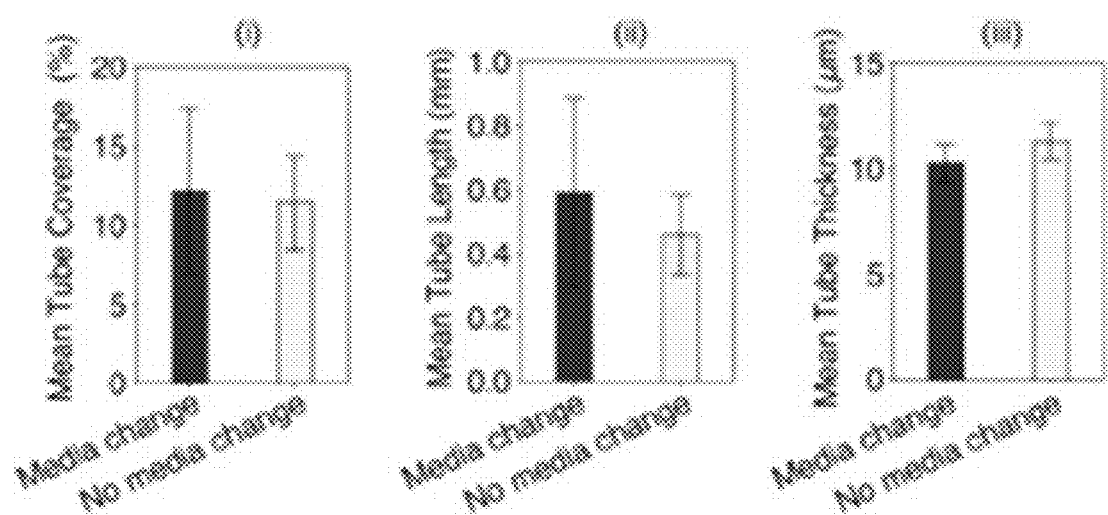

Reoxygenation, the phenomenon in which hypoxic regions become more exposed to oxygen by changing $pO_2$ (oxygen partial pressure (tension), induces production of reactive oxygen specimens, which involves an angiogenic response (Pan, Y. et al., *Molecular and cellular biology* 2007; 27:912-925). It was previously demonstrated that reoxygenation affected the tube formation kinetics of ECs encapsulated in collagen gels in atmospheric conditions through a HIFα-independent pathway (Abaci, H. E. et al., *Am J Physiology: Cell physiology*, 2011; 301:C431-440). In the HI hydrogel of the invention, oxygen fluctuates, from about 0.1% $O_2$ to about 1.3% $O_2$, and a gradually increases after media changes (FIG. 13). ECFCs encapsulated within HI hydrogels can be cultured with or without media changes, and ECFCs cultured without media changes undergo vascular morphogenesis similar to those cultured with media changes (FIG. 16), demonstrating that reoxygenation does not affect the angiogenic morphogenesis of ECFCs in HI hydrogel systems.

Vascular morphogenesis within HI hydrogels occurs through the activation of HIF. Small interfering RNA (siRNA) shows the involvement of HIF-1α and HIF-2α during ECFC tubulogenesis in HI hydrogels. ECFCs treated with either or both HIF siRNAs, after encapsulated in HI hydrogels and confirming the suppression (FIG. 17), knocking down each or both HIFs reduced tube area coverage and shortened tube length compared to untreated and luciferase-treated ECFCs (FIG. 12E(i-iii) and FIG. 18). Notably, when both HIFs were knocked down, most of the encapsulated ECFCs exhibit round shapes (FIG. 18). Significant downregulation of MT1-MMP expression is detected after 24 hours of culture in the ECFCs treated with both HIFs siRNA compared to nontreated, luciferase-treated, and each HIF-treated-alone groups (FIG. 12E(iv)). Collectively, these results demonstrate that regulation of HIF-1α and HIF-2a contribute to vascular morphogenesis of ECFCs within HI hydrogels and that this process involves the expression of MT1-MMP, previously established as a critical component for the progression of 3D tubulogenesis within hydrogel materials (Hanjaya-Putra, D. et al., *Blood*, 2011; 118:804-815; Chun, T. H. et al., *J of Cell Biology*, 2004; 167:757-767; Stratman, A. N. et al., *Blood*, 2009; 114:237-247). The HI hydrogels of the invention, which can induce hypoxic microenvironments, promote complex and mature vascular tube structures by activating HIFs through the upregulated expression of proangiogenic factors and MMPs.

Figure 19A:
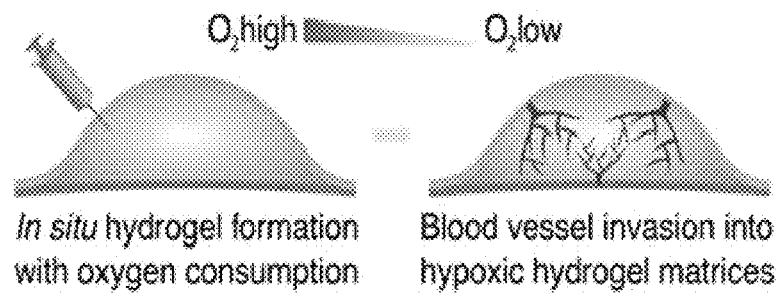
FIGS. 19A-19D: In vivo angiogenic effect of the GtnFA HI hydrogels.
Figure 19B:
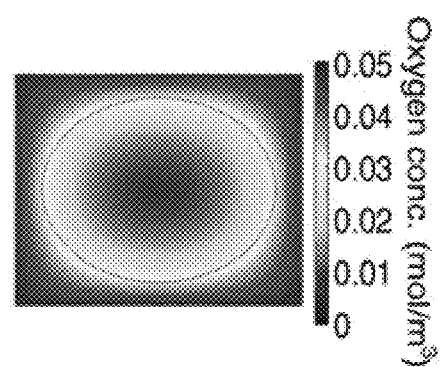

Although numerous studies have suggested that hypoxia stimulates blood vessel formation both in vitro and in vivo (Covello, K. L. et al., *Current topics in developmental biology*, 2004; 62:37-54; Pugh, C. W. et al., *Nature medicine*, 2003; 9:677-684; Marti, H. J. et al., *Am J Pathology*, 2000; 156:965-976), inducing acute hypoxia by manipulating a material-tissue interface to affect blood vessel invasion has not been reported. The HI hydrogels of the invention can induce acute hypoxia in surrounding tissues through in situ gel formation with oxygen consumption, which in turn stimulates blood vessel invasion (FIG. 19A). DO levels can be simulated to estimate in vivo injection of hypoxic hydrogels using the given parameters. A partial pressure of oxygen in rat subcutaneous tissue can be 40 mmHg, following previous reports (Fischer, B. et al., *J reproduction and fertility*, 1993; 99:673-679, Zhang, Y. et al., *Analytica Chimica Acta*, 1993; 281:513-520), although the exact pressure was not defined. DO levels can range from about $8.4 \times 10^{-3}$ mol/m$^3$ to about $3.2 \times 10^{-2}$ mol/m$^3$ from the hydrogel core to the interface between the gel surface and the surrounding tissue (FIG. 19B). DO levels at the interface were lower than the physiological $O_2$ levels of subcutaneous skin, demonstrating that hypoxic hydrogels can induce an acutely hypoxic environment and may stimulate the surrounding tissues.

Figure 19C:
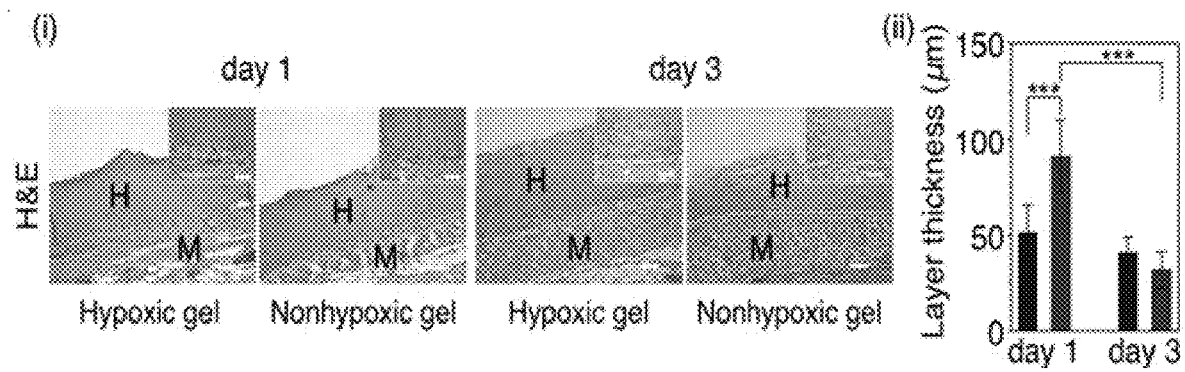
Figure 19D:
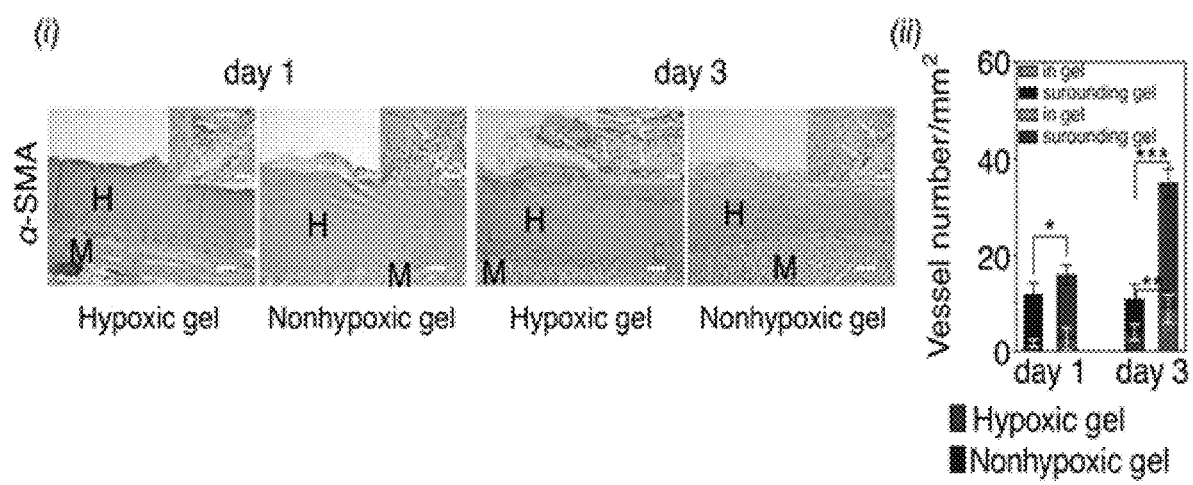
Figure 20:
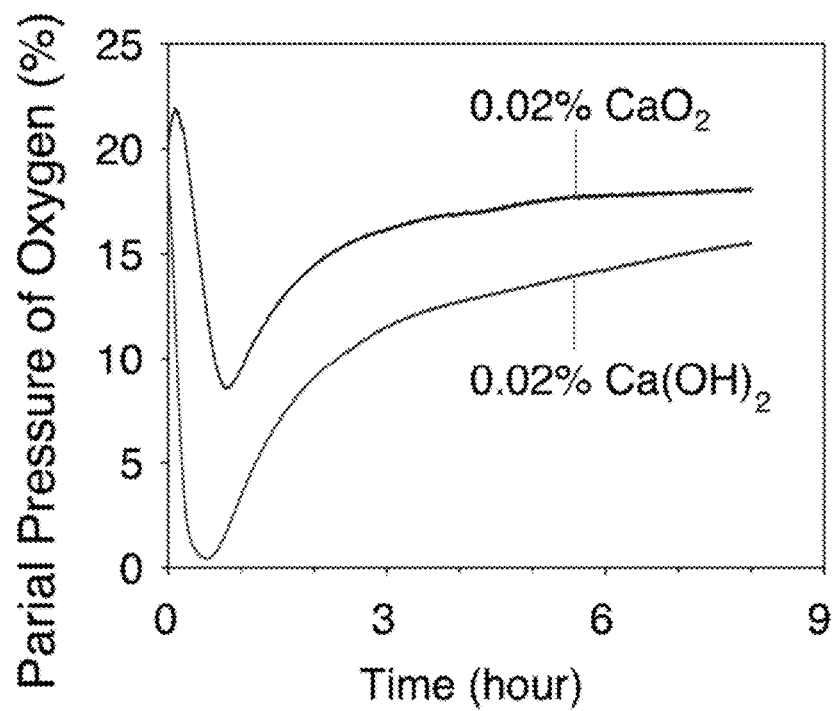
FIG. 20: Controlling DO levels for in vivo studies. DO levels of GtnFA HI hydrogels encapsulated with 0.02% of $CaO_2$ and $Ca(OH)_2$ (thickness of 3.13 mm; 100 μL plated on a 96-well plate).
Figure 21:
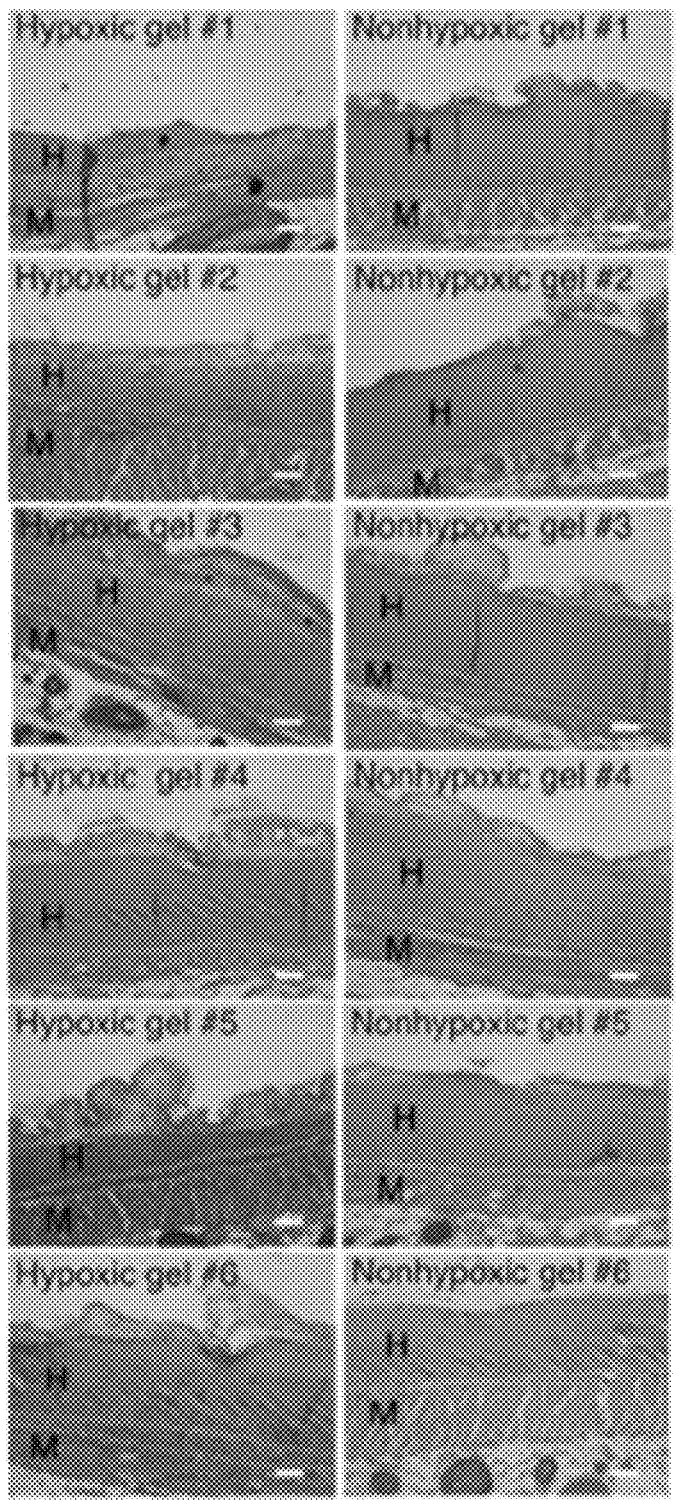
FIG. 21: Histological sections stained with H&E. Granulation layers at the muscle-hydrogel interface one day after implantation. Yellow dotted line represents the interface between muscle and hydrogel. M, muscle; H, hydrogel. Scale bar is 100 μm.
Figure 22:
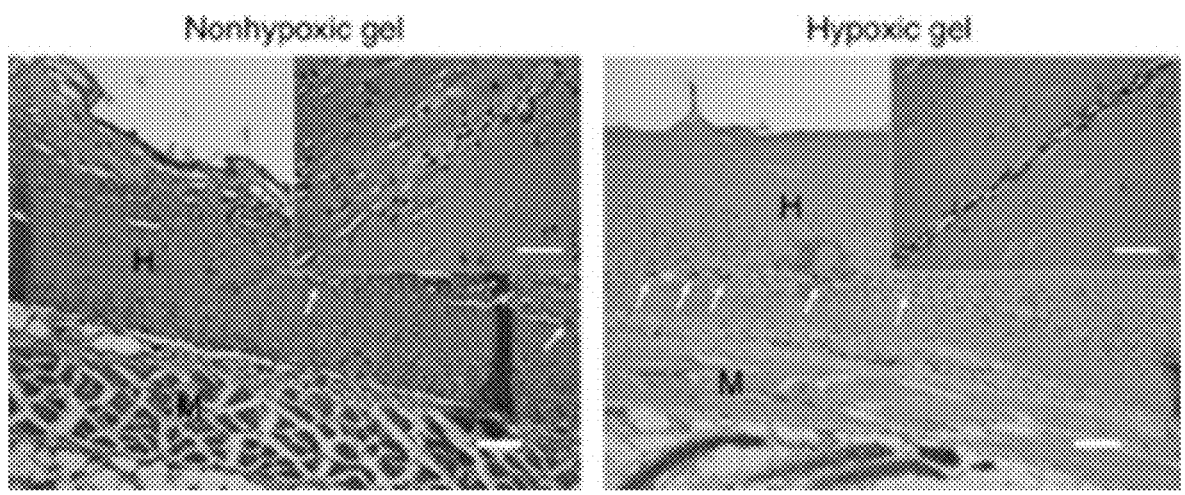
FIG. 22: Blood vessels infiltrated into GtnFA HI hydrogels. Histological section stained with α-SMA in nonhypoxic hydrogel (left panel) and hypoxic hydrogel (right panel) at day one; arrows indicate vascular structure within the hydrogels. M, muscle; H, hydrogel. Scale bars are 100 μm and 50 μm (in insets).
Figure 23:
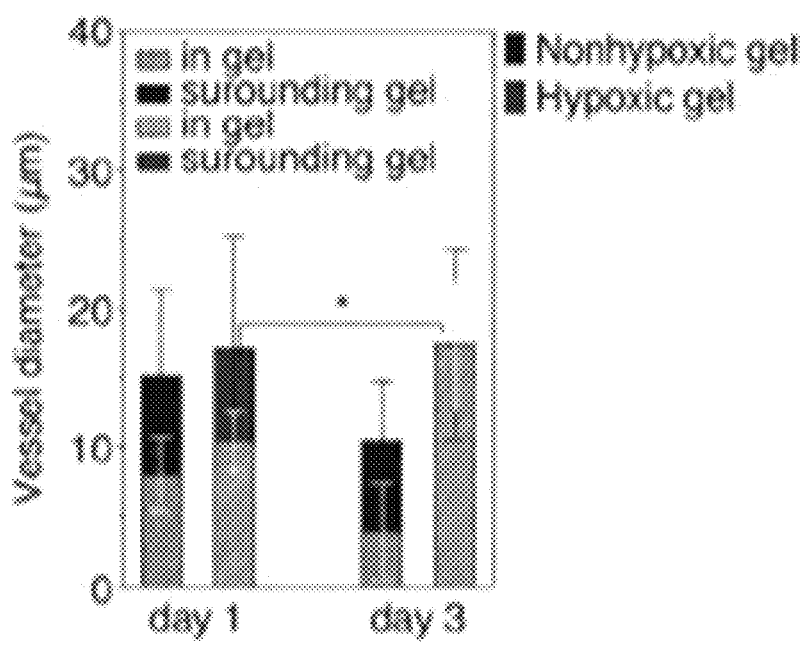
FIG. 23: In vivo angiogenic effect of the GtnFA HI hydrogels. Quantification of blood vessel diameter. Values shown are means±SD. Significance levels were set at: *p<0.05, p<0.01, and *p<0.001.

Comparing two HI hydrogels, hypoxic and nonhypoxic, confirms the effect of HI hydrogels on blood vessel recruitment in vivo. To control $O_2$ levels in vivo, calcium peroxide ($CaO_2$) is used as an oxygen-releasing compound to generate nonhypoxic gel (>8% $O_2$). To generate a hypoxic gel, calcium hydroxide $Ca(OH)_2$, a side product of $CaO_2$ decomposition that does not influence the change of $O_2$ tension within the gel matrix (FIG. 20) was encapsulated in the hydrogel. After subcutaneous injection of HI hydrogel, significant differences in the thickness of the surrounding granulation layer at the interface of the muscles and the implanted hydrogels is observed. (FIG. 19C and FIG. 21). Hypoxic hydrogels induce a stronger initial foreign body reaction than nonhypoxic gels. Also, the thickness of the granulation layer surrounding the hypoxic hydrogels decreases, whereas the layer surrounding the nonhypoxic gels does not change significantly (FIG. 19C). These results show that the foreign body reaction to HI hydrogel is similar to that previously reported for biocompatible materials (Zhang, L. et al., *Nature biotechnology*, 2013; 31:553-556). Moreover, HI hydrogels do not adversely affect local tissue during the wound-healing process. HI hydrogels also activate the foreign body reaction, which enables rapid blood vessel recruitment and infiltration into hydrogel matrices. For vascularization, a significant higher density of blood vessels surround hypoxic hydrogels than surround nonhypoxic gels after one day, with some blood vessels infiltrating into both hydrogel matrices (FIG. 19D and FIG. 22). Blood vessels surrounding and penetrating hypoxic hydrogels matrices increased much more than in nonhypoxic hydrogels (FIG. 19D). The size of blood vessels penetrating into the hypoxic hydrogels increased after injection (FIG. 23). As demonstrated, the HI hydrogels of the invention, which can induce acute hypoxic conditions in vivo, promote blood vessel recruitment and invasion from the host during the wound-healing process.

Many solid tumors contain poorly vascularized regions that are severely hypoxic and contribute to cancer progression by activating transcription factors (HIFs) that promote cell survival, tumor angiogenesis, and metastasis. Not surprisingly, tumor hypoxia is associated with a more aggressive disease course and poor clinical outcomes. The hypoxia-inducible hydrogels of the invention can serve as an engineered tumor model that can provide hypoxic microenvironment to mimic cancer microenvironments in vivo.

Figure 24A:
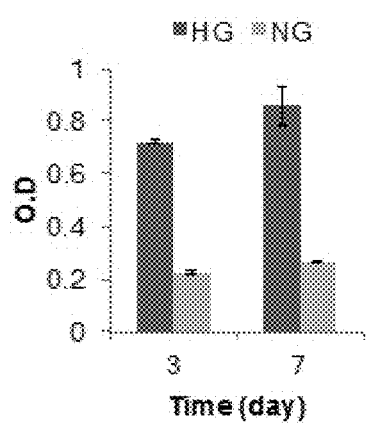
FIGS. 24A-24B: Cancer cell encapsulation within GtnFA HI hydrogels FIG. 24A KP cells proliferation within hypoxic gel (HG) and nonhypoxic gel (NG) for 7 days. The results are shown as the average values±SD (n=3).
Figure 24B:
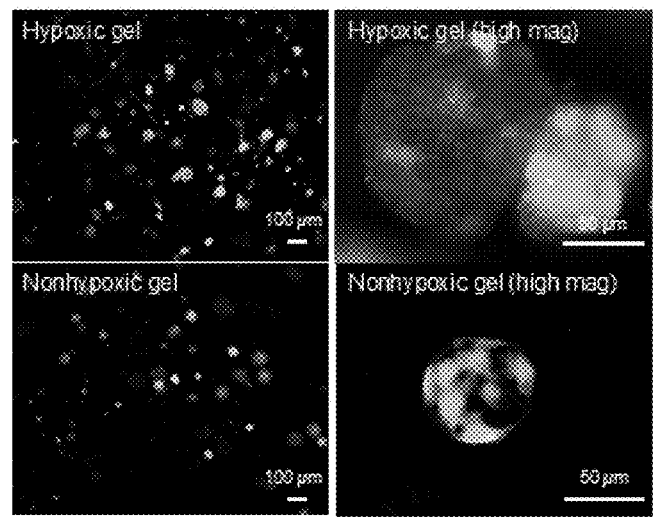

HI hydrogels of the invention generate advanced tumor models in vitro. To demonstrate the effect of a 3D hypoxic microenvironment on the cancer proliferation and spheroid formation, tumor cells (cancer cells) can be cultured within HI hydrogels. Encapsulation of tumor/cancer cells within different hydrogels, hypoxic gel and nonhypoxic gel, shows significantly different activities in hypoxic versus nonhypoxic gels. Cell proliferation within the hypoxic gel and nonhypoxic gel matrices analyzed by XTT assay shows higher cell proliferation within hypoxic gel compared to nonhypoxic gel (FIG. 24A). Different cell morphologies in hypoxic vs. nonhypoxic gels were also observed. Unlike the smaller aggregate formation of KP cells within nonhypoxic gel, the cells encapsulated within hypoxic gels formed bigger cancer spheroid after 7 days in culture (FIG. 24B). Collectively, these results demonstrate that hypoxic microenvironment promote cancer cell proliferation and cancer spheroid formation within the matrix.

Figure 25A:
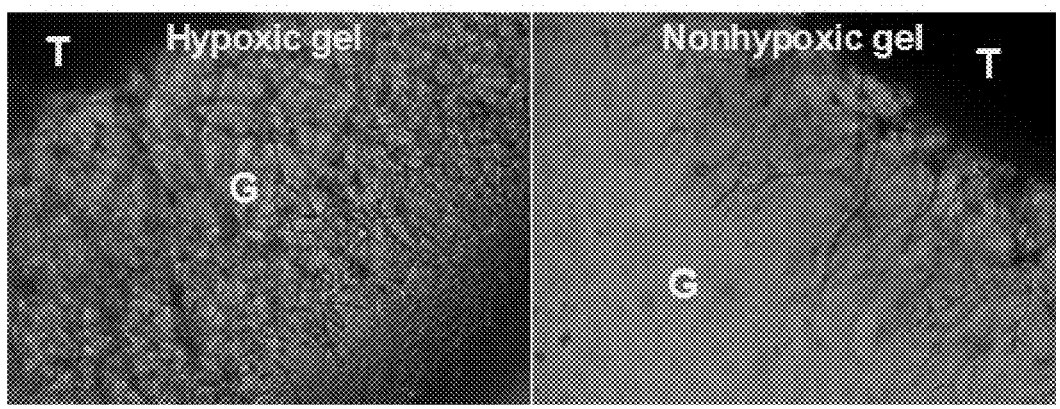
FIGS. 25A-25B: Tumor tissue encapsulation within GtnFA HI hydrogels.
Figure 25B:
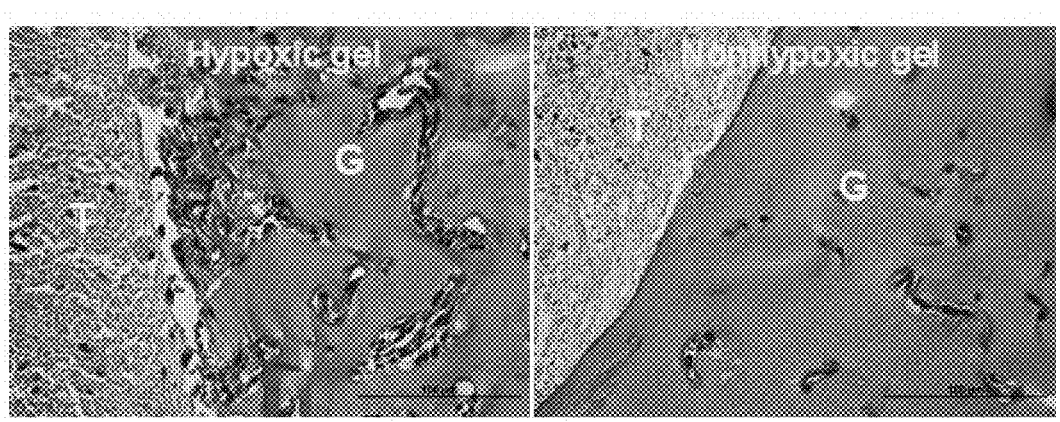

Encapsulation of tumor tissue within HI hydrogels can create more advanced tumor models similar to in vivo tumor environment. Mouse sarcoma tumor tissue (KIA) were encapsulated within different hydrogels (hypoxic gel vs. nonhypoxic gel). For tumor tissue encapsulation, pieces of tissue were prepared, such as in discs (diameter, 6 mm; thickness 0.8 mm) using Biopsy punch and tissue slicer. Different tumor tissue outgrowth was observed within the hydrogel matrices; the tissues cultured within hypoxic gel showed higher tissue outgrowth compared to nonhypoxic gels (FIG. 25A). Histological analysis confirmed tissue outgrowth toward hydrogels (FIG. 25B). Taken together, these results of tumor tissue encapsulation demonstrate that the hypoxic hydrogels of the invention promote tumor tissue activity, and provide advanced tumor models to study the mechanism of tumor progression, such as tumor invasion and metastasis as well as tumor angiogenesis.

The novel HI hydrogels of the invention, which induce hypoxic microenvironments, promote cancer cell and tumor tissue activities, and have a great potential as an advanced tumor model for cancer research. The HI hydrogels present precisely prolonged and controlled DO levels and gradients, which induce prolonged hypoxic conditions (up to 12 hours), with potential for a wide range of hypoxia-related applications.

EXAMPLES

The invention can be further understood in view of the following non-limiting examples.

Materials.

Gelatin (Gtn, type A from porcine skin, less than 300 bloom), laccase (lyophilized powder from mushroom, ≥4.0 units/mg), 3-methoxy-4-hydroxycinnamic acid (ferulic acid, FA), N-(3-dimethylaminopropyl)-N'-ethylcarbodiimide hydrochloride (EDC), N-hydroxysuccinimide (NHS), dextran (Dex, MW 70000), 2-bromoethylamine hydrobromide (BEAHB), triethylamine (TEA), 4-dimethylaminopyridine (DMAP), p-nitro-phenylchloroformate (PNC), poly(ethylene glycol) (PEG, MW 4000), tyramine (TA), dimethyl sulfoxide (DMSO), deuterium oxide ($D_2O$), and collagenase type IV were purchased from Sigma-Aldrich (Saint Louis, Mo.) and used as obtained without purification. Dulbecco's Phosphate-Buffered Saline (DPBS), Dulbecco's Modified Eagle Medium (DMEM), 0.05% trypsin, and fetal bovine serum (FBS) were all purchased from Gibco, Invitrogen (Life Technologies, CA). Dialysis membrane (molecular cutoff=3,500 Da) was purchased from Spectrum Laboratories (Rancho Dominguez, Calif.). For cell culture, human umbilical cord vein endothelial cells (HUVECs) and endothelial growth medium (EGM) were obtained from PromoCell (Heidelberg, Germany). Water-soluble tetrazolium salts-1 (WST-1) was obtained from Roche (Indianapolis, Ind.).

Statistical Analysis.

All measurements of hydrogel characterizations, including gelation time, swelling ratio, $O_2$ measurement, proteolytic degradation, and mechanical strength, were performed using triplicate samples for each data point. RT-PCR analysis for HIFs, MMPs, and proangiogenic factors were performed in triplicate with duplicate readings. Statistical analysis was performed using GraphPad Prism 4.02 (GraphPad Software Inc., La Jolla, Calif.); this software was also used to perform t-tests to determine significance. Significant levels, determined using post-tests, were set at: *$p<0.05$, $p<0.01$, and *$p<0.001$. All graphical data are reported.

Example 1: Synthesis of Functionalized Polymers

A phenolic agent (phenol molecule) can be conjugated to a polymer backbone to fabricate a HI hydrogel by consuming $O_2$ in laccase-mediated reactions. Gelatin (Gtn) is used as the polymer backbone for its cell-response properties, including cell adhesion sites and proteolytic degradability, which are critical in vascular morphogenesis (Hanjaya-Putra, D. et al., Blood, 2011; 118:804-815; Davis, G. E. et al., Circulation research, 2005; 97:1093-1107). Dex and PEG are used as the polymer backbone for their modifiability, bioactivity and hydrophilicity as well as the similarity of their properties to those of various soft tissues. In particular, the Dex molecule contains high content of hydroxyl functional groups that can be converted or modified easily with other molecules. A chain of Dex polymer includes three hydroxyl groups per repeat unit, which can allow for a high degree of substitution (DS) of target molecules (Jin, R. et al., Biomaterials 2007, 28, 2791). These relatively simple functionalizations form intramural hypoxia for both in vitro and in vivo vascular inductions.

Conjugating Gtn and FA:

Gelatin-g-ferulic acid (GtnFA) conjugate was synthesized using EDC and NHS as coupling reagents. For the synthesis, a mixture of DMSO and distilled water with a 1:1 volume ratio was prepared as a solvent. Gtn (1.0 g) was dissolved in 50 ml of the solvent at 40 C. FA (0.78 g, 4.0 mmol) was dissolved in 20 ml of the solvent and reacted with EDC (0.92 g, 4.8 mmol, 1.2 eq. of carboxyl unit of FA) and NHS (0.64 g, 5.6 mmol, 1.4 eq. of carboxyl unit of FA) at room temperature for 15 minutes to activate the terminal carboxyl groups of FA. The activated solution was then applied to the Gtn solution and a conjugative reaction was conducted at 40° C. for 24 hours. After reaction, the solution was dialyzed against water for five days (MWCO=3,500). After dialysis, GtnFA was freeze-dried and kept in a refrigerator before use.

Table 2 lists the synthesized GtnFA polymer series depending on the feed amount of FA molecules.

TABLE 2

Preparation of GtnFA conjugates

| No. | Gelatin (g) | FA (g) | EDC (g) | NHS (g) | FA content* (μmol/g of polymer) |
|---|---|---|---|---|---|
| #1 | 1.0 | 0.78 (4.0 mmol) | 0.92 (4.8 mmol) | 0.64 (5.6 mmol) | 44.70 ± 0.45 (DS45) |
| #2 | 1.0 | 0.39 (2.0 mmol) | 0.46 (2.4 mmol) | 0.32 (2.8 mmol) | 31.55 ± 0.76 (DS32) |
| #3 | 1.0 | 0.20 (1.0 mmol) | 0.23 (1.2 mmol) | 0.016 (1.4 mmol) | 12.53 ± 0.38 (DS13) |

*FA content was determined by UV measurement at 320 nm.

Conjugating Dextran and Tyramine.

Aminated dextran-g-poly(ethylene glycol)-tyramine (DexE-PT) was synthesized in multiple steps. Aminated-dextran (DexE) was synthesized by coupling of BEAHB and Dex using TEA as a catalyst as reported previously (Sun, G. et al., Biomaterials 2011, 32, 95; Sun, G. et al, Proc. Natl. Acad. Sci. U.S.A. 2011, 108, 20976). Briefly, Dex (1.5 g, 0.02 mmol) was dissolved in 60 mL of anhydrous DMSO at 50° C. and reacted with TEA (6.2 mL, 44.5 mmol) for 30 min. BEAHB (4.6 g, 22.5 mmol) was dissolved in 50 mL of DMSO. The BEAHB solution was then applied to the Dex solution and the reaction was conducted at 50° C. for 24 hours. After reaction, the solution was dialyzed against water for five days (molecular cutoff=6000-8000 Da). After dialysis, DexE powder was obtained by freeze-drying and kept the product in a refrigerator before use.

For the synthesis of amine-reactive PEG, the terminal hydroxyl group of PEG was activated with excess PNC as described previously (Park, K. M. et al., J. Mater. Chem. 2011, 21, 13180; Park, K. M. et al., Bioconjugate Chem. 2012, 23, 2042). PEG (10 g, 2.5 mmol) was dissolved in 100 mL of anhydrous dichloromethane (DCM) at room temperature under a nitrogen atmosphere. DMAP (0.916 g, 7.5 mmol) and TEA (0,759 g, 7.5 mmol) were dissolved in 20 mL of DCM and then added to the PEG solution. The mixture was reacted at room temperature for 15 min to activate the terminal hydroxyl groups. The PNC solution (1.511 g, 7.5 mmol) dissolved in DCM was dropwise to the activated PEG solution, and the reaction was conducted under a nitrogen atmosphere at room temperature for 24 hours. The molar ratio of PEG:DMAP:TEA:PNC was 1:3:3:3. After reaction, the solution was filtered by glass filtration using aluminum oxide, and the solvent was evaporated using a rotary evaporator at 30° C. The concentrated solution was precipitated in cold ether. The precipitate was filtered and dried overnight under vacuum to give a white powder of amine-reactive PEG (PEG-(PNC)$_2$).

DexE-PEG-TA (DexE-PT) conjugate was synthesized by coupling DexE and TA using PEG-(PNC)$_2$. For synthesis, PEG-(PNC)$_2$ (3.2 g, 0.8 mmol) was dissolved in 30 mL of anhydrous DMSO at room temperature under a nitrogen atmosphere. TA (0.11 g, 0.8 mmol) dissolved in 30 mL of anhydrous DMSO was added dropwise to the PEG-(PNC)$_2$ solution and the reaction was performed at room temperature under a nitrogen atmosphere for 6 hours to give mono-TA conjugated PEG (PNC-PEG-TA). The molar ratio of PEG-(PNC)$_2$ to TA was 1:1. The PNC-PEG-TA solution was applied to DexE (0.25 g 3.6 μmol) solution dissolved in 50 mL of anhydrous DMSO and the reaction was conducted at room temperature under a nitrogen atmosphere for 24 hours. After reaction, the solution was filtered using aluminum oxide to remove PNC salt and purified by dialysis against distilled water (molecular cutoff=6000-8000 Da) for five days to remove unconjugated molecules. The purified solution was lyophilized to give the DexE-PT polymer.

Degree of Substitution:

The degree of substitution (DS) of the phenolic agent was measured using an ultraviolet-visible (UV/Vis) spectrometer (SpectraMax; Molecular Devices, Sunnyvale, Calif.). GtnFA polymer (10 mg) was dissolved in 1 mL of a mixture of DMSO and distilled water with a volume ratio of 1:1, and the absorbance was measured at the 320 nm wavelength. DexE-PT (10 mg) was dissolved in 1 mL of DMSO, and the absorbance was measured at 275 nm wavelengths. The concentration of the conjugated phenol molecules (FA and TA) was calculated from a calibration curve given by monitoring the absorbance of a known concentration of FA or TA phenol molecule (standardized with the baseline measured using Gtn solution (10 mg/mL) or DexE-PT solution (10 mg/ml).

The chemical structures of GtnFA, DexE, PEG-(PNC)$_2$, and DexE-PT were characterized using a $^1$H NMR spectrometer (Bruker AMX-300 NMR spectrometer, Billerica, Mass.). Ten microgram per microliter (10 mg/mL of D$_2$O) of polymer solutions were prepared for the measurements.

Results

GtnFA conjugation is illustrated in FIG. 2. Synthesis of DexE-PT is illustrated in FIG. 26.

The degree of substitution in the GtnFA HI hydrogel is in the range of about 13 to about 45 μmol FA/g of polymer (FIG. 3B), and the DexE-PT HI hydrogel is about 170 (FIG. 28).

$^1$H NMR spectra indicates specific peaks of anomeric carbon and alkyl protons of Gtn, as well as the aromatic protons of FA (300 MHz, D$_2$O, δ6.48-7.45 ppm) (FIGS. 3A-3B), and the aromatic protons of TA (300 MHz, D$_2$O, δ6.8-7.2 ppm), the methylene protons of PEG repeating units (300 MHz, D$_2$O, δ3.4-3.8 ppm), and the anomeric protons of dextran repeating units (300 MHz, D$_2$O, δ4.95 ppm) (FIGS. 27A-27C).

Example 2: Preparation of Hypoxia-Inducible (HI) Hydrogels

HI hydrogels were synthesized by coupling carboxyl groups of FA to amine groups of Gtn (GtnFA) via a carbodiimide-mediated reaction (FIG. 2), and by coupling amine groups of TA and aminated Dex-E using amine reactive PEG as a linker (FIG. 26).

GtnFA Hydrogel Formation.

GtnFA HI hydrogels were prepared by mixing aqueous GtnFA polymer and laccase solution. Hydrogels (100 μl) were prepared in 1 ml vials at 37° C. Seventy five μL of the GtnFA polymer solution (4.0 to 6.7 wt %) and 25 μL of laccase solution (25 to 100 U/ml of stock solution) were simply mixed and gently shaken. To generate gel matrices of different thicknesses, we fabricated HI hydrogels in a 96-well plate (BD Bioscience or DO sensor patched plate-please see below for details) in a volume-dependent manner. For example, to generate hydrogel that was 2.5 mm thick, 80 μL of the mixture of polymer and laccase solutions was added in each well and allowed to react at 37° C. All solutions used were dissolved in DPBS (pH 7.4), and the final concentration of the hydrogels was 3 to 5 wt %.

GtnFA Gelation Time.

The gelation time of the GtnFA HI hydrogels was determined by the vial-tilting method. (Park, K. M., et al., *J Mater Chem;* 2011; 21:13180-13187). Briefly, 100 μL of hydrogel was prepared in a 1 mL vial and mixed gently to initiate the crosslinking reaction at 37° C. Gelation time was measured as the time point after inverting the solution when more than three minutes passed without flow. The experiments were performed with different concentrations of laccase at 6.25-25.0 U/mL; and polymer at 3-5 w/v %.

DexE-PT Hydrogel Formation.

Dex-HI hydrogels were prepared by mixing DexE-PT polymer solution and laccase solutions. To fabricate 100 μL of hydrogels, 75 μL of the polymer stock solution (4.0 w/v %-13.3 w/v %) and 25 μL of laccase stock solution (100 U/mL) were mixed and gently shaken at 37° C. The final concentrations of polymers and laccase were 3 w/v %-10 w/v % and 25 U/mL, respectively.

Measurement of Viscoelastic Properties.

Rheological analysis of the HI hydrogels using a rheometric fluids spectrometer (RFS3, TA Instruments, New Castle, Del.) with a 25 mm plate geometry were performed, as previously described (Park, K. M., et al., *J Mater Chem;* 2011; 21:13180-13187; Hanjaya-Putra, D. et al., *Blood* 2011, 118, 804). In the rheological experiments, hydrogel samples were prepared on the plate in the instrument. Dynamic time and frequency sweeps on hydrogel samples were performed in various conditions, including laccase concentration of 6.25-25.0 U/mL and polymer concentration at 3-10 w/v %. For dynamic time sweep, the elastic modulus (G') and viscous modulus (G") were monitored at 10 percent of strain and a frequency of 0.1 Hz at 37° C. For frequency sweeps, G' and G" were measured at 10 percent of strain and a frequency of 0.1 Hz at 37° C. A solvent trap wetted with deionized water was used to prevent sample evaporation.

Results

Figure 3A:
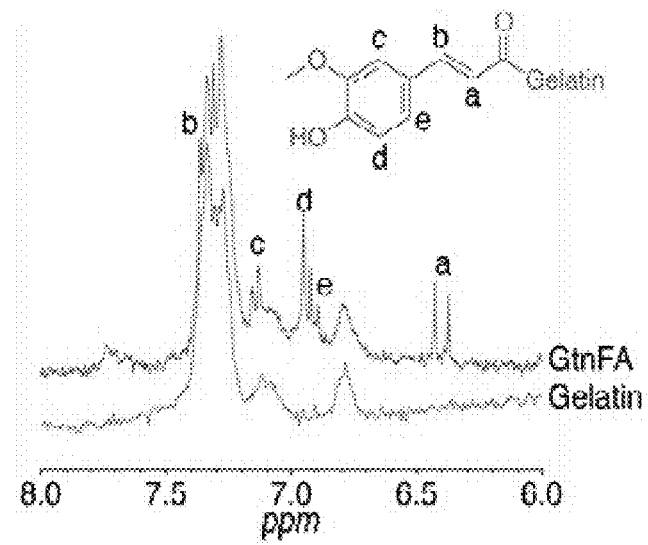
FIGS. 3A-3B: Characterization of GtnFA conjugate.
Figure 3B:
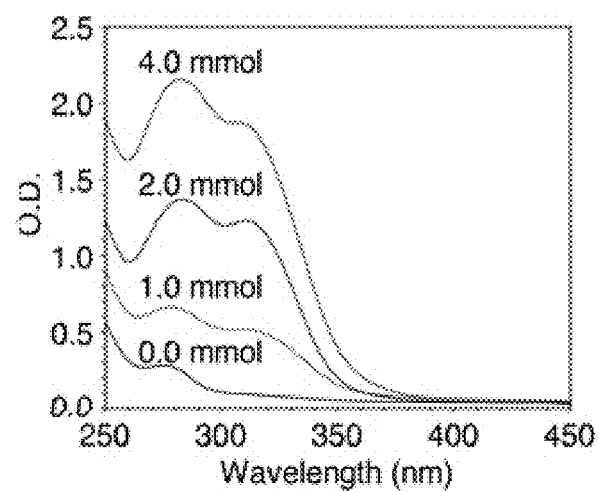

Synthesized GtnFA HI hydrogels are illustrated in FIG. 2. The chemical structure of the functionalized polymer characterized using $^1$H NMR, indicates specific peaks of anomeric carbon and alkyl protons of Gtn, as well as the aromatic protons of FA (FIG. 3A). UV/VIS spectroscopy determined the degree of substitution (DS) of the FA molecule (FIG. 3B). HI hydrogel are prepared by crosslinking FA molecules via a laccase-mediated chemical reaction (FIG. 1A) to form diferulic acid (DiFA) (FIG. 4), which yielded polymer networks (Riva, S., *Trends in biotechnology,* 2006; 24:219-226).

Figure 29C:
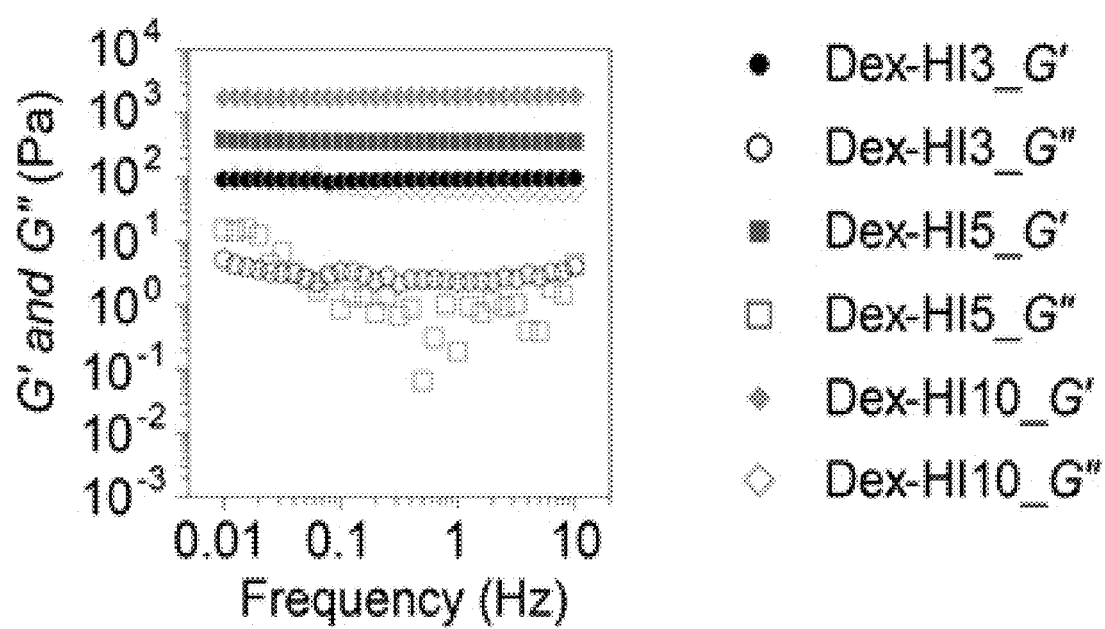

Rheological analysis, demonstrates GtnFA hydrogel formation and viscoelastic modulus. (FIG. 1B and FIG. 5). The crosslink point of elastic (G') and viscous (G") modulus, which provides an estimate of the gelation time, occurs within 2 to 30 minutes. Thus, laccase concentration affects the network formation kinetics. These data agree with the gelation kinetics observed by phase transition (FIG. 6A); higher concentrations of laccase and polymer induce faster hydrogel formation. This may have resulted from the rate of radical generation, which can induce DiFA formation, increased with higher laccase and polymer concentrations. Moreover, viscoelastic measurements showed tunable mechanical properties of the GtnFA HI hydrogels (35 to 370 Pa), Dynamic time sweep and frequency sweep of DexE-PT HI hydrogels with varying polymer concentrations demonstrated that hydrogels exhibited slower phase transition rate as polymer concentrations increased from 3 w/v % to 10 w/v % (FIG. 29A). G' values of Dex-HI3 hydrogel (DexE-PT HI hydrogel with 3 w/v %) increased dramatically after 1.3 hours, whereas G' of Dex-HI10 hydrogels increased after 2.7 hours, indicating that higher polymer concentrations induce slower hydrogel formation. Differences in O$_2$ diffusivity of precursor solutions result from increasing polymer concentration that induce lower O$_2$ diffusion in the solutions (data not shown), resulting in a slower laccase-mediated crosslinking reaction. Dex-HI hydrogels can be generated using lower molecular weight Dex (<70 kDa) and higher molecular weight PEG (>4 kDa) molecules to decrease polymer viscosity and to promote the crosslinking reactivity. Viscoelastic measurements using dynamic time sweep at the equilibrium swelling state exhibited tunable mechanical properties of the Dex-HI hydrogels (Dex-HI3, 110 Pa; Dex-HI5, 450 Pa; Dex-HI10, 1840 Pa) by varying polymer concentrations (FIG. 29B). Dynamic frequency sweep (0.01-10 Hz) showed that increasing frequency did not affect the elastic modulus (FIG. 29C). The physicochemical properties of Dex-HI hydrogels are summarized in Table 3.

TABLE 3

Hydrogel preparation and characterizations.

| Sample | Polymer conc. (w/v %) | TA Conc. (mM) | Michaelis-Meten parameters | | Elastic modulus (G', Pa) |
|---|---|---|---|---|---|
| | | | $V_{max}$ ($\mu$M sec$^{-1}$) | $K_m$ ($\mu$M) | |
| Dex-HI3 | 3 | 5.1 | 0.26 | 64.82 | 110 |
| Dex-HI5 | 5 | 8.5 | 0.26 | 73.93 | 450 |
| Dex-HI10 | 10 | 17.0 | 0.33 | 98.86 | 1840 |

These results demonstrate that the HI hydrogels have tunable mechanical properties, as well as stable network structures after hydrogel formation, which allow the hydrogels to maintain their 3D shapes as extracellular microenvironments to support cell function.

Example 3: In Vitro Proteolytic Degradation

Proteolytic degradability, which allows cell migration and niche remodeling (Lutolf, M. P. et al., *Nature Biotechnology*, 2005; 23:47-55; Lutolf, M. P. et al., *PNAS USA*, 2003; 100:5413-5418), is considered in designing cellular microenvironments.

In vitro degradation of GtnFA HI hydrogels was gravimetrically determined as in our previous study (Park, K. M., et al., *J Mater Chem*; 2011: 21:13180-13187). GtnFA hydrogels (100 µl) were prepared in microtubes and subsequently incubated in 500 µL of PBS with or without collagenase at 37° C. The media was removed from the microtubes at a predetermined time and measured the weight of degraded hydrogels (Wd). Fresh media were added into the tube after weighing. The weight of the remained hydrogels was then calculated according to the following formula:

Weight of hydrogel (%)=(Wd/Wi)×100% where Wd is the weight of the degraded hydrogels and Wi is the weight of the initial hydrogels.

Results

GtnFA HI hydrogels incubated with collagenase degraded completely within three hours, the rate varying with the concentrations of collagenase (0.001 to 0.05%) and polymer (3 to 5%) solutions (FIG. 7). These data demonstrate that the proteolytic degradability of the Gtn-based HI hydrogel is retained following functionalization with FA molecules.

Example 4: Cytocompatibility of HI Hydrogels

Cytocompatibility of hydrogels for cytotoxicity and viability was investigated. Precursor and free enzyme molecules can induce toxicity in a hydrogel matrix, prompting examination of toxicity of the conjugates and enzyme. In addition, cells were encapsulated within the HI hydrogels to determine cell viability and morphological changes within the hydrogel matrix.

Materials:

All solutions (GtnFA and DexE-PT solutions) for the in vitro cytotoxicity and viability studies were prepared using DPBS and filtered for sterilization using a syringe filter with a pore size of 0.2 µm.

Cytotoxicity of GtnFA:

Cytotoxicity of the synthesized GtnFA polymer and the enzyme was investigated using the XTT (Sigma-Aldrich), according to the manufacturer's instructions and our previous report (Sun, G., et al., *J Biomedical Materials Research. Part A*, 2010; 93:1080-1090). Briefly, newborn human foreskin fibroblasts (NUFF; Global Stem, Rockville, Md.) were expanded as previously reported (Hielscher, A., et al., *J Carcinog Mutagen.*, 2013; S13:005). For cytocompatibility, $2.8\times10^4$ cells/cm$^2$ were cultured in 100 µL media and in the presence of polymer solution (0.63 to 10.0 mg/mL) or laccase solution (1.6 to 25 U/ml) for 24 hours, following by their incubation in medium containing 20 percent (v/v) XTT solution for four hours. For the quantitative analysis, 100 µl of the medium was removed, placed in a 96-well plate, and the plate run in a microplate reader at the 450 nm wavelength. Cell viability was determined as a percentage of control cells (nontreated cells that were defined as 100% viable).

Cytotoxicity of DexE-PT:

The cytotoxicity of the synthesized DexE-PT polymer was investigated using WST-1 assay (Roche), according to the manufacturer's instructions. Briefly, human umbilical cord vein endothelial cells (HUVECs) (PromoCell, Heidelberg, Germany) were cultured in endothelial growth medium (EGM)(PromoCell). To test cytocompatibility, 1.0× 10$^4$ cells per a well in 96-well plate (BD Bioscience) were cultured in 200 µL media and in the presence of polymer solution (1 mg mL$^{-1}$) up to 3 days, followed by incubation in medium containing 10 percent (v/v) WST-1 solution for 2 hours. For the quantitative analysis, 100 µL of media was removed and placed in a 96-well plate, and the plate read in a microplate reader at 450 nm wavelengths. Cell viability was determined as a percentage of control cells (nontreated cells defined as 100% viable).

Cell viability of GtnFA HI hydrogels was evaluated using a live/dead kit (Invitrogen) as in previous reports (Park, K. M., et al., *Biomacromolecules*, 2010; 11: 706-712). Briefly, $5\times10^5$ NUFF cells/mL were encapsulated within Gtn FA HI hydrogels and cultured under standard cell culture conditions (37° C. and 5% CO$_2$) in high-glucose DMEM with 10% FBS. After incubation for 2 and 24 hours, each well was treated with 100 µl of 2 µM of the acetomethoxy derivate of calcein (calcein AM) and 4 µM of ethidium homodimer-1 (EthD-1) mixture and incubated at 37° C. for 30 minutes. The stained samples were washed three times using PBS and then counted with fluorescence microscopy (BX60, Olympus, Tokyo, Japan).

Results

No significant cytotoxicity in the GtnFA polymer was observed (80 to 98% of control) (FIG. 8A). In addition, encapsulated fibroblasts within the GtnFA HI hydrogels showed a predominantly viable fibroblast population, as well as cell spreading and elongation within GtnFA HI hydrogel matrices (FIG. 1C and FIG. 8B, FIG. 8C). DexE-PT exhibited no significant cytotoxicity with encapsulation of human umbilical vein endothelial cells (day 1, 100±9.1% of control; day 3, 114.7±8.6% of control) and the cells proliferated well up to day 3 (FIGS. 30A-30B). These results demonstrate the cytocompatibility of HI hydrogels as well as tunable parameters essential for their use as a 3D cellular microenvironment.

Example 5: Dissolved Oxygen (DO) Measurement and Mathematical Model Prediction

Induction of polymer network formation by $O_2$ consumption during hydrogel formation was investigated. Oxygen levels within the hydrogel matrix was determined by monitoring DO levels at the bottom of hydrogels using a noninvasive sensor patch (Abaci, H. E. et al., *American journal of physiology: Cell physiology*, 2011; 301:C431-440). Several factors affect DO levels and oxygen consumption rates, including hydrogel thickness, laccase concentrations, DS values of polymers, and culture media. A mathematical model developed in our previous report (Abaci, H. E. et al., *American journal of physiology: Cell physiology*, 2011; 301:C431-440) enables accurate prediction of DO levels and gradients within HI hydrogels.

DO Measurement:

DO levels were measured noninvasively throughout hydrogels using commercially available sensor patches (Presens, Regensburg, Germany), as previously described (Abaci, H. E., et al., *Am J Physiology Cell physiology*, 2011; 301: C431-440; Abaci, H. E., et al., *Am J Physiology Cell physiology*, 2010; 298: C1527-1537; Abaci, H. E., et al., *Biomedical microdevices*, 2012: 14:145-152). To measure $O_2$ levels at the bottom of hydrogels, polymer solutions were added on top of the sensors, which were immobilized in each well of a 96-well plate (BD Biosciences), and then mixed with laccase solutions (to form the hydrogel). All experiments were conducted in a controlled environment at 37° C. and 5% $CO_2$ in incubators with and without culture media (DMEM plus 100% FBS).

Hydrogel thickness was controlled by varying the polymer and enzyme solution volume. For model predictions, DO gradients within the hydrogels were estimated using a mathematical model based on Michaelis-Menten kinetics, as described in our previous report (Abaci, H. E., et al., *Am J Physiology Cell physiology*, 2011; 301: C431-440). Briefly, the oxygen consumption rate (R) of enzyme-mediated cross-linking reactions was assumed to follow Michaelis-Menten kinetics (Equation 1), and the Michaelis-Menten parameters of the oxygen-consuming hydrogel formation was determined, $$R = \frac{V_{max}C_{O2}}{K_m + C_{O2}} \quad (1)$$

where Vmax represents the maximum oxygen consumption rate and Km is the oxygen concentration at which the reaction rate is half of Vmax.

To determine these parameters, the steady-state DO level of the hydrogels (GtnFA: 3 wt % hydrogel, DS 45; DexE-PT: 3 w/v %, 5 w/v % and 10 w/v %; DS 170) formed with 25.0 U/mL enzyme was measured, and the experimental data using the Michaelis-Menten equation was plotted. The plots were calibrated according to the residual sum of squares (RSS) method using GraphPad Prism 4.02 (GraphPad Software Inc., La Jolla, Ca) to give the best-fit graphs between the theoretical equation and experimental values. The two-layer (air-hydrogel) and three-layer (air-media-hydrogel) models of the DO gradients were simulated with commercial software, Comsol Multiphysics (Comsol, LA, Calif.), as previously described (Abaci, H. E., et al., *Am J Physiology Cell physiology*, 2011; 301: C431-440).

Oxygen consumption kinetics during hydrogel formation follows Michaelis-Menten kinetics, as shown in equation (1). For accurate estimates of DO gradients in HI hydrogels, the $V_{max}$ and $K_m$ parameters were determined. DO levels in hydrogels are measured until they reach steady state. The oxygen consumption rate of the laccase-mediated reaction (experimental data) and the theoretical Michaelis-Menten equation (numerical model) using the initial $V_{max}$ and $K_m$ values were plotted. The graphs were then calibrated while varying the $V_{max}$ and $K_m$ parameters to obtain the best fit to the experimental values according to the residual sum of squares (RSS) method for GtnFA, FIG. 11; GraphPad Prism 4.02 for DexE-PT, FIG. 31b. The $V_{max}$ and $K_m$ values of the GtnFA HI hydrogels were 0.43M/sec and 70 M, respectively; the values for DexE-PT HI hydrogels were 0.26 μM/sec and 64.82 μM for Dex-HI3, 0.26 μM/sec and 73.93 μM for Dex-HI5, and 0.33 μM/sec and 98.86 μM for Dex-HI10, respectively. Using the Michaelis-Menten parameters determined for the given conditions, the DO gradients throughout the gel depth in two-layer (air-hydrogel) and three-layer (air-media-hydrogel) models were estimated.

Results

Several factors including hydrogel thickness, enzyme concentrations, polymer concentration, DS values of polymers, and culture media affected DO levels and oxygen consumption rates. Increasing laccase concentrations decreased the DO levels and the time to reach the minimum DO level ($DO_{min}$), demonstrating that high laccase concentrations induce rapid $O_2$ consumption reaction and low $O_2$ levels (FIG. 9A). Similarly, the higher DS value of FA molecules resulted in the lowest DO levels (FIG. 9B). Decreasing the FA content increased the $DO_{min}$. The FA molecule acts as a crosslinker, consuming $O_2$ molecules during hydrogel network formation.

For DexE-PT HI hydrogels, DO levels decreased dramatically during the initial 30 minutes, and maintained low $O_2$ tension (<0.5%, defined as the steady state) up to 1.5 hours for Dex-HI3, 3 hours for Dex-HI5, and 8 hours for Dex-HI10, demonstrating an ongoing chemical reaction. After steady state was reached, the DO levels increased gradually, demonstrating that the chemical reaction was complete. The higher polymer concentrations induced rapid $O_2$ consumption and maintained prolonged hypoxic conditions. As polymer concentrations were increased from 3 w/v % (Dex-HI3) to 10 w/v % (Dex-HI10), the hydrogels showed faster $O_2$ consumption rate during the initial 30 minutes and longer hypoxic conditions (up to 12 hours) (FIG. 31A). This is consistent with TA content increasing from 5.1 mM to 17.0 mM (consuming $O_2$ molecules), which induces a much faster chemical reaction. Dex-HI hydrogels generated longer hypoxic conditions (up to 12 hours) compared to Gtn-HI hydrogels (up to 1 hour). The prolonged hypoxic conditions of Dex-HI hydrogels provide an advantage to promote accumulation and stabilization of HIFs, which regulate myriad gene expression affecting cellular activities (Simon, M. C. and Keith, B., *Cell* 2007, 129, 465; Semenza, G. L., *Trends Mol. Med.* 2001, 7, 345; Heddleston, J. M. et al., *Br. J. Cancer* 2010, 102, 789; Mazumdar, J. et al., *Cell. Mol. Med.* 2009, 13, 4319). The prolonged hypoxic conditions in the Dex-HI can be achieved based on the chemical reaction parameters and thus the HI hydrogel can be tuned.

Oxygen measurements and computer simulations showed that HI hydrogels consume $O_2$ during their formation, yielding an $O_2$ gradient within the matrix; various factors could control the consumption rate. GtnFA thick hydrogels (>2.5 mm, 3 wt %, DS 45, and 25 U/mL of laccase) reached hypoxic level (<5%) when placed in culture media, evidencing suitability for providing artificial hypoxic microenvironments.

As shown in FIG. 10A, controllable DO levels depend on the GtnFA HI hydrogel thickness (3 wt %, DS 45, and 25 U/mL laccase). The $DO_{min}$ decreased as thickness increased, demonstrating that intramural DO levels vary with matrix thickness. The experimental DO values at the different hydrogel thicknesses compared to numerical DO values determined by the mathematical modeling confirm that the experimental values are similar to the numerical model simulated by using the obtained $V_{max}$ and $K_m$ values (FIG. 10B and FIGS. 31C-31E). These results showed that the $O_2$ consumption rate (i.e., hydrogel formation kinetics) follows the theoretical Michaelis-Menten equation.

The two-layer model showed that, 30 minutes after GtnFA hydrogel formation, the DO levels at the bottom of hydrogels decreased as gel thickness increased, due to insufficient oxygen diffusion (FIG. 10C[i]), and a broad range of $O_2$ tensions occurred within the gel matrices (10C[ii]). For instance, the $O_2$ gradient of the thin hydrogel (1.25 mm) ranged from 15 to 17%, while a thicker one (3.13 mm) exhibited a 1.8 to 21% range, demonstrating that hydrogel thickness strongly affected $O_2$ levels and gradients.

Computer simulation for media effects on $O_2$ gradients using the three-layer model shows hydrogels placed in media for 30 minutes exhibited lower intramural DO levels. FIG. 10D(i-ii) In fact, at thicknesses between 2.5 and 3.13 mm, DO levels were hypoxic (>5%) through the hydrogels depth. DO levels in matrices placed in culture media containing 100% serum exhibited lower DO levels, and slower $O_2$ diffusion than hydrogel in air (FIG. 9C). $O_2$ diffusion is slower in larger volumes of media, likely due to the media serving as a diffusion barrier between air and hydrogel matrices.

Increasing polymer concentration in DexE-PT hydrogel induced lower $O_2$ levels (Dex-HI3, 1.2±1.1%; Dex-HI5, 1.2±0.4%; Dex-HI10, 0.5±0.4%) and a broad range of 02 gradient after 30 minutes (Dex-HI3, 1.2%-20.3%; Dex-HI5, 1.2%-20.0%; Dex-HI10, 0.5%-20.3%). Dex-HI hydrogels exhibited lower $O_2$ levels and a wider range of $O_2$ gradient compared to Gtn-HI hydrogels (02 levels at the bottom of Gtn-HI hydrogel; 1.8%; $O_2$ gradient, 1.8-21%).

Using the given parameters, DO levels and gradients were estimated after theoretical in vivo injection of Dex-HI10 hydrogels. DO levels were simulated at different time points up to 8 hours (the end of the steady state of Dex-HI10). For this model prediction, a partial pressure of $O_2$ ($pO_2$) in subcutaneous tissue of 40 mmHg was assumed, following previous reports (B. Fischer, *J. Reprod. Fertil.* 1993; 99: 673; Y. N. Zhang, *Anal. Chim. Acta* 1993; 281: 513). As shown in FIG. 32A, the DO gradient from the core to the interface between the hydrogel and the tissue decreased during the initial 30 minutes: 10 minutes after injection, DO level of the hydrogel core is $4.3\times10^{-2}$ mol m$^{-3}$ and the DO level of the interface is $4.5\times10^{-2}$ mol m$^{-3}$; 30 minutes after injection, DO levels of the hydrogel core is $1.6\times10^{-2}$ mol m$^{-3}$ and the DO level of the interface is $3.6\times10^{-2}$ mol m$^{-3}$). Moreover, low $O_2$ levels were maintained for up to 8 hours where DO level of the hydrogel core is $1.6\times10^{-2}$ mol m$^{-3}$; a DO level of the interface is $3.6\times10^{-2}$ mol m$^{-3}$.

DO levels with different hydrogel geometries (e.g., ellipse, rectangle, and polygonal shape) were simulated. After 30 minutes, the DO gradient within the hydrogels was independent of the hydrogel geometry (FIG. 32B). Simulation of the $O_2$ gradients upon theoretical injection into tissue with pathological $O_2$ levels (<40 mmHg) that are ischemic and hence, hypoxic, showed that DO levels at the edge of the hydrogels were lower than the surrounding in vivo environment (FIG. 32B). Dex-HI hydrogels can induce an acute hypoxic environment (up to 12 hours) that can stimulate surrounding tissues in dynamic in vivo environments.

Example 6: Encapsulation of Cells in the Hypoxic Microenvironment

Cell encapsulation within HI hydrogel matrices demonstrates the importance of the 3D hypoxic microenvironment in cellular response, particularly vascular morphogenesis. Stimulation of the HIF pathway by HI hydrogels was investigated.

Cell Encapsulation:

Endothelial colony forming cells (ECFCs) from umbilical cord blood (Lonza, Walkersville, Md.) were cultured as previously described (Kusuma, S., et al., *FASEB Journal*, 2012: 26:4925-4936) in endothelial growth media-2 (EGM2, Lonza) containing 10% FBS on the plate coated with type I collagen (BD Biosciences, Franklin Lakes, N.J.). GtnFA polymer solution (4 wt %) was dissolved in PBS (pH 7.4) and filtered using a syringe filter with a pore size of 0.2 μm for sterilization. The solution was mixed with ECFC pellets to provide cell suspension, and then laccase solution (100 U/mL) was added at a volume ratio of 3:1 (polymer solution:laccase solution) and gently mixed for two minutes 37° C. The final concentration of the polymer, laccase, and cells were 3 wt %, 25 U/mL, and $2\times10^6$ cells/mL, respectively. The mixture was placed in the 96-well plate and allowed to react at 37° C. for 15 minutes. The ECFCs encapsulated within the hydrogels were cultured with 200 μL in growth media (Lonza) under standard cell culture conditions (37° C. and 5% $CO_2$) for up to 72 hours. The culture medium was replaced every 24 hours. ECFC morphologies were observed using optical microscopy (in phase-contrast mode) and confocal microscopy (LSM 510 Meta, Carl Zeiss). For confocal observations, ECFCs within hydrogels were fixed using 3.7% paraformaldehyde for 40 minutes at room temperature and washed three times using PBS. The fixed cells were permeabilized with 0.1 Triton X-100 for 20 minutes and incubated with 1% BSA blocking solution at room temperature for one hour. The hydrogel samples were incubated with phalloidin (1:40; Molecular Probes, Eugene, Oreg.) and Hoechst 33258 (1:10,000; Molecular Probes) to visualize the cytoplasm and nuclei, respectively.

Real-Time RT-PCR.

Quantitative real time RT-PCR was performed as described previously (Kusuma, S., et al., *FASEB Journal*, 2012: 26:4925-4936; Hanjaya-Putra, D. et al., *Blood*. 2011; 118:804-815). Briefly, total RNA was isolated from ECFCs encapsulated in hydrogels using TRIzol (Invitrogen) according to the manufacturer's instructions. Total RNA was quantified using an ultraviolet spectrophotometer and validated for having no DNA contamination. RNA (1 μg/sample) was transcribed using reverse transcriptase M-MLV and oligo(dT) primers (both from Promega Co., Madison, Wis.) according to the manufacturer's instructions. TaqMan Universal PCR MasterMix and Gene Expression Assay (Applied Biosystems, Foster City, Calif.) was used according to the manufacturer's instructions for HIF-1α, HIF-2α, VEGF, VEGFR, ANG1, ANG2, MT1-MMP, MMP-1, MMP-2- and β-actin, as described previously.

Live Staining and Angiogenesis Assay.

Live staining was performed using Calcein-AM (Invitrogen) to quantify the mean tube coverage, length, and thickness, as described previously (Abaci, H. E., et al., *Am J Physiology Cell physiology*, 2011; 301: C431-440). Briefly, ECFCs were encapsulated and cultured for three days using the above-described method. One hundred microliter of 2 µM calcein solution was added to each well, and the ECFCs embedded in the hydrogel were incubated at room temperature for 60 minutes. The stained cells were washed three times using PBS and then observed with fluorescence microscopy (BX60, Olympus, Tokyo, Japan). For the angiogenesis analysis, 5-20 images at 20× magnifications of different fields within the hydrogels were used, and the vascular tube structure was analyzed using MetaMorph software (Universal Imaging, Downingtown, Pa.) with the angiogenesis tools.

Zymography.

The conditioned media from each condition was collected at predetermined time points and analyzed for MMP-1 and MMP-2 as previously described (Hanjaya-Putra, D. et al., *Biomaterials*, 2012; 33:6123-6131). In brief, collected media were loaded on 10% gelatin (for MMP-2) and 12% casein (for MMP-1) zymography gels (Bio-Rad, Hercules, Calif.). We performed electrophoresis for 90 minutes at room temperature. After washing the gels in water, SDS was extracted from the gels with renaturation buffer (Invitrogen). MMP activities were developed in a developing buffer (Invitrogen) at 37° C. for 24 hours and visualized by staining with Coomassie Blue R-250.

Western Blot.

Western blot analysis was performed as described previously (Kusuma, S., et al., *FASEB Journal*, 2012: 26:4925-4936). Cell lysates were prepared in a Tris-Triton-X buffer (1% Trion-X, 150 mM NaCl, and 50 mM Tris, pH 7.5) with 1× protease inhibitor cocktail (Thermo Scientific, Waltham, Ma). Protein isolated from cell lysates was quantified with the DC assay (Bio-Rad) and boiled at 95° C. for five minutes in Laemmli buffer (Bio-Rad) with β-mercaptoethanol. Protein (25 µg/well) was loaded into a 4 to 20 percent SDS-PAGE gel (Bio-Rad). Proteins were transferred to nitrocellulose membranes, blocked in three percent nonfat milk for one hour, and incubated overnight at 4° C. (under constant shaking) with primary antibody: rabbit anti-MMP14 (MT1-MMP, 1:1,000) and GAPDH (1:3,000, both from Abcam, Cambridge, Mass.). We washed the membranes three times in Trisbuffered saline containing 0.1% Tween 20 (TBST) for 15 minutes each and incubated with antirabbit horseradish peroxidase (HRP) (1:1,000; Cell Signaling Technology, Danvers, Mass.). Membranes were washed three times in TBST, developed with enhanced chemiluminescence (Pierce), and visualized using the ChemiDoc XRS+ System (Bio-Rad).

Results

HI hydrogels stimulate vascular morphogenesis through HIF pathway activation (FIG. 12A), which demonstrates the importance of the 3D hypoxic niche in cellular response. ECFCs can be encapsulated within HI hydrogel matrices of different thickness, e.g. hypoxic gel, 2.50 mm, 1.25 mm. DO levels of hydrogels with ECFCs depend on gel thickness. DO levels of the hypoxic gels decrease dramatically for the first 30 minutes and retain prolonged low $O_2$ levels (under 0.5% $O_2$) (FIG. 13), demonstrating that the HI hydrogel allow the exposure of ECFCs to hypoxia and that the ECFCs also affect $O_2$ levels within the matrix. In fact, the DO levels of hypoxic gels without cells reached $DO_{min}$ within 30 minutes, followed by a gradual increase after the inflection point (FIG. 9C). DO levels within the hypoxic gels encapsulating ECFCs remained hypoxic after $DO_{min}$ for up to 24 hours (FIG. 13), likely due to oxygen consumption by the cells. In contrast, nonhypoxic gels exhibited higher $O_2$ levels (>8%) than hypoxic gels but with a similar pattern, due to the encapsulated ECFCs.

Figure 14:
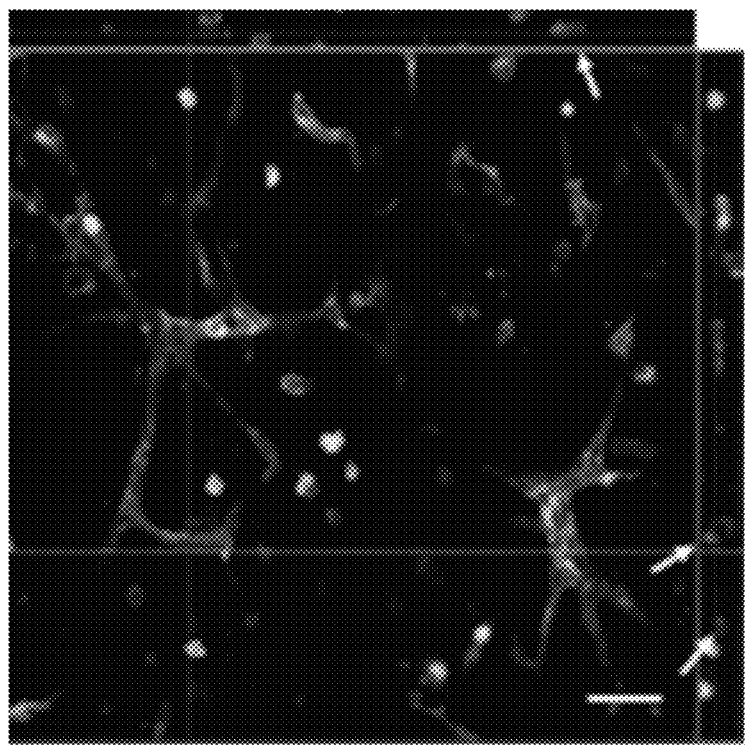
FIG. 14: Vascular morphogenesis of ECFCs within GtnFA HI hydrogel. Confocal z-stacks and orthogonal sections show lumen formation (indicated by arrows) within the vascular networks. Phalloidin in green; nuclei in blue. Scale bar is 50 μm.

ECFCs show different cell morphologies in hypoxic versus nonhypoxic gels. Unlike the limited ECFC sprout and tube formation of ECFCs within the nonhypoxic hydrogels, ECFCs within hypoxic gels underwent tubulogenesis, forming complex network structures after three days in culture (FIG. 12B(i)). ECFCs also have significant increases in tube coverage, in tube length, and in tube thickness (FIG. 12B [ii-iv]), demonstrating that the HI hydrogels stimulate vascular morphogenesis. More evolved vascular structures are generated in hypoxic gels than in nonhypoxic gels, as shown in FIG. 12C[i-ii]. Lumens in the vascular structures form in hypoxic hydrogels, indicating mature vascular tube formation (FIG. 12C[iii] and FIG. 14).

ECFCs cultured in hypoxic gels expressed significantly higher levels of two isoforms of HIFα (HIF-1α and HIF-2α) than ECFCs within nonhypoxic hydrogels (FIG. 3D[i]). Interestingly, HIF-1α gene expression gradually became upregulated in ECFCs in nonhypoxic gel for up to 24 hours during the culture period, probably due to the presence of FA molecules. A recent study demonstrated that free FA molecules could induce upregulation of HIF-1α expression in endothelial cells (ECs) in a concentration-dependent manner (Lin, C. M. et al., *J nutritional biochemistry*, 2010; 21:627-633).

Expression of three MMP genes in ECFCs membrane type 1 (MT1)-MMP, MMP-1, and MMP-2 play a critical role in vascular morphogenesis (Hanjaya-Putra, D. et al., *Blood* 2011; 118:804-815; Chun, T. H. et al., *J of Cell Biology*, 2004; 167:757-767, Stratman, A. N. et al., *Blood*, 2009; 114:237-247). All MMP gene expressions in ECFCs from the hypoxic gel were upregulated compared to ECFCs encapsulated in nonhypoxic gel (FIG. 12D[ii]). Also, higher levels of MT1-MMP and activated forms of MMP-1 and MMP-2 are found in hypoxic hydrogels (FIG. 15).

Analysis of gene expression of proangiogenic factors within the hypoxic microenvironment shows upregulation of VEGF and VEGFR2 in ECFCs encapsulated in hypoxic gel compared to nonhypoxic gel (FIG. 12D[iii]). ANG1, which contributes to blood vessel maturation and stabilization, was upregulated, while ANG2, an antagonist of ANG1, was downregulated in hypoxic hydrogels compared to nonhypoxic hydrogels. (FIG. 12D[iii]). Collectively, these results demonstrate that hypoxic hydrogels stimulate upregulation of proangiogenic and MMP genes affecting vascular morphogenesis.

Reoxygenation, the phenomenon in which hypoxic regions become more exposed to oxygen by changing $pO_2$, induces production of reactive oxygen specimens, which involves an angiogenic response (Pan, Y. et al., *Molecular and cellular biology*, 2007; 27:912-925). We previously demonstrated that reoxygenation affected the tube formation kinetics of ECs encapsulated in collagen gels in atmospheric conditions through a HIFα-independent pathway (Abaci, H. E. et al., *Am J Physiology: Cell physiology*, 2011; 301:C431-440). In the HI hydrogel system of the invention, oxygen fluctuates, from about 0.1% $O_2$ to about 1.3% $O_2$), and a gradually increases after media changes (FIG. 13). ECFCs encapsulated within HI hydrogels can be cultured with or without media changes, and ECFCs cultured without media changes undergo vascular morphogenesis similar to those cultured with media changes (FIG. 16), demonstrating that reoxygenation does not affect the angiogenic morphogenesis of ECFCs in HI hydrogel systems.

Example 7 Vascular Morphogenesis within HI Hydrogels

Vascular morphogenesis within HI hydrogels occurring through the activation of HIF was investigated. Small interfering RNA (siRNA) studies examined the involvement of HIF-1α and HIF-2α during ECFC tubulogenesis in HI hydrogels.

Small Interfering RNA Transfection.

Figure 17:
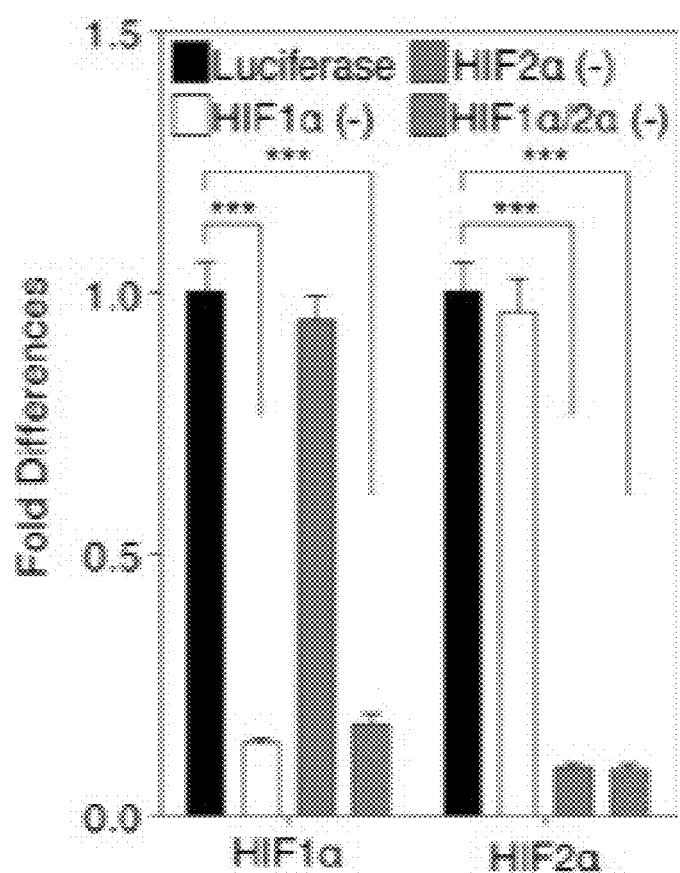
FIG. 17: siRNA study. Real-time RT-PCR analysis of siRNA-transfected ECFCs shows significant suppression of HIF-1α and/or HIF-2α compared to luciferase controls. Values shown are means±SD. Significance levels were set at: *p<0.05, p<0.01, and *p<0.001.
Figure 18:
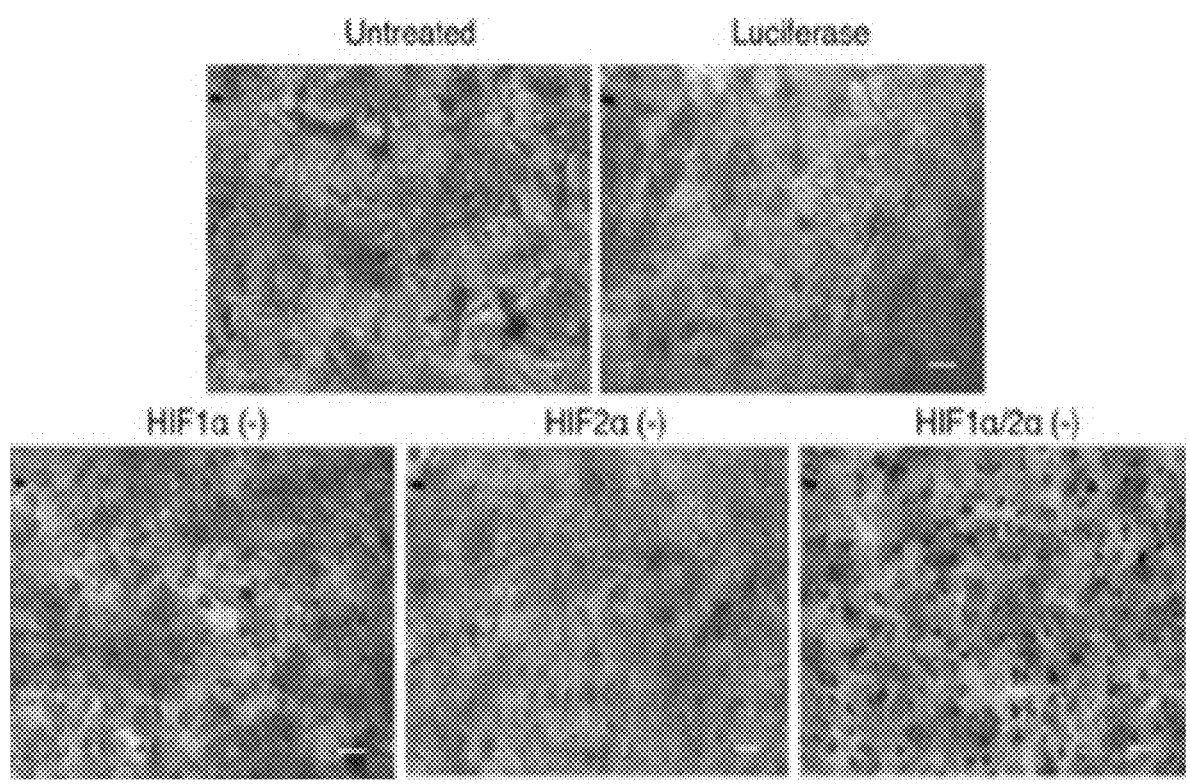
FIG. 18: Inhibition of vascular morphogenesis of ECFCs by siRNA suppression. Light microscopic images after three days in culture show that siRNA suppression of HIF-1α and/or HIF 2a affect the vascular morphogenesis. Scale bars are 50 μm.

ECFCs treated with either or both HIF siRNAs were encapsulated in HI hydrogels after confirming the suppression (FIG. 17). ECFC were transfected with siGENOME SMARTpool human HIF-1α and HIF-2α (Dharmacon, Lafayette, Colo.) following the manufacture's protocol, as previously described (Abaci, H. E., et al., *Am J Physiology Cell physiology*, 2011; 301: C431-440; Kusuma, S., et al., *FASEB Journal*, 2012: 26:4925-4936: Hanjaya-Putra, D. et al., *Blood*, 2011; 118:804-815). Cells were seeded on a six-well plate and treated with 100 nM siRNA. mRNA analysis was performed after 24 hours and used confirmed transfected cells for experiments after 48 hours.

Results

Figure 12E:
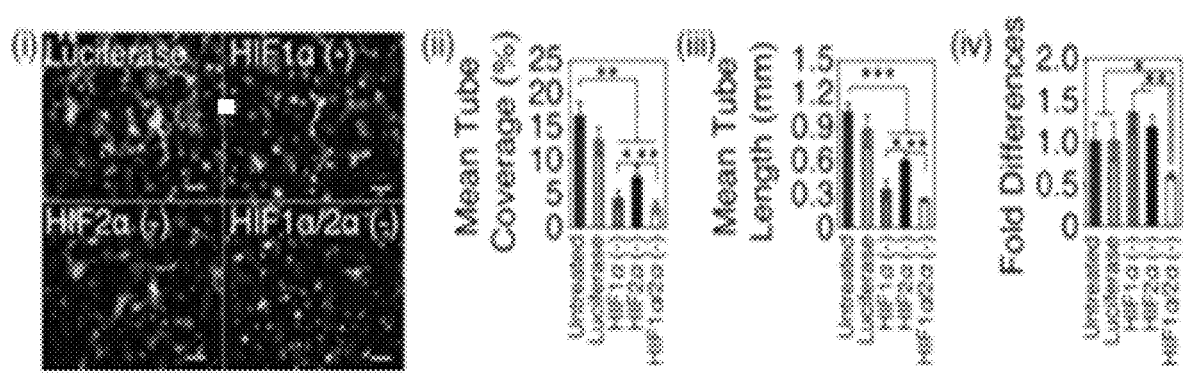

Knocking down each or both HIFs reduced tube area coverage and shortened tube length compared to untreated and luciferase-treated ECFCs (FIG. 12E[i-iii] and FIG. 18). Notably, when both HIFs were knocked down, most of the encapsulated ECFCs exhibited round shapes, even after three days in culture (FIG. 18). Significant downregulation of MT1-MMP expression was detected after 24 hours of culture in the ECFCs treated with both HIFs siRNA compared to nontreated, luciferase-treated, and each HIF-treated-alone groups (FIG. 12E[iv]). Collectively, these results demonstrate that regulation of HIF-1α and HIF-2α contribute to vascular morphogenesis of ECFCs within HI hydrogels and that this process involves the expression of MT1-MMP The HI hydrogels of the invention, which can induce hypoxic microenvironments, promote complex and mature vascular tube structures by activating HIFs through the upregulated expression of proangiogenic factors and MMPs.

Example 8: In Vivo Effects of HI Hydrogels

To demonstrate the in vivo application of HI hydrogels, the ability of the hypoxic hydrogel to induce acute hypoxia in surrounding tissues through in situ gel formation with oxygen consumption, which in turn would stimulate blood vessel invasion, was investigated (FIG. 19A).

Generation of Hypoxic and Nonhypoxic HI Hydrogels.

To control $O_2$ levels in vivo, calcium peroxide ($CaO_2$) is used as an oxygen-releasing compound to generate nonhypoxic gel (>8% $O_2$). To generate a hypoxic gel, calcium hydroxide $Ca(OH)_2$, a side product of $CaO_2$ decomposition that does not influence the change of $O_2$ tension within the gel matrix (FIG. 20) was encapsulated within the hypoxic hydrogel. A small amount of calcium peroxide ($CaO_2$; Sigma-Aldrich) and calcium hydroxide ($Ca(OH)_2$) (Sigma-Aldrich) were mixed with the polymer solution. The solid calcium peroxide begins to decompose and release $O_2$ molecules when in contact with water (Oh, S. H., et al., *Biomaterials*, 2009; 30:757-762). $CaO_2$ was encapsulated as an oxygen releasing compound to generate nonhypoxic hydrogel as a control group. To minimize the difference between the sample groups, $Ca(OH)_2$, was encapsulated within hypoxic hydrogels. $Ca(OH)_2$ does not influence the change of $O_2$ tension within the gel matrix. Concentrations of calcium derivatives were optimized previously to control oxygen levels for in vivo studies (Oh, S. H., et al., *Biomaterials*, 2009; 30:757-762).

In Vivo Delivery of HI Hydrogel.

HI hydrogels were injected subcutaneously in rats to investigate the in vivo angiogenic effects of HI hydrogels. Two hundred microliters of hydrogels formed with 0.02% $Ca(OH)_2$ (hypoxic hydrogel) and the same volume of hydrogels formed with 0.02% $CaO_2$ (nonhypoxic hydrogel) were injected into the backs of rats (four to six weeks old). For this study, polymer solutions were sterilized by filtering using syringe filter (pore size, 0.2 μm) and injected using 26-gauge needles. At each predetermined time point (one and three days), rats were sacrificed, the hydrogels removed with the surrounding tissue, the explants fixed in formalin-free Accustain fixative, and proceeded to histological analysis. The animal study was performed using a protocol (RA11A196) approved by The Johns Hopkins University Institutional Animal Care and Use Committee.

Histological Analysis.

After the explants were fixed as described above, the samples were then dehydrated in graded ethanol (80 to 100%), embedded in paraffin, serially sectioned using a microtome (5 μm), and stained with either hematoxylin and eosin (H&E) or underwent immunohistochemistry for α-SMA, as previously described (Sun, G., et al., *J Biomedical Materials Research Part A*, 2010; 93A: 1080-1090).

Results

Significant differences in the thickness of the surrounding granulation layer at the interface of the muscles and the implanted hydrogels occurs. (FIG. 19C and FIG. 21). Hypoxic hydrogels induce a stronger initial foreign body reaction than nonhypoxic gels. Also, the thickness of the granulation layer surrounding the hypoxic hydrogels decreases, whereas the layer surrounding the nonhypoxic gels do not change significantly (FIG. 19C). These results show that the foreign body reaction to HI hydrogel is similar to that previously reported for biocompatible materials (Zhang, L. et al., *Nature biotechnology*, 2013; 31:553-556). Moreover, HI hydrogels do not adversely affect local tissue during the wound-healing process. HI hydrogels also activate the foreign body reaction, which enables rapid blood vessel recruitment and infiltration into hydrogel matrices. For vascularization, a significant higher density of blood vessels surround hypoxic hydrogels than surround nonhypoxic gels after one day, with some blood vessels infiltrating into both hydrogel matrices (FIG. 19D and FIG. 22). After three days, the density of blood vessels surrounding and penetrating hypoxic hydrogels matrices increased much more than in nonhypoxic hydrogels (FIG. 19D). The size of blood vessels penetrating into the hypoxic hydrogels increased three days after injection (FIG. 23). As demonstrated, the HI hydrogels of the invention, which can induce acute hypoxic conditions in vivo, promote blood vessel recruitment and invasion from the host during the wound-healing process.

Example 9: Hypoxia-Inducible Hydrogels for Engineered Tumor Model

To access the importance of the 3D hypoxic niche to generate advanced tumor models in vitro, HI hydrogels were tested for promotion of cancer cell activities, such as proliferation, migration, and metastasis.

Materials:

Human sarcoma cells (HT1080) were purchased from American Type Culture Collection (ATCC) and mouse fibrosarcoma cells (KP) were isolated from a mouse model, as previously established (T. S. Karin Eisinger-Mathason et al., Cancer Discovery, 2013; DOI: 10.1158/2159-8290).

Mouse sarcoma tumor tissue (KIA) was obtained from mouse subcutaneous tumor generated by injection of KIA cells according to the previous report (T. S. Karin Eisinger-Mathason et al., Cancer Discovery, 2013; DOI: 10.1158/2159-8290). For transplant tumor, $1\times10^6$ KIA cells (isolated from KIA tumor) were injected into subcutaneous tissue of nu/nu mice (Charles River Laboratories). Tumors developed after 3 to 5 days and were monitored every other day, and animals were euthanized after 10 to 30 days.

Hypoxic and nonhypoxic gels were prepared as described above in Examples 1 and 2.

Cell Encapsulation:

Human sarcoma cells (HT1080) and mouse fibrous sarcoma cells (KP) were encapsulated similarly as described in Example 6 above. Cells were encapsulated within HI hydrogel of different thickness (hypoxic gel, 3.13 mm; nonhypoxic gel [as a control], 1.25 mm).

DO Measurement:

DO levels of hypoxic hydrogels with cells during culture period were measured as described in Example 5 above.

Results

The DO levels of the hypoxic gel decreased dramatically for the first 30 minutes and retained prolonged low oxygen levels (under 1% $O_2$) with oxygen fluctuation caused by media change during culture period (data not shown).

To demonstrate the effect of a 3D hypoxic microenvironment on the cancer proliferation and spheroid formation, the cells were cultured within the HI hydrogels for up to seven days. Cellular activities in hypoxic versus nonhypoxic gels were significantly different. Cell proliferation within the matrices were analyzed by XTT assay, which shows higher cell proliferation within hypoxic gel compared to nonhypoxic gel (FIG. 24A). Different cell morphologies in hypoxic vs. nonhypoxic gels were also observed. Unlike the smaller aggregate formation of KP cells within nonhypoxic gel, the cells encapsulated within hypoxic gels formed larger cancer spheroid after 7 days in culture (FIG. 24B). Collectively, these results demonstrate that hypoxic microenvironment promote cancer cell proliferation and cancer spheroid formation within the matrix.

Encapsulation of tumor tissues within HI hydrogels provide advanced tumor models similar to in vivo tumor environment. Mouse sarcoma tumor tissue (KIA) were encapsulated within different hydrogels (hypoxic gel vs. nonhypoxic gel). For tumor tissue encapsulation, pieces of tissue as discs were prepared (diameter, 6 mm; thickness 0.8 mm) using Biopsy punch and tissue slicer. Different tumor tissue outgrowth was observed within the hydrogel matrices. The tissues cultured within hypoxic gel showed higher tissue outgrowth compared to nonhypoxic gels (FIG. 25A). Histological analysis confirmed tissue outgrowth toward hydrogels (FIG. 25B). Taken together, these results of tumor tissue encapsulation demonstrate that the hypoxic hydrogels of the invention promote tumor tissue activity, and provide advanced tumor models to study the mechanism of tumor progression, such as tumor invasion and metastasis as well as tumor angiogenesis.

As demonstrated, the novel HI hydrogels of the invention, which induce hypoxic microenvironments, promote cancer cell and tumor tissue activities, and provide an advanced tumor model for cancer research.

In describing the present invention and its various embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

We claim:

1. A method of inducing in vitro blood vessel formation in a hydrogel comprising:
    a) adding to a gelatin-g-ferulic acid (GtnFA) polymer a cell or population of cells selected from the group consisting of pluripotent stem cells, adult stem cells, fibroblasts, endothelial colony-forming cells, human umbilical vein endothelial cells (HUVECs), tumor cells, or a combination thereof to create a mixture; and
    b) adding to the mixture of a) a sufficient amount of a laccase to cause crosslinking of the (GtnFA) polymer and create a hydrogel having an oxygen content less than 0.5% oxygen to induce in vitro blood vessel formation.

2. The method claim 1, wherein the cell or population of cells is in cellular growth medium.

3. The method of claim 1, further comprising implanting the hydrogel into a mammal.

4. A method of inducing in vitro blood vessel formation in a hydrogel comprising:
    a) adding to an aminated dextran-g-poly(ethylene glycol)-tyramine (DexE-PT) polymer solution a cell or population of cells selected from the group consisting of pluripotent stem cells, adult stem cells, fibroblasts, endothelial colony-forming cells, human umbilical vein endothelial cells (HUVECs), tumor cells, or a combination thereof to create a mixture; and
    b) adding to the mixture of a) a sufficient amount of a laccase to cause crosslinking of the (DexE-PT) polymer and create a hydrogel having an oxygen content less than 0.5% oxygen to induce in vitro blood vessel formation.

5. The method claim 4, wherein the cell or population of cells is in cellular growth medium.

6. The method of claim 4, further comprising implanting the hydrogel into a mammal.

\* \* \* \* \*